(12) United States Patent
Jones et al.

(10) Patent No.: US 11,768,132 B2
(45) Date of Patent: Sep. 26, 2023

(54) METHOD AND APPARATUS FOR SAMPLING LIQUID

(71) Applicant: Emerald Coast Manufacturing, LLC, Pensacola, FL (US)

(72) Inventors: Ronnie E. Jones, Pensacola, FL (US); Robert M. Gilliom, Wooster, AR (US)

(73) Assignee: Emerald Coast Manufacturing, LLC, Pensacola, FL (US)

( * ) Notice: Subject to any disclaimer, the term of this patent is extended or adjusted under 35 U.S.C. 154(b) by 0 days.

(21) Appl. No.: 18/104,557

(22) Filed: Feb. 1, 2023

(65) Prior Publication Data

US 2023/0175932 A1    Jun. 8, 2023

Related U.S. Application Data

(63) Continuation of application No. 16/902,113, filed on Jun. 15, 2020, now Pat. No. 11,598,696.

(60) Provisional application No. 62/861,437, filed on Jun. 14, 2019.

(51) Int. Cl.
  *G01N 1/14* (2006.01)
  *G01N 33/18* (2006.01)

(52) U.S. Cl.
  CPC .............. *G01N 1/14* (2013.01); *G01N 33/18* (2013.01)

(58) Field of Classification Search
  CPC .. G01N 1/14; G01N 2001/1043; G01N 33/18; G01N 1/18; G01N 2001/1454
  See application file for complete search history.

(56) References Cited

U.S. PATENT DOCUMENTS

| | | | |
|---|---|---|---|
| 2,355,620 A * | 8/1944 | Bower | ............... G01N 1/18 141/130 |
| 3,081,158 A | 3/1963 | Winter | |
| 3,587,670 A | 6/1971 | Brailsford | |
| 3,795,347 A | 3/1974 | Singer | |
| 3,858,450 A | 1/1975 | Jones | |
| 3,901,084 A * | 8/1975 | Brailsford | ............... G01N 1/18 141/130 |

(Continued)

FOREIGN PATENT DOCUMENTS

| CN | 107576532 A | 1/2018 |
|---|---|---|
| CN | 207456830 U | 6/2018 |

(Continued)

*Primary Examiner* — David A. Rogers
(74) *Attorney, Agent, or Firm* — AVEK IP, LLC

(57) ABSTRACT

The present invention provides a method and apparatus for wastewater sampling in all climates. The wastewater sampling apparatus pulls a sample from a stream or other body of water based on flow or time maintaining a consistent, repeatable, and accurate sample size. The present invention includes an all-weather housing. An integrated touchscreen control provides the ability to specify the volumes of water and program times and/or flow intervals to collect samples. Controls also allow control of the temperature within the sample compartment, both from the unit directly or from an external device. The present invention includes arcuate sample chamber and pivoting sample tube for accurate wastewater volume samples. The present invention may pull samples with vertical lifts of up to 29 feet or more and provide consistent accurate sampling exceeding current EPA transport velocity.

9 Claims, 73 Drawing Sheets

(56) References Cited

U.S. PATENT DOCUMENTS

| | | | |
|---|---|---|---|
| 3,901,087 A * | 8/1975 | Fabritius | G01N 1/14 73/864.35 |
| 3,924,471 A | 12/1975 | Singer | |
| 3,940,993 A | 3/1976 | Lapidot | |
| 4,022,059 A | 5/1977 | Schontzler et al. | |
| 4,037,472 A * | 7/1977 | Gates | G01N 1/14 73/864.35 |
| 4,077,263 A | 3/1978 | Brailsford | |
| 4,282,745 A | 8/1981 | Burr | |
| 4,343,766 A | 8/1982 | Sisti et al. | |
| 4,367,652 A | 1/1983 | Venuso | |
| 4,432,249 A * | 2/1984 | Levey | G01N 1/2035 73/863.83 |
| 4,631,968 A | 12/1986 | Aske | |
| 4,727,936 A | 3/1988 | Mioduszewski et al. | |
| 4,831,887 A * | 5/1989 | Crossley | G01N 1/14 73/864.34 |
| 5,084,241 A | 1/1992 | Parker | |
| 5,197,340 A * | 3/1993 | Jones | B01L 3/567 422/938 |
| 5,524,495 A | 6/1996 | Dudley | |
| 5,571,978 A * | 11/1996 | Gysi | B08B 9/46 73/865.8 |
| 5,629,201 A | 5/1997 | Nugteren et al. | |
| 5,652,397 A | 7/1997 | Dawson et al. | |
| 5,691,488 A | 11/1997 | Giannone | |
| 6,119,533 A | 9/2000 | Gherson et al. | |
| 6,257,076 B1 | 7/2001 | Snyder et al. | |
| 6,338,282 B1 * | 1/2002 | Gilbert | G01N 1/14 73/864.34 |
| 6,658,876 B1 | 12/2003 | Richardson et al. | |
| 7,363,830 B2 | 4/2008 | Girard | |
| 7,377,189 B2 | 5/2008 | Champseix et al. | |
| 7,430,930 B2 | 10/2008 | Zeller et al. | |
| 7,765,881 B2 | 8/2010 | Miller et al. | |
| 8,511,183 B2 | 8/2013 | Lineman et al. | |
| 8,701,510 B2 | 4/2014 | Gudmundsson | |
| 8,935,965 B1 | 1/2015 | Selbig et al. | |
| 9,752,965 B2 * | 9/2017 | Foote | G01N 1/24 |
| 2018/0052145 A1 | 2/2018 | Perkins et al. | |

FOREIGN PATENT DOCUMENTS

| | | |
|---|---|---|
| CN | 108801699 A | 11/2018 |
| CN | 209280369 U | 8/2019 |
| CN | 209495880 U | 10/2019 |
| CN | 210571559 U | 5/2020 |
| CN | 210741932 U | 6/2020 |
| JP | 4786469 B | 10/2011 |
| WO | 2012016063 A1 | 2/2012 |
| WO | 2019056036 A1 | 3/2019 |

\* cited by examiner

METHOD AND APPARATUS FOR SAMPLING LIQUID

CROSS REFERENCE TO RELATED APPLICATIONS

This application is a continuation of application Ser. No. 16/902,113, filed on Jun. 15, 2020, entitled METHOD AND APPARATUS FOR SAMPLING LIQUID, which is a non-provisional of application Ser. No. 62/861,437, filed Jun. 14, 2019, entitled METHOD AND APPARATUS FOR SAMPLING LIQUID.

FIELD

The present invention relates to a method and apparatus for sampling liquid and, more particularly, a method and apparatus for sampling wastewater with a programmable liquid sampler which utilizes an adjustable effective height of the intake tube to vary the sample size.

BACKGROUND

Vacuum liquid samplers are generally known in the art. Some automatic liquid samplers use a load cell to measure the sample weight. This measured weight is then used in an adaptive feedback loop to improve future sample size control. This technique is costly because load cells are expensive, mechanically fragile and require expensive signal conditioning electronics, resulting in an unreliable system.

A lower cost alternative is to fix the sample size by manually adjusting an intake tube up and down to vary the sample size. Vacuum is applied to the sample chamber via the vacuum/pressure port to draw the sample into the sample chamber via the suction tube until the chamber is overfilled. Pressure is then applied to the sample chamber, and the excess sample is discharged back out through the suction line until the sampling level is even with the bottom rim of the suction tube. At this point no more sample will be discharged. A valve on the discharge line is then opened and the sample is expelled from the sample chamber. This sampling technique is reliable and repeatable, but it is very difficult to adjust. Furthermore, not limiting the amount of initial oversample affects the quality of the sample. A reliable and repeatable sampling method and apparatus is desired.

SUMMARY

Embodiments of the invention are defined by the claims below, not this summary. A high-level overview of various aspects of the invention are provided here for that reason, to provide an overview of the disclosure, and to introduce a selection of concepts that are further described in the Detailed Description section below. This summary is not intended to identify key features or essential features of the claimed subject matter, nor is it intended to be used as an aid in isolation to determine the scope of the claimed subject matter. In brief, this disclosure describes, among other things, methods, systems, and apparatus for liquid sampling utilizing precise adjustment control to adjust the effective height of the suction tube within the sample chamber with feedback to limit the amount of oversample.

The present invention includes a method and apparatus for wastewater sampling in all climates. The wastewater sampling apparatus includes a refrigeration/heater unit to maintain the temperature of the sample to a range of +/−10 to 2 degrees C. in most climates. The wastewater sampling apparatus may pull a sample from a stream or other body of water based on flow, time, or combinations of flow and time, as desired by the operator, maintaining a consistent, repeatable, and accurate sample size.

The present invention provides an electronically controlled, heavy duty vacuum wastewater sampler. A refrigerated sampler allows for both composite and sequential sampling options with a high level of accuracy. The present invention includes an all-weather housing, making this all-season unit perfect for even the harshest of outdoor and indoor environments. An integrated touchscreen controls provides the ability to specify the volumes of water and program times and/or flow intervals to collect samples. Controls also allow control of the temperature within the sample compartment, both from the unit directly or from an external device. The present invention includes a powerful vacuum system to generate stronger purges to remove contamination and draw samples from greater distances. The present invention may pull samples with vertical lifts up to 29 feet or more and provide consistent accurate sampling exceeding current EPA transport velocity requirements.

DETAILED DESCRIPTION

Figure 1:
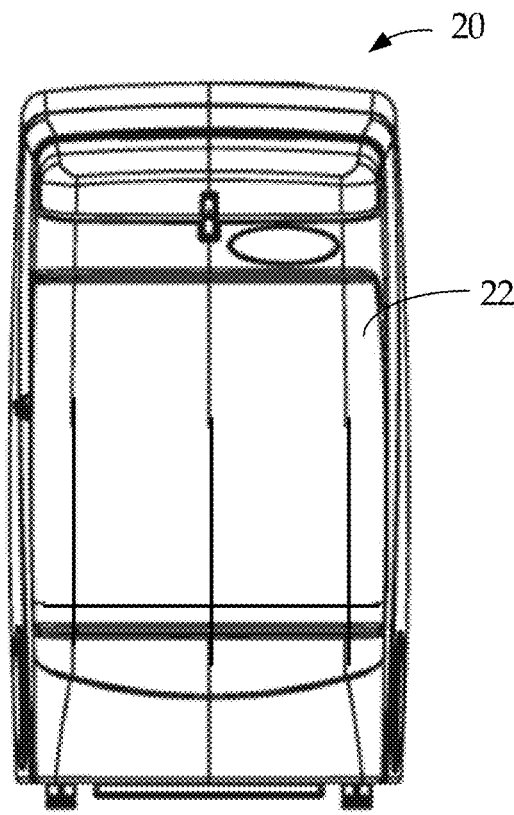
FIG. 1 is a front view of the housing for the apparatus for sampling liquid of the present invention.
Figure 3:
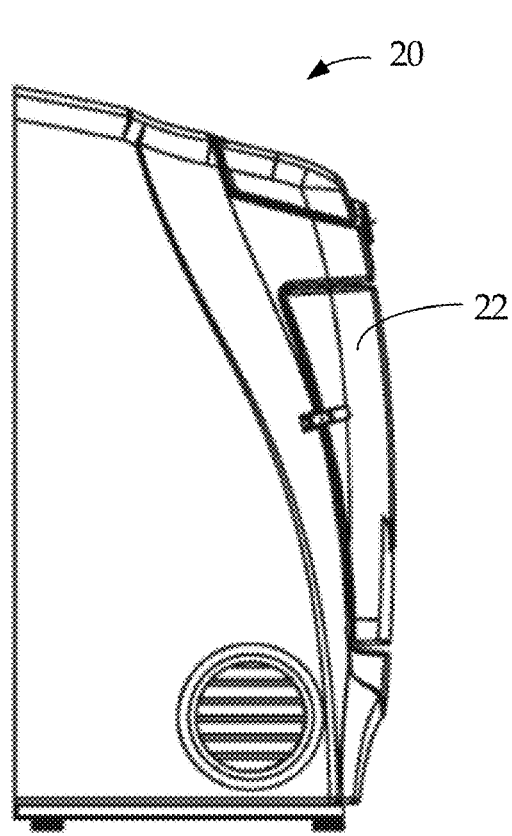
FIG. 3 is a side view of the housing of FIG. 1.
Figure 2:
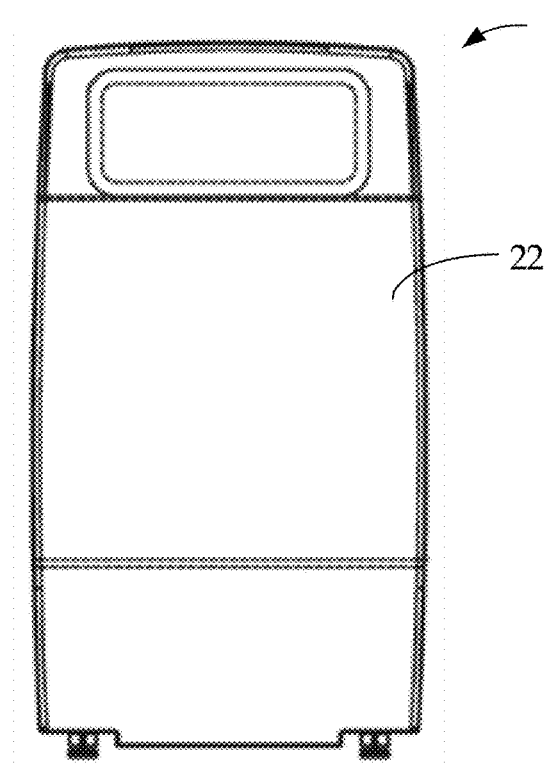
FIG. 2 is a rear view of the housing of FIG. 1.
Figure 4:
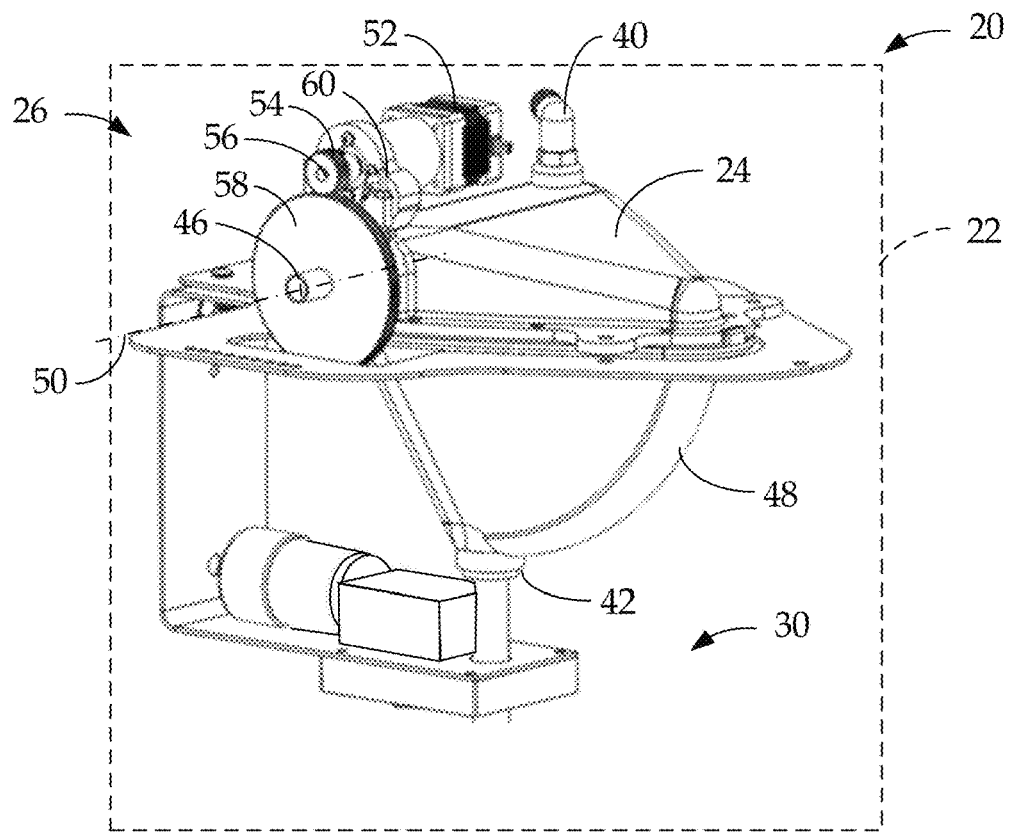
FIG. 4 is a perspective view of the major components of the apparatus for sampling liquid of the present invention.
Figure 5:
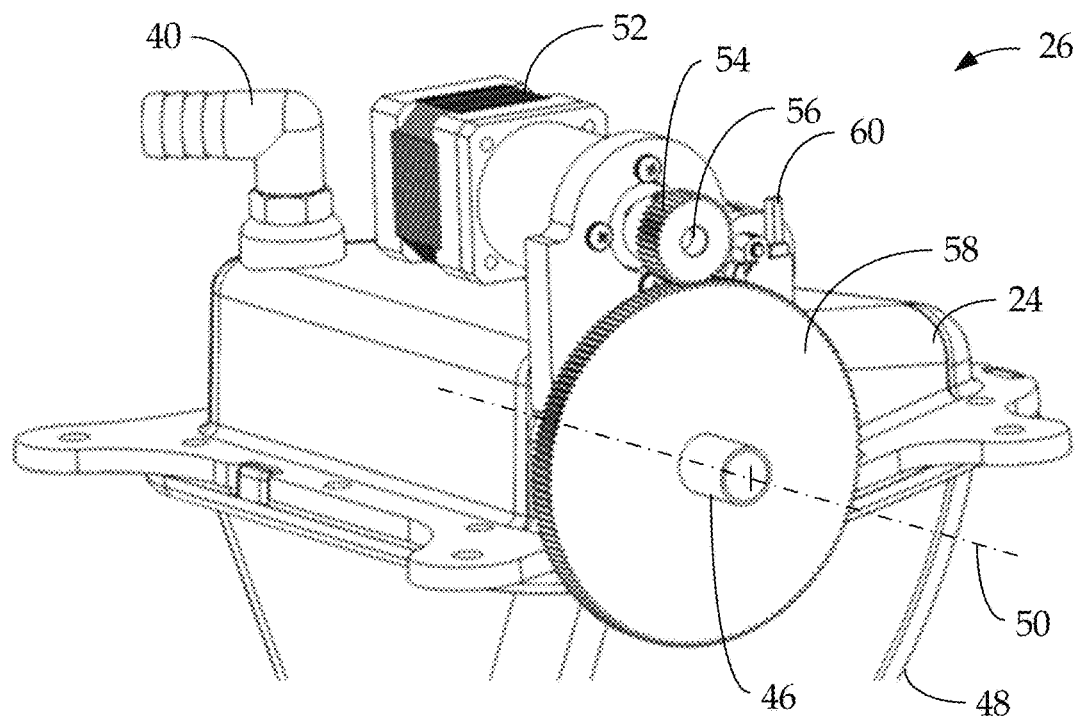
FIG. 5 is an enlarged partial view of the stepper motor and drive gear.
Figure 6:
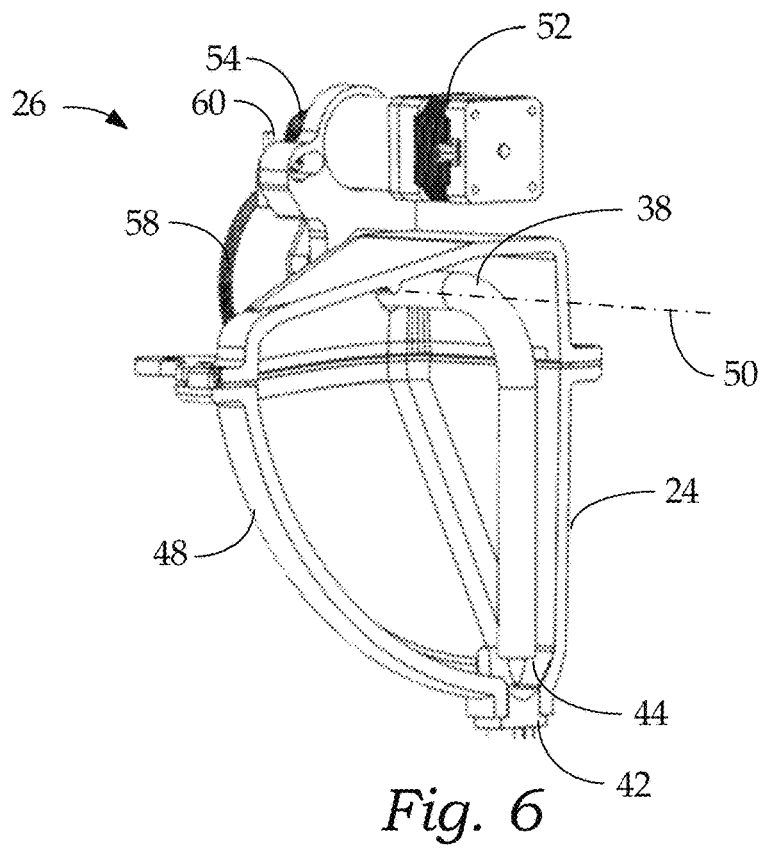
FIG. 6 is a view of the interior of the sample chamber.
Figure 7:
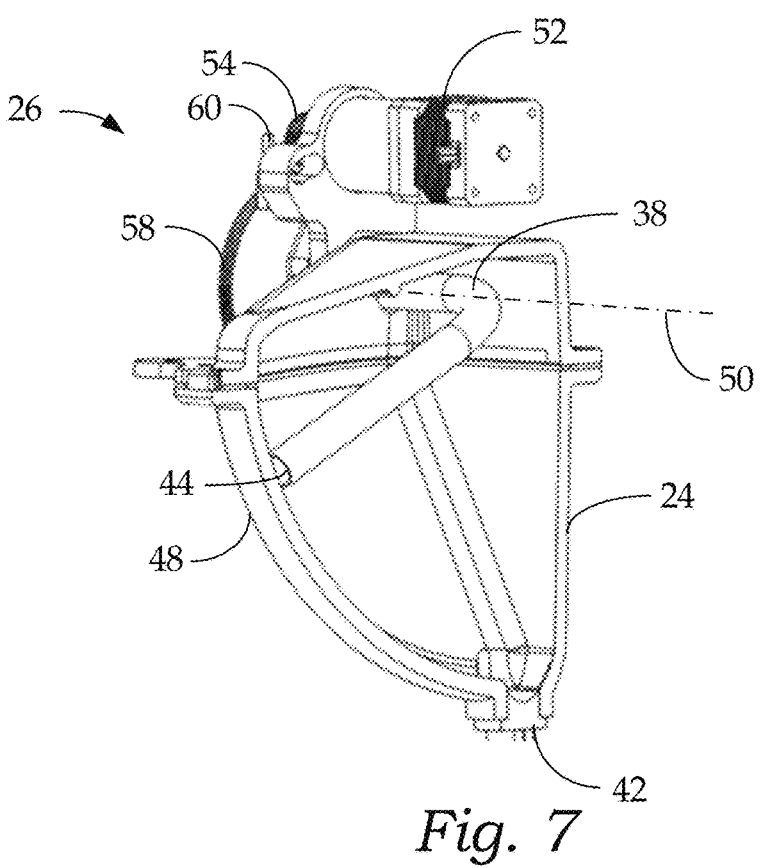
FIG. 7 is another view of the interior of the sample chamber with the sampling tube shown in another position.
Figure 8:
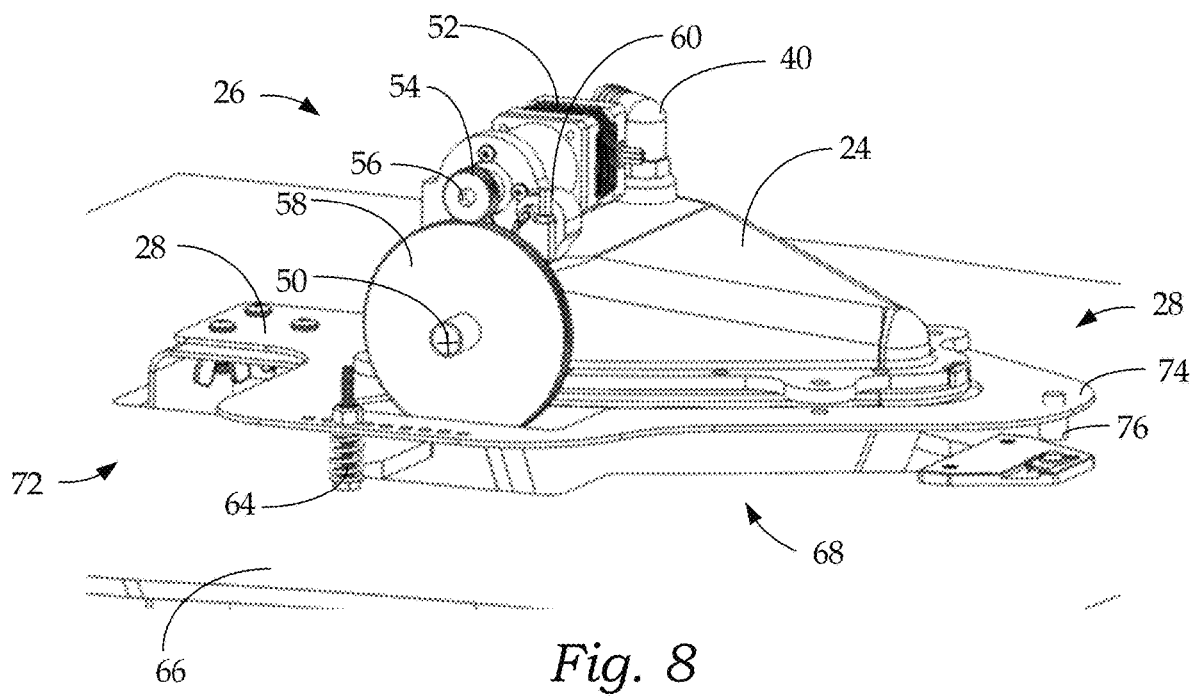
FIG. 8 is an enlarged partial view of a balancing sampling apparatus of the apparatus for sampling liquid of the present invention.
Figure 9:
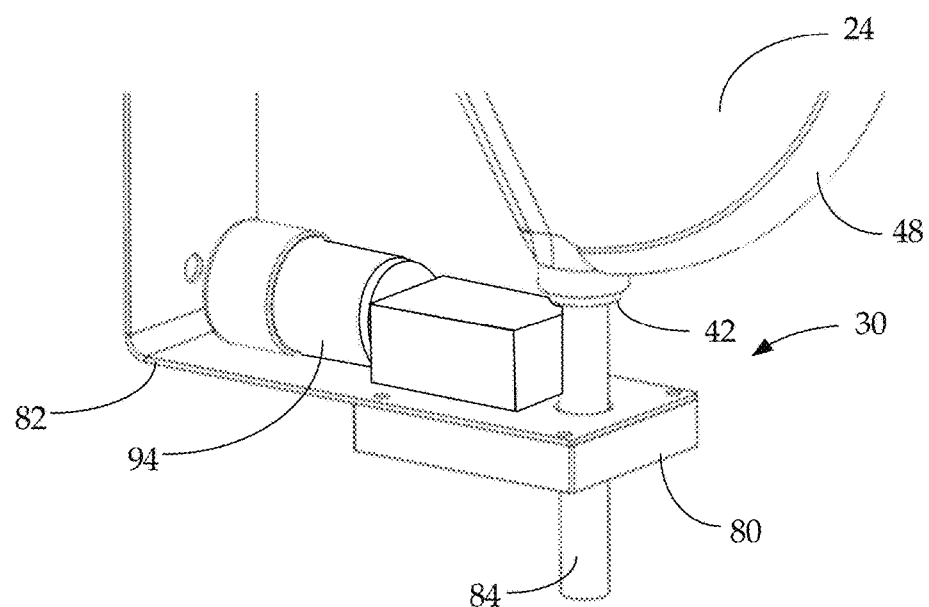
FIG. 9 is an enlarged partial view of a pinch valve assembly of the apparatus for sampling liquid of the present invention.
Figure 10:
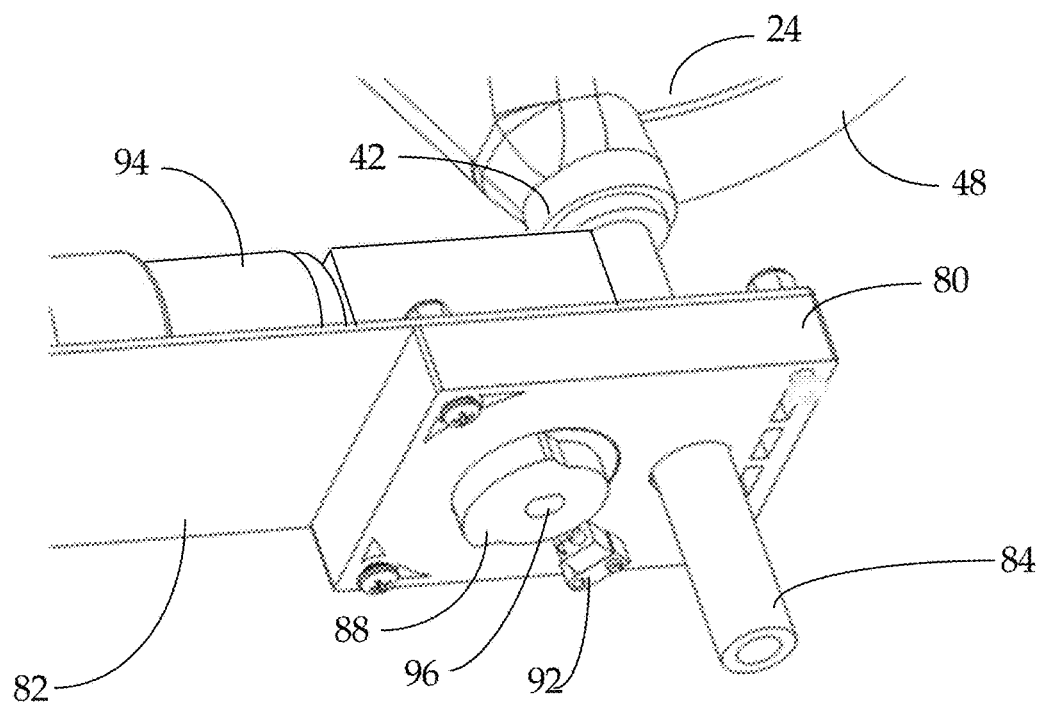
FIG. 10 is a view of the pinch valve assembly of FIG. 9 viewed from below.
Figure 11:
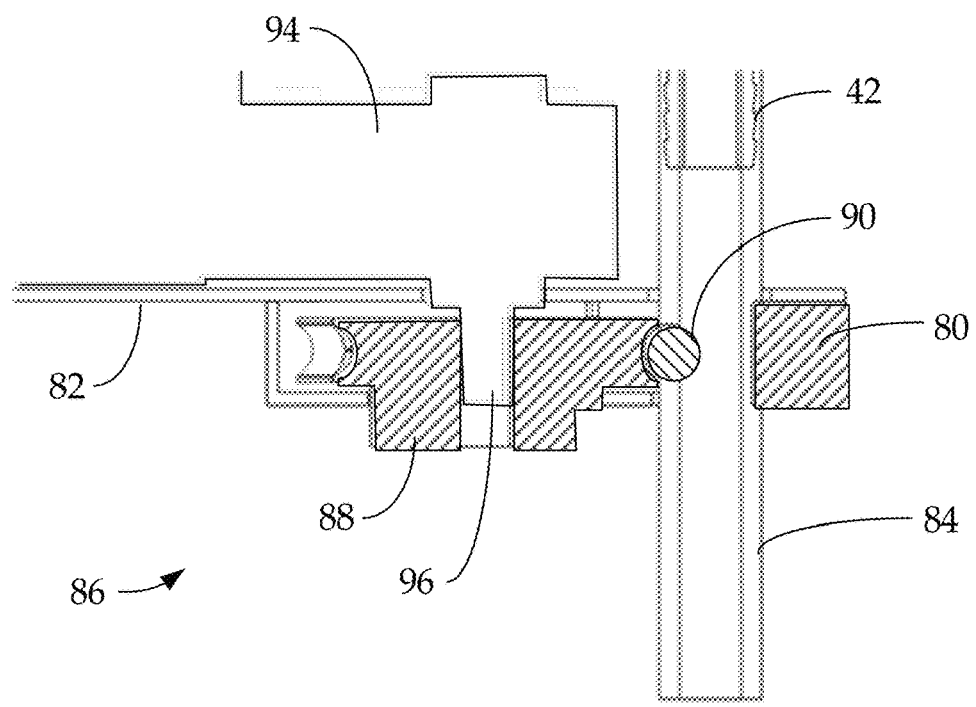
FIG. 11 is an internal view of the pinch valve assembly of FIG. 9.

The subject matter of select embodiments of the invention is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described.

Referring initially to FIGS. 1-12, an apparatus for sampling wastewater is generally indicated by reference numeral 20. The wastewater sampling apparatus 20 is mounted in a housing 22, and includes a sample chamber 24, a sampling tube position controller 26, a sample balance 28, a pinch valve assembly 30, a vacuum pump 32, a refrigeration unit 34, and a system controller 36.

The sample chamber 24 includes a sampling tube 38 pivotally mounted within the sample chamber 24, a vacuum/pressure port 40, and a drain 42. The sampling tube 38 includes an inlet 44 and an outlet 46. The sample chamber 24 is generally a wedge of a spherical segment with an arcuate outer wall 48 equidistant from the inlet 44 of the sampling tube 38 as the sampling tube 38 rotates about an axis 50. Selection of the vacuum/pressure is controlled by the vacuum/pressure solenoid 37 coupled to the controller 36.

The angular position of the sampling tube 38 is controlled by the sampling tube position controller 26. The sampling tube position controller 26 includes a drive motor 52, which is coupled to the system controller 36. In the preferred embodiment, the drive motor 52 is a stepper motor for precise control and position of the sampling tube 38.

Figure 12:
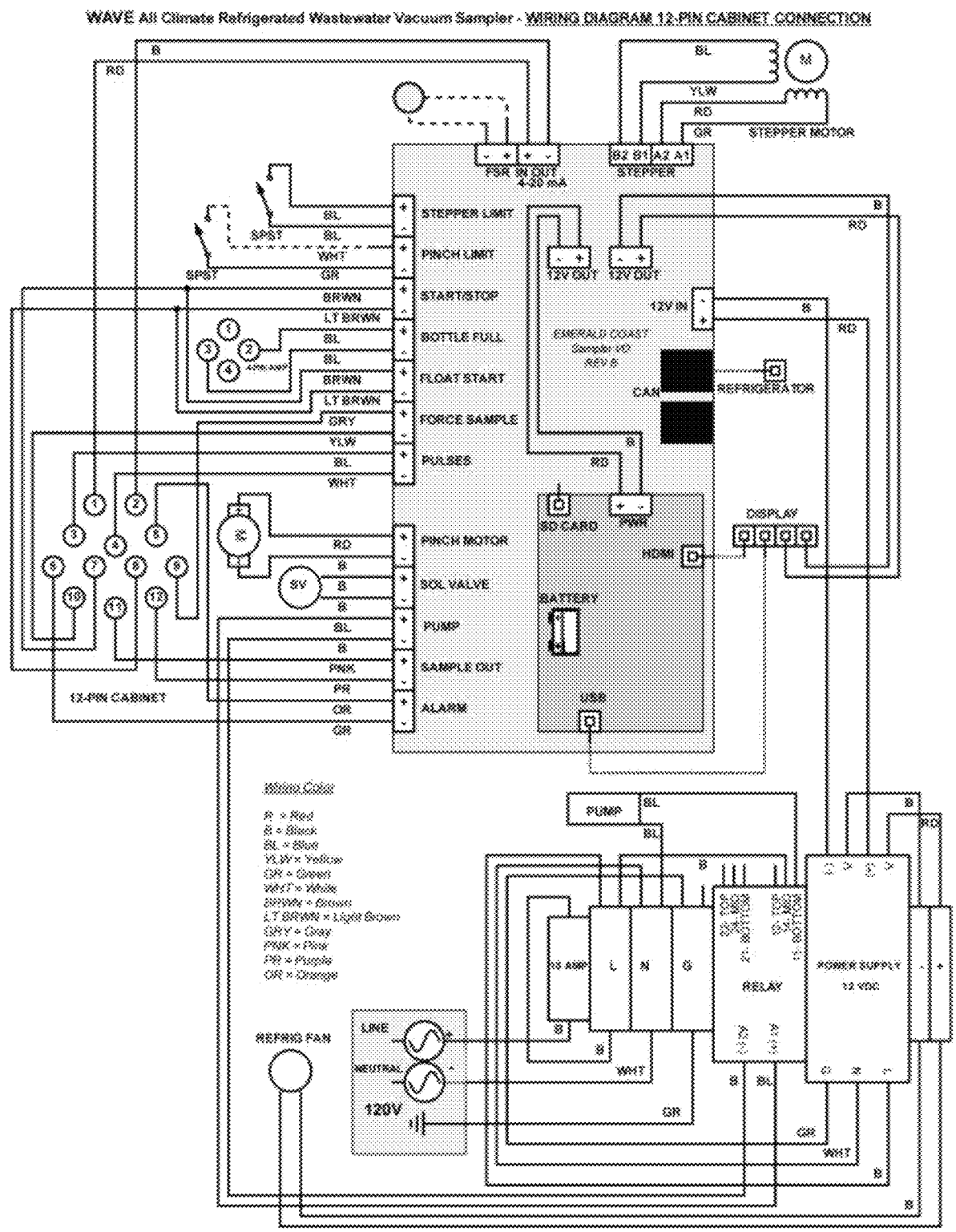
FIG. 12 is a schematic of the control unit for the apparatus of the present invention.

The system controller 36 includes a cooperative group of self-contained electronic modules (FIG. 12). These modules provide both hardware modularity and software modularity. The present embodiment is comprised of 1) a battery-backed embedded Linux computer, 2) a custom I/O controller controlled by an ARM Cortex M4 controller cooperatively connected to various custom designed I/O circuits, and 3) a custom refrigeration controller designed to measure temperature and perform the basic refrigeration controls. The embedded Linux computer communicates with the I/O controller and the refrigeration controller via the physical layer of a CAN bus interface. Each piece of hardware performs specific control functions.

The embedded Linux computer performs high-level functions such as 1) a fully graphical touchscreen user interface 100, 2) storing and retrieving all user configuration files, 3) performing real-time scheduling of the sampling events, 4) archiving and reporting sampling and exception information, 5) diagnostics, and 6) all external communications.

The I/O board contains its own microcontroller which interprets commands from the embedded Linux computer and then performs a single sample completely under self-control. This prevents non-deterministic behavior of Linux from corrupting the sampling process. Also, activities like flow monitoring and alarm generation are controlled via the I/O board. The I/O board also fully implements its own stepper motor controller for highly deterministic positioning of the sampling tube. The pinch-valve is controlled via an internal state machine within the I/O board.

The refrigeration control is a self-contained refrigeration control which keeps the cabinet temperature within preset limits. It communicates cabinet conditions to the embedded Linux controller.

Each hardware module incorporates its own software or firmware. Both the I/O board and the refrigeration control are programmed in C++ and utilize an open-source framework.

The embedded Linux microprocessor uses a variety of software modules to perform its functions. The User interface is written as a stand-alone process which communicates to a backend process via a REST API. This provides for an architecture which can support additional interfaces in the future. For example, a sampler can be controlled via a secure web site, or a mobile device can be redirected to interface to multiple samplers.

The backend process exposes a REST API interface, but also performs all scheduling, control and archiving functions. Time-critical functions, such as the CAN bus interface are forked as separate processes to leverage the multi-core architecture of the microprocessor. The embedded Linux computer can be easily connected to the Internet for remote diagnostics, calibration and control via Secure Shell protocol (SSH) or other known protocols.

The SSH protocol may be used to provide secure access for users and automated processes, interactive and automated file transfers, issuing remote commands, and managing network infrastructure and other mission-critical system components. The embedded Linux control also incorporates a companion battery backup module which monitors for power loss and provides for an orderly shutdown and reboot as necessary. This prevents power fluctuations from damaging the Linux file system. The battery backup module also performs real-time clock functions so the Linux system can maintain a consistent time-base independent of the Internet.

The drive motor 52 is mounted above the sample chamber 24. A drive gear 54 is mounted to a drive shaft 56 of the drive motor 52, which is coupled to a driven gear 58 mounted directly to the outlet 46 of the sampling tube 38. In the preferred embodiment, the drive motor 52 is a stepper motor and the position of the sampling tube 38 is controlled by counting the steps of the stepper motor 52. The positional limits of the sampling tube 38 may also be controlled by a limit switch 60, which is used for homing.

The sample balance 28 includes a balance plate 62. The sample chamber 24 and sampling tube position controller 26 are mounted to the balance plate 62 of the sample balance 28. The balance plate 62 balances at a fulcrum 64 which is rigidly mounted to the cabinet chassis 66. The center of mass of the sample chamber 24 is in front 68 of the fulcrum 64. The balance plate 62 includes adjustment apertures 70 to balance the sample chamber 24, sampling tube position and sample balance 28. The balance plate 62 may be positioned relative to the fulcrum 64 such that when the sample chamber 24 is empty, there may be slightly more mass in front 68 of the fulcrum 64 than behind 72 the fulcrum 64 resulting in a slight downward pressure at the front 74 of the balance plate 62. The front 74 of the balance plate 62 includes a cylindrical force concentrator 76 resting on top of a force sensor 78. The force sensor 78 may be a force sensing resistor, a load cell, a strain gauge, or other pressure sensor. The output of the force sensor 78 is coupled to the system controller 36, which linearizes the output as a function of force.

The system controller 36 positions the sampling tube 38 within the sample chamber 24 for a desired sample volume. The system controller 36 energizes the vacuum/pressure solenoid 37 to apply a vacuum to the vacuum/pressure port 40 of the sample chamber 24. Wastewater is drawn into the inlet 44 and out through the outlet 46 of the sampling tube 38 into the sample chamber 24. The output of the sample balance 28 is calibrated to slightly oversample the wastewater for a desired sample volume. When the volume of the wastewater exceeds the desired volume (weight), the system controller 36 energized the vacuum/pressure solenoid 37 to apply pressure to the vacuum/pressure port 40 of the sample chamber 24. A volume of oversampled wastewater is forced back out the outlet 46 through the inlet 44 until the level of the wastewater sample in the sample chamber 24 is below the rim of the outlet 46, resulting in a precise wastewater sample volume. In this manner, solids in the wastewater stream may also be discharged. When the desired wastewater volume is contained in the sample chamber 24, the pinch valve 80 is opened and the wastewater flows through the drain 42 and tube 84 to the collection bottle.

Other methods may be used to limit the amount of oversample in a sample cycle such as an external array of capacitance sensors on an exterior wall of the sample chamber 24. The capacitance sensors may signal when to terminate the suction cycle and initiate the pressure cycle. By using multiple capacitive sensor pairs in proximity to the sample chamber, the control microprocessor may be signaled to terminate the vacuum cycle at one of a multiple of distinct levels. Alternatively, a single linear capacitive sensing pair may be used for continuously monitoring levels. Discrete pairs may be preferable for simplicity and noise immunity.

The pinch valve assembly 30 serves to retain liquid within the sample chamber 24, then release the fluid when sampling is completed. The pinch valve assembly 30 includes a housing 80 mounted to a bracket 82, which is coupled to the balance plate 62. The pinch valve assembly 30 is suspended below the sample chamber 24, in alignment with a drain tube 84 coupled to the drain 42 without contacting any other component within the enclosure. A pinch valve assembly 86 is mounted in the housing 80 and includes a rotating eccentric cam 88, a floating pinch rod 90 and a limit switch 92. A drive motor 94 is mounted to the bracket 82 and includes a drive shaft 96 coupled to the rotating eccentric cam 88. The drain tube 84 is composed of a relatively soft flexible material such as vinyl, rubber or silicone, that is easily compressed to create a tight seal to prevent any flow through the tube 84, and readily springs back to its original shape when not compressed. As the drive motor 94 rotates the eccentric cam 88, the pinch rod 90 is pressed against the drain tube 84 withing the housing 80 to stop fluid flow through the drain tube 84 from the sample chamber 24. The limit switch 92 is activated by the eccentric cam 88 for positional feedback. As the drive motor 94 rotates the eccentric cam 88 to open the pinch valve, the pinch rod 90 is translated away from the drain tube 84, which returns to its original shape allowing fluid to flow through the drain tube 84 from the sample chamber 24.

The user interface 100 is a touch screen that provides information and feedback to the user. The home screen is the main screen viewed on start up. The home screen allows easy access to program information and the status of the current running program and its settings under it.

Figure 13:
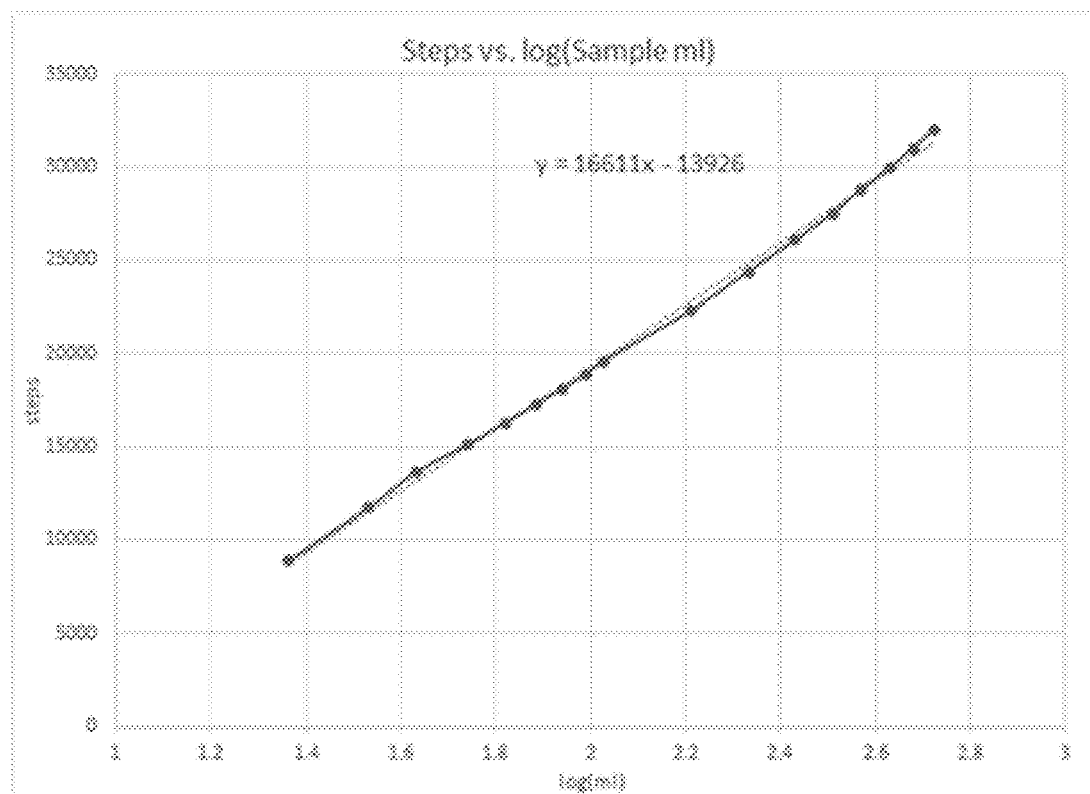
FIG. 13 is a chart showing the relationship between the position of the sampling tube and sample size using a least-squares method of regression.
Figure 14:
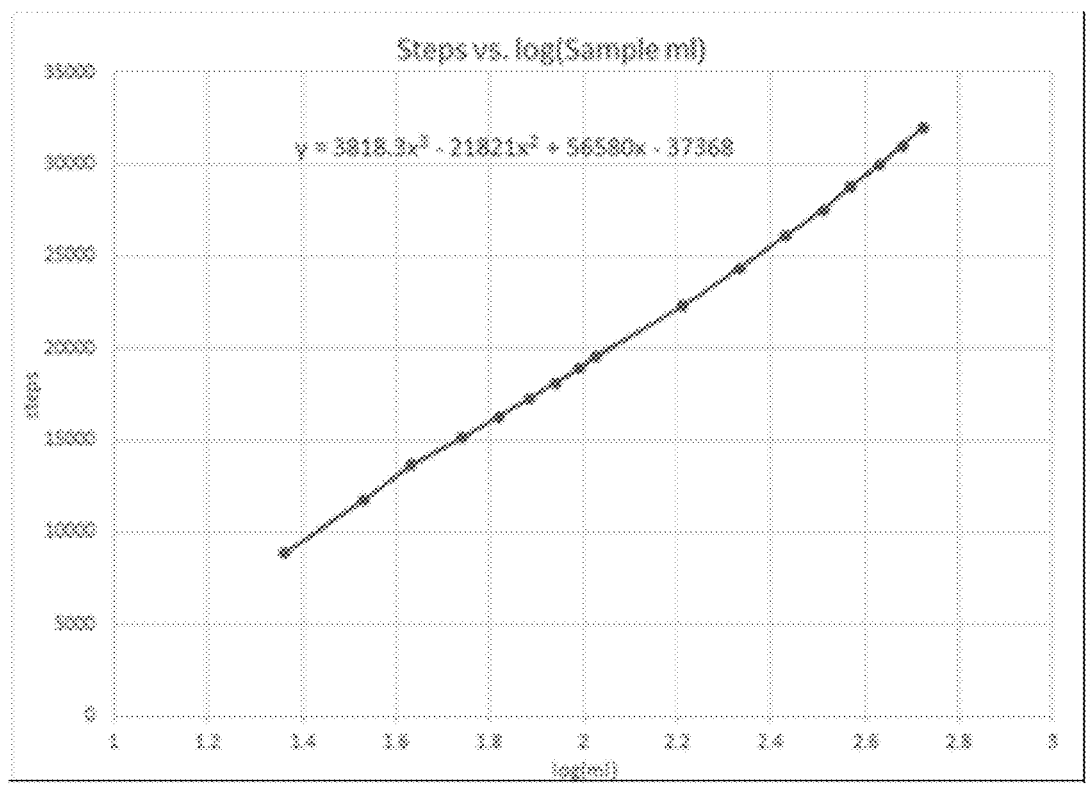
FIG. 14 is another chart showing the relationship between the position of the sampling tube and sample size using a higher order polynomial best fit regression.

Referring to FIGS. 13 and 14, software calibration of sample size may be varied by changing the angle of the sampling tube 38 relative to the sample chamber 24. The larger deflection from vertical, the larger the sample size. Since the deflection from vertical is performed via a stepper motor 52, a mathematical relationship may be determined linking steps as a function of sample size in milliliters. Because of the shape of the container 24, and because the depth of the sample in the container is a function of the cosine of the deflection angle, the function relating sample size to steps is highly non-linear. Consequently, there is a need for each chamber and sampling tube assembly to be software calibrated. For small sample sizes, many steps have a very small impact on size, but for large sample sizes only a few steps can be significant. However, the chamber is designed such that the function relating the logarithm of sample size to steps is quite linear. Thus, a relationship for steps as a function of sample size can be established for each container and sampling tube assembly by using a least-squares method of regression (see for example, FIG. 13).

Another embodiment may be realized by using a higher order polynomial best fit regression method (FIG. 14). A preferred embodiment is realized by combining these techniques to allow a search algorithm to find a specific set of (log(ml), step) pairs. For example, multiple samples can be taken to determine the precise steps to produce 20, 50, 100, 200, 300, 400 and 500 ml sample sizes. A smooth function may be determined by using mathematical spline functions to join the (log(ml), steps) pairs. This minimizes errors on popular sample sizes and accepts small errors between those sizes. Further refinements in software calibration can be envisioned.

Figure 15:
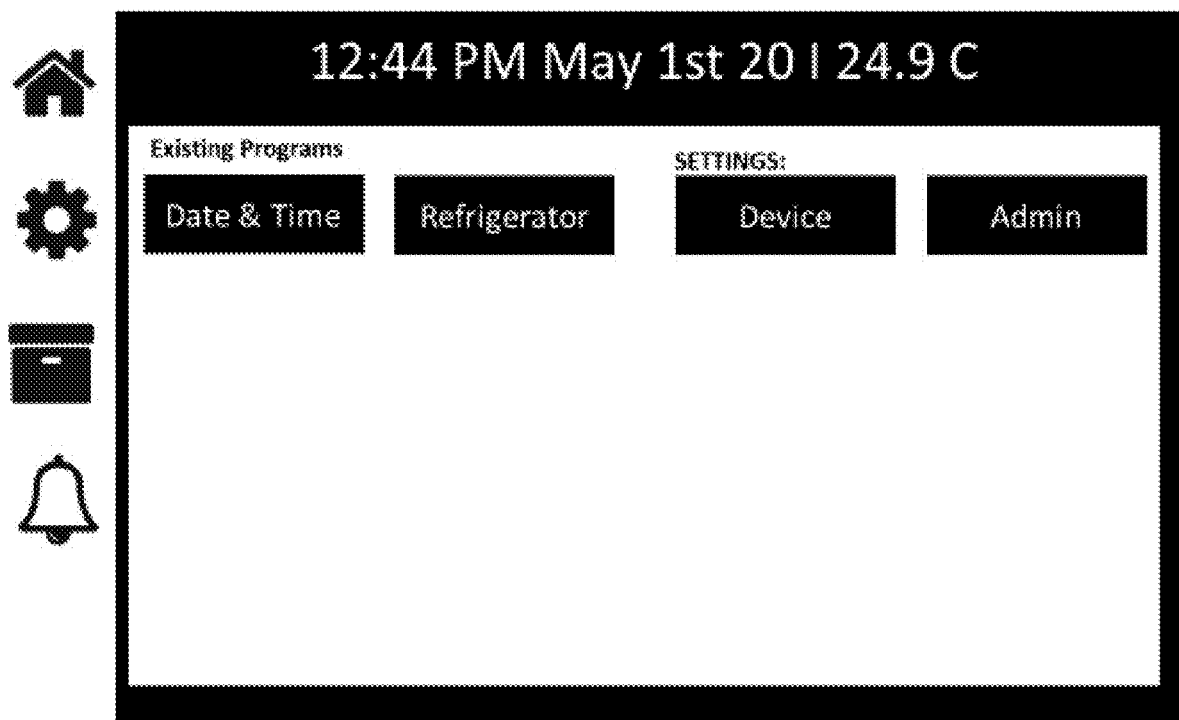
FIGS. 15-38 are sample setting screens of the present invention.
Figure 16:
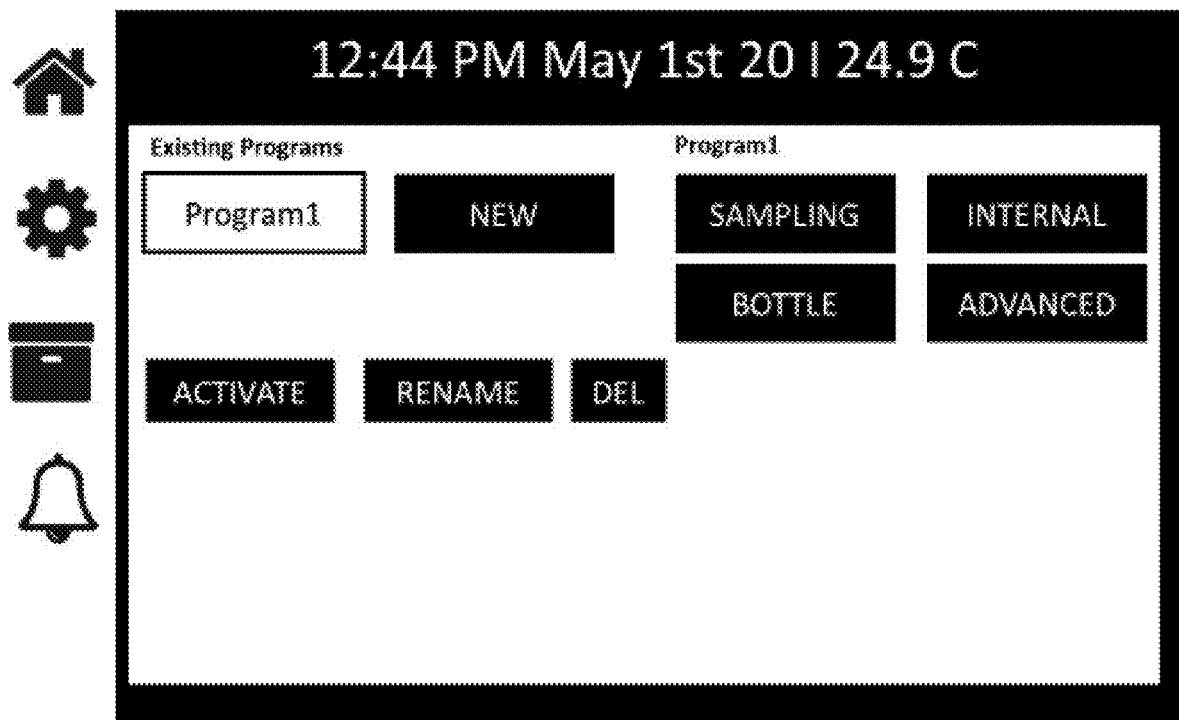

Referring to FIGS. 15-38, configuration of the sampling program is indicated. To customize a sampling program, the home screen initially displays "IDLE PROGRAM". Selection of the configuration icon 104 on the left side of the screen advances the system to an "EXISTING PROGRAMS" screen (FIG. 15). To change or create a program, either "Program 1" or "NEW" may be selected (FIG. 16). When "Program1" or "NEW" is selected, the screen changes to allow access and change four settings of the program: "SAMPLING, INTERVAL, BOTTLE, & ADVANCED" (FIG. 16). To build a new program, "NEW" is selected, the same screen will be displayed but with the "NEW" button highlighted. To continue making changes or building a new program one of the aforementioned settings may be selected. All "Settings" may be accessed and changed from the same screen.

Figure 17:
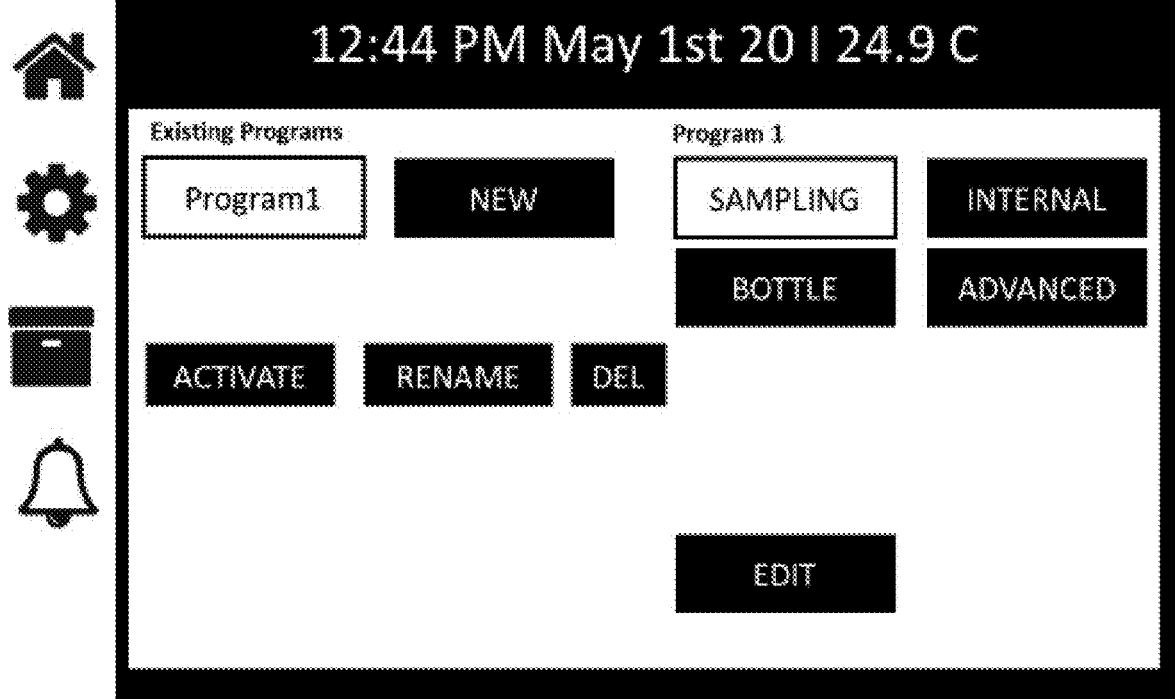
Figure 18:
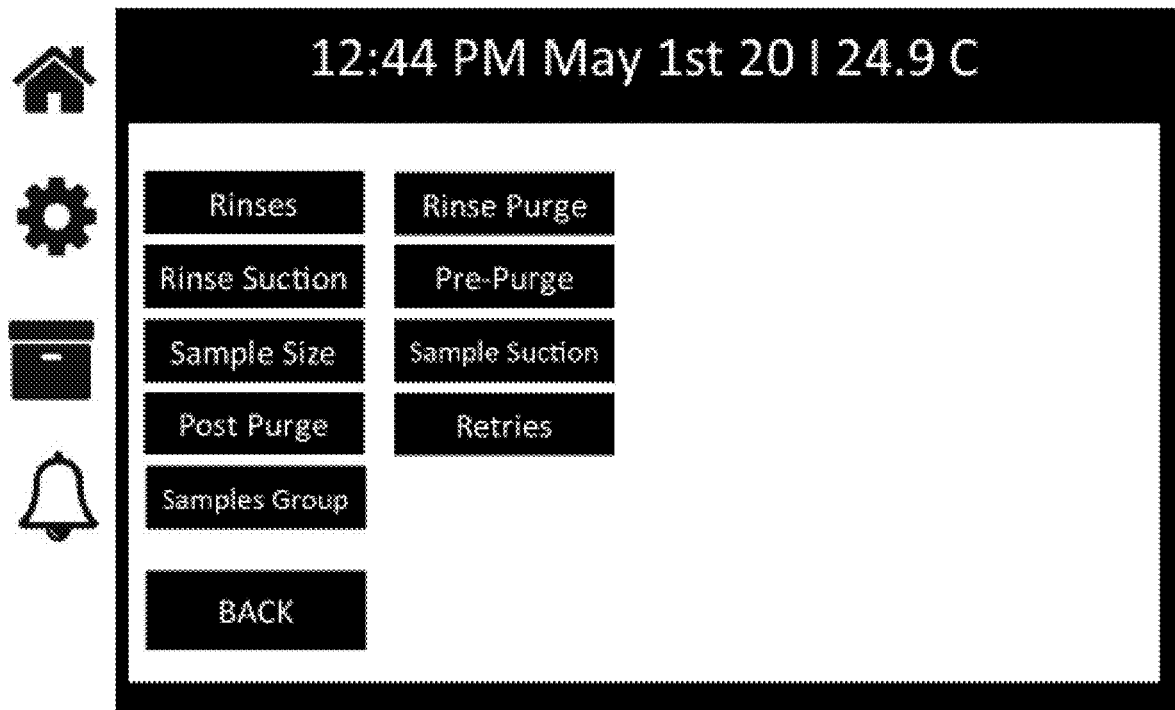

To change the settings of a program, the "SAMPLING" button may be selected, which turns is highlighted and the "EDIT" button is displayed (FIG. 17). Selection of the "EDIT" button to displays the settings of the sampling parameters (FIG. 18). The Sampling settings include: Rinses, Rinse Purge, Rinse Suction, Pre-Purge, Sample Size, Sample Suction, Post Purge, Retries and Samples Group (FIG. 18).

Figure 19:
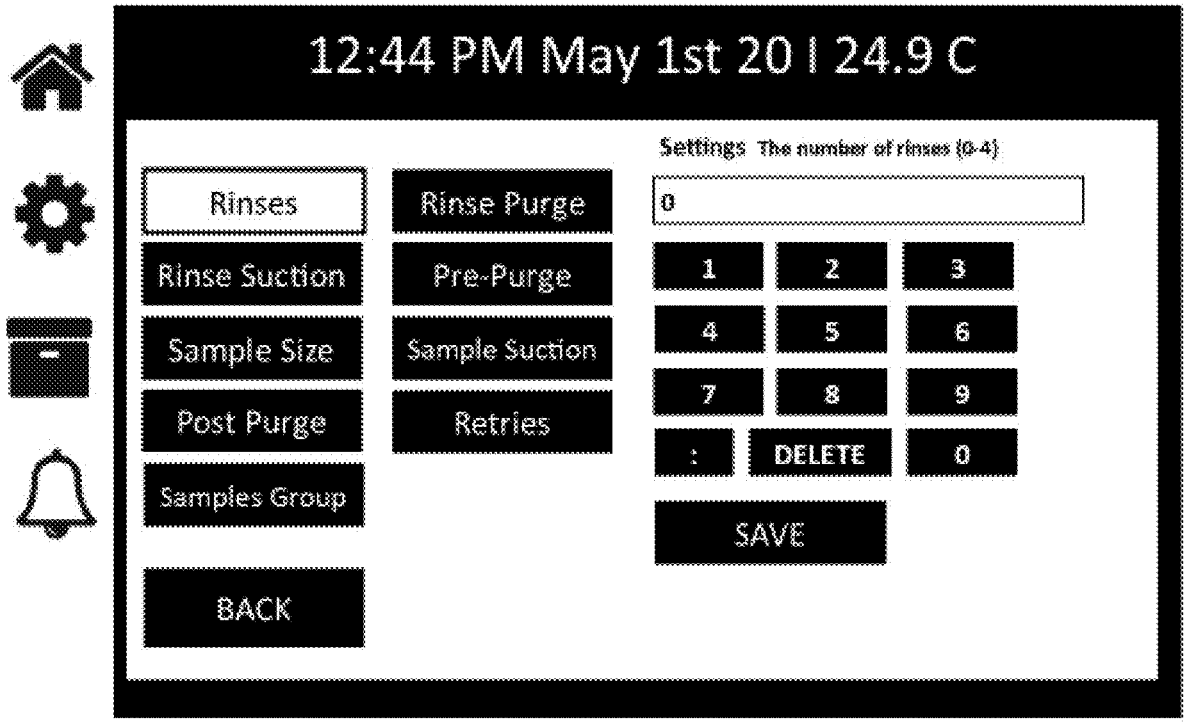

The Rinses setting is the number of times the sampler will rinse the sample line prior to pulling each sample. The rinse cycle will purge the sample line then pull liquid up the sample line, but not into the sample chamber. This may be done a number of times. Pressing the "Rinses" button displays the numeric entry keys used to enter the number of rinses in the window (FIG. 19). A numeric value from 1-4, for example, may be entered to rinse the sample line prior to pulling the actual sample. To skip rinsing the line first, 0 may be entered. When 0 is selected the Rinse Purge and Rinse Suction settings may be grayed out. Entering a numeric value will activate the Rinse Purge and Rinse Suction settings and they will no longer be grayed out.

Figure 20:
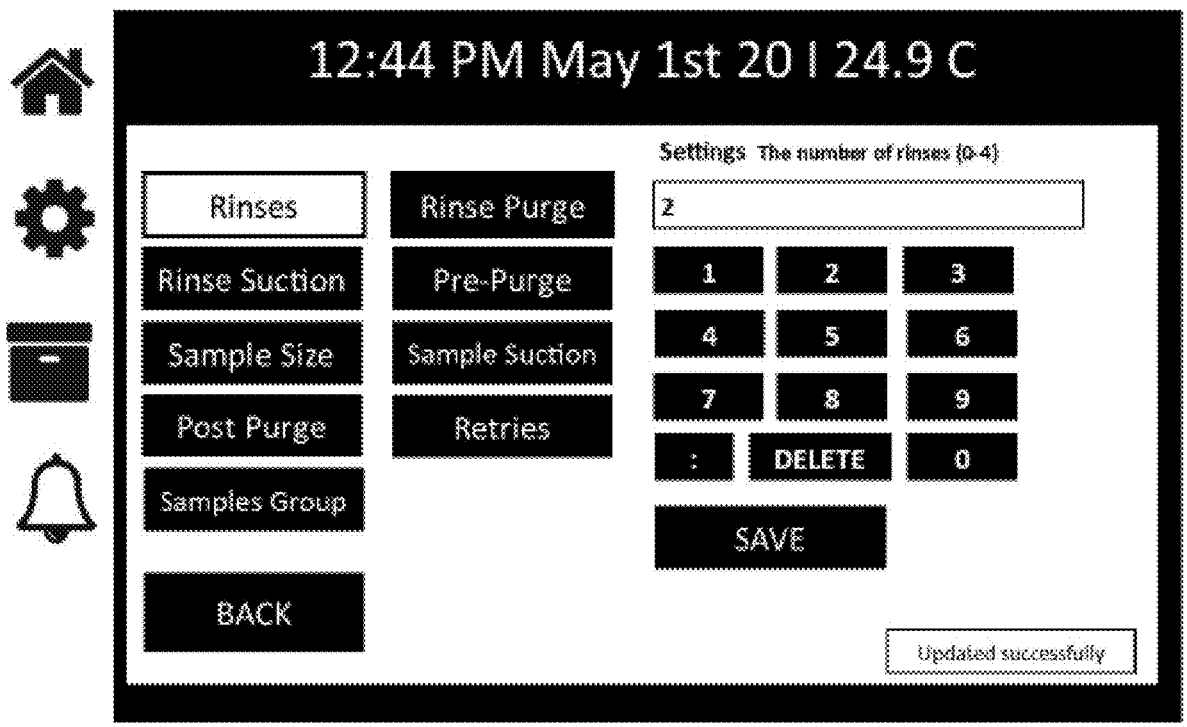

After entering a value and selecting Save, and "Updated Successfully" will appear in the lower right-hand corner if the value is accepted (FIG. 20). Other settings may be changed or added under the Sampling Settings by selecting and saving the entries.

Figure 21:
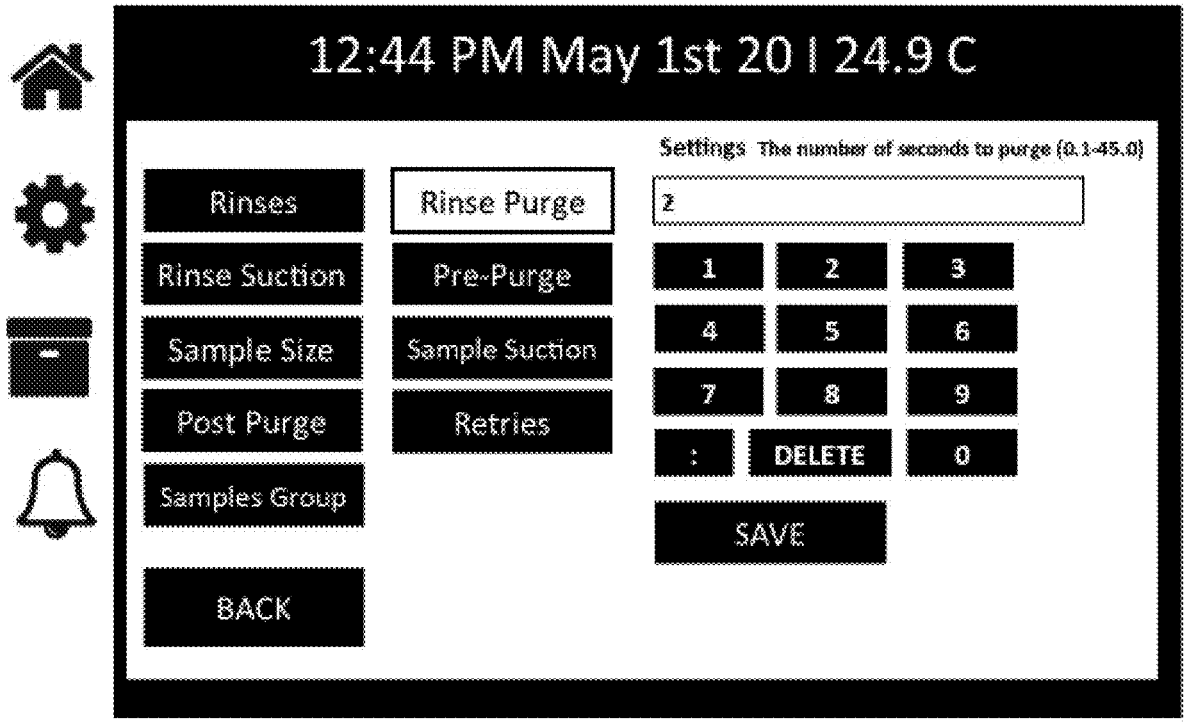
Figure 22:
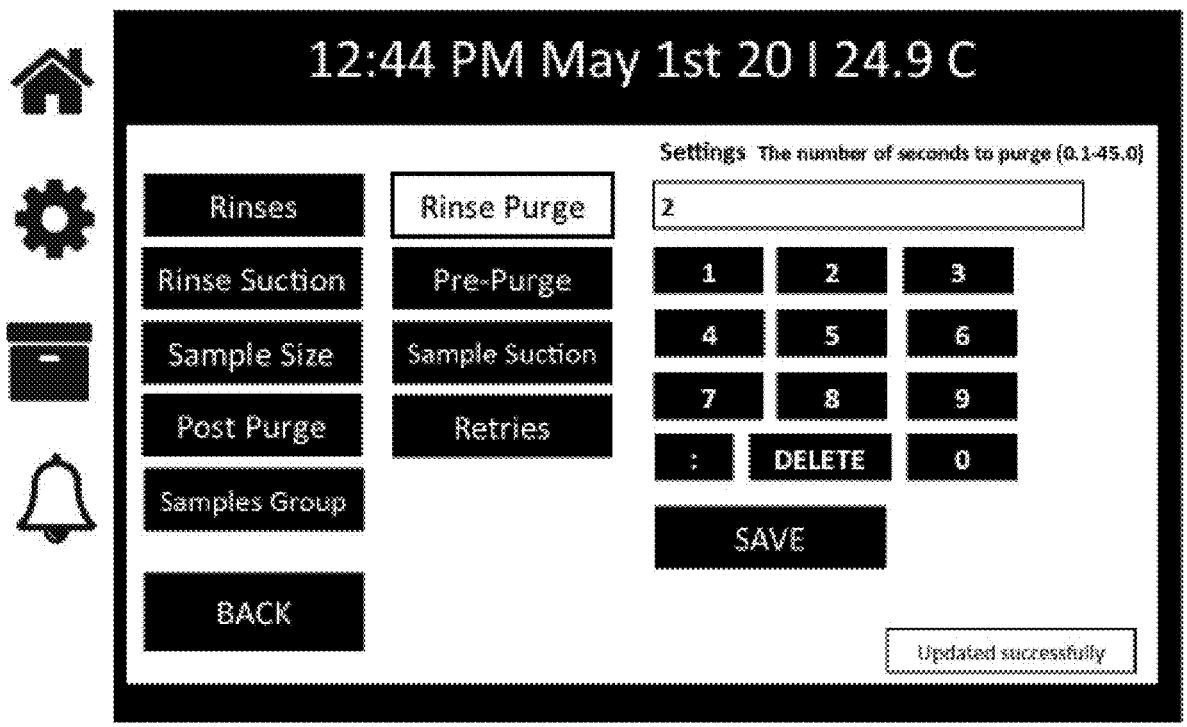

The Rinse Purge setting is the amount of time it takes to purge the sample line prior to pulling the rinse liquid into it (FIG. 21). The range of time may be set from 0.1 to 45.0 seconds. Selecting "Rinse Purge" button displays the numeric entry keys to enter the amount of time in the window under "SETTINGS". After entering the amount of time to purge the line, press Save, and "Updated Successfully" will appear in the lower right-hand corner if the time is accepted (FIG. 22).

Figure 23:
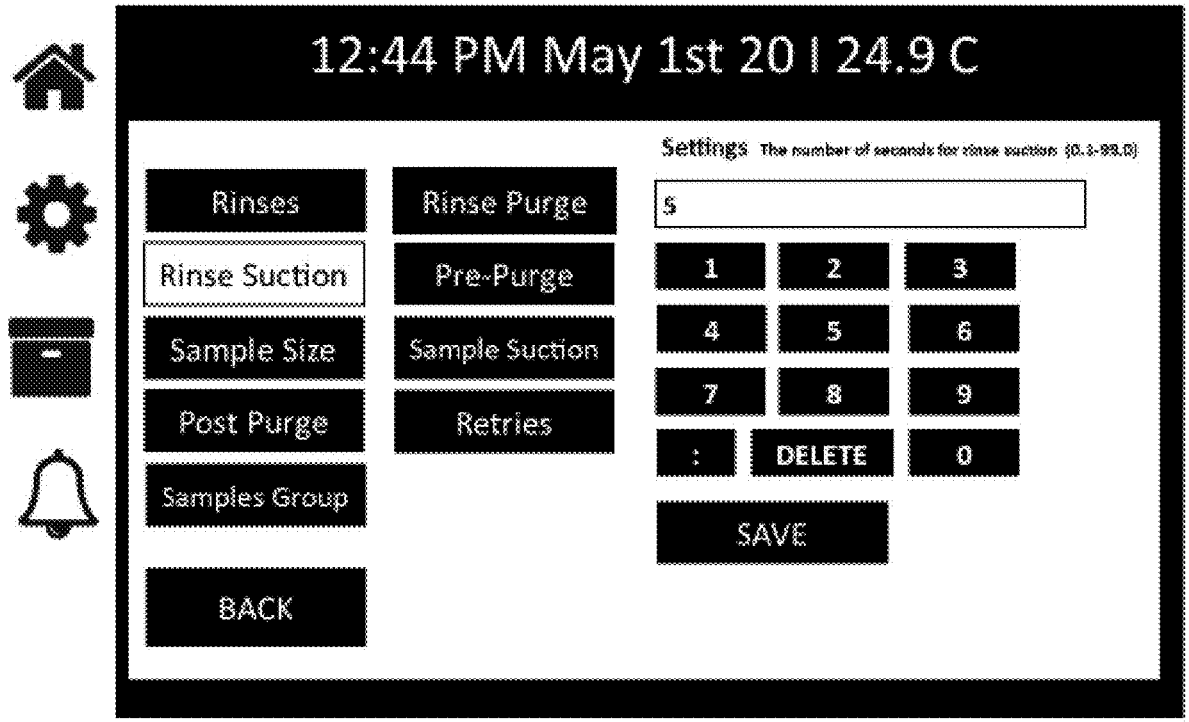
Figure 24:
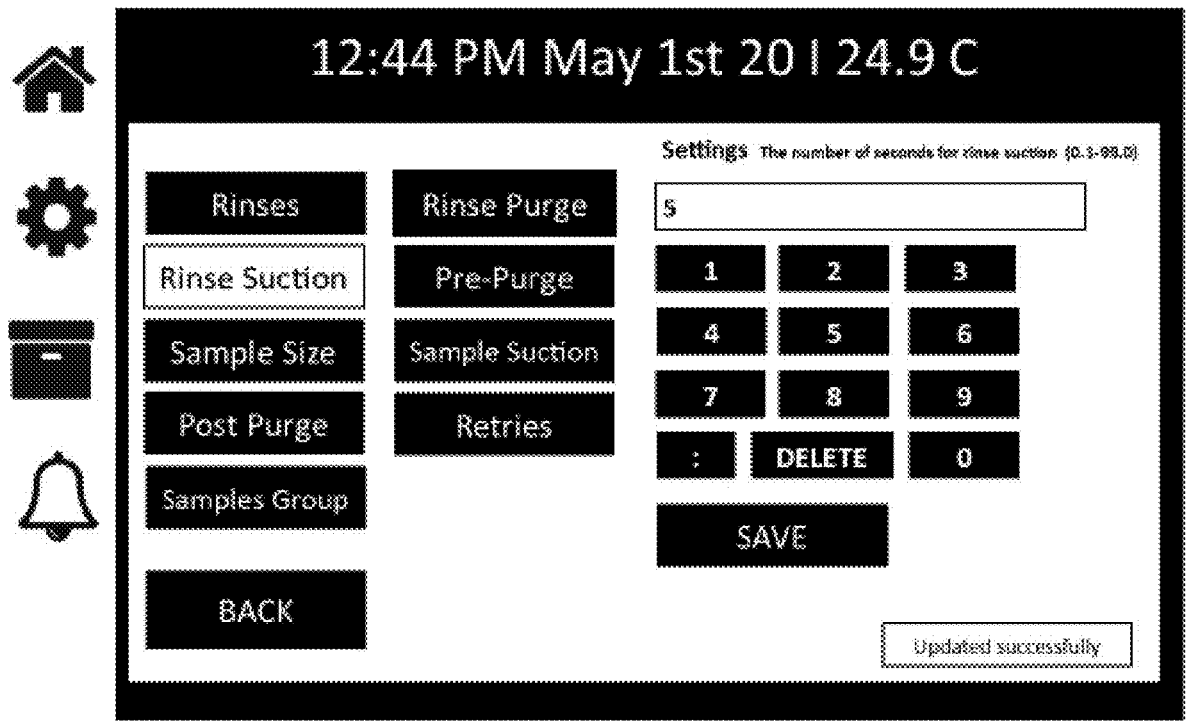

The Rinse Suction setting is the amount of Vacuum Time needed to pull the rinse liquid up to the sampler, but preferably not into it. Selecting the "Rinse Suction" button provides access to the numeric entry keys used to enter the amount of time in the window under "SETTINGS" (FIG. 23). After entering the amount of Vacuum time to rinse the line, press Save, and "Updated Successfully" will appear in the lower right-hand corner if the value is accepted (FIG. 24).

Figure 25:
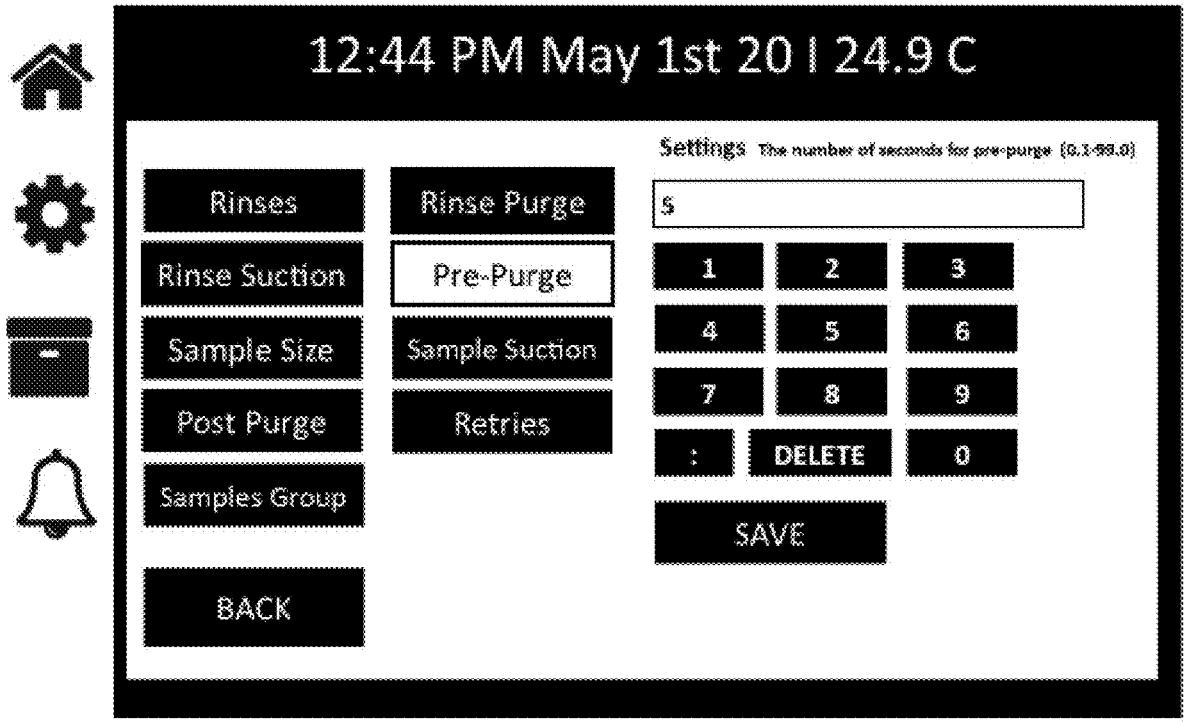
Figure 26:
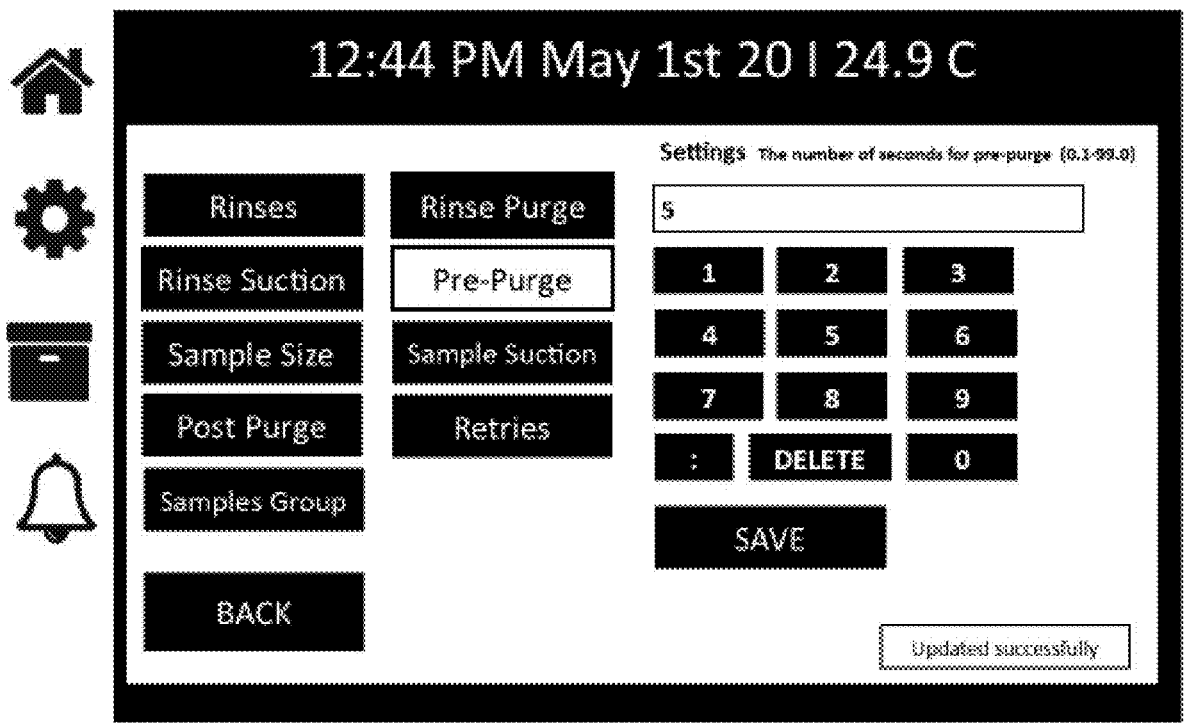

The Pre-Purge setting is the amount of time to purge the sample line/suction strainer prior to pulling the sample. Selecting the "Pre-Purge" button provides access to the numeric entry keys used to enter the amount of time in the window under "SETTINGS" (FIG. 25). The amount of time allowed is from 0.1-99.0 seconds. Purging the sample line before the sample is taken is preferred to achieve a represented sample. After entering an amount of time and selecting Save, "Updated Successfully" will appear in the lower right-hand corner if the value is accepted (FIG. 26).

Figure 27:
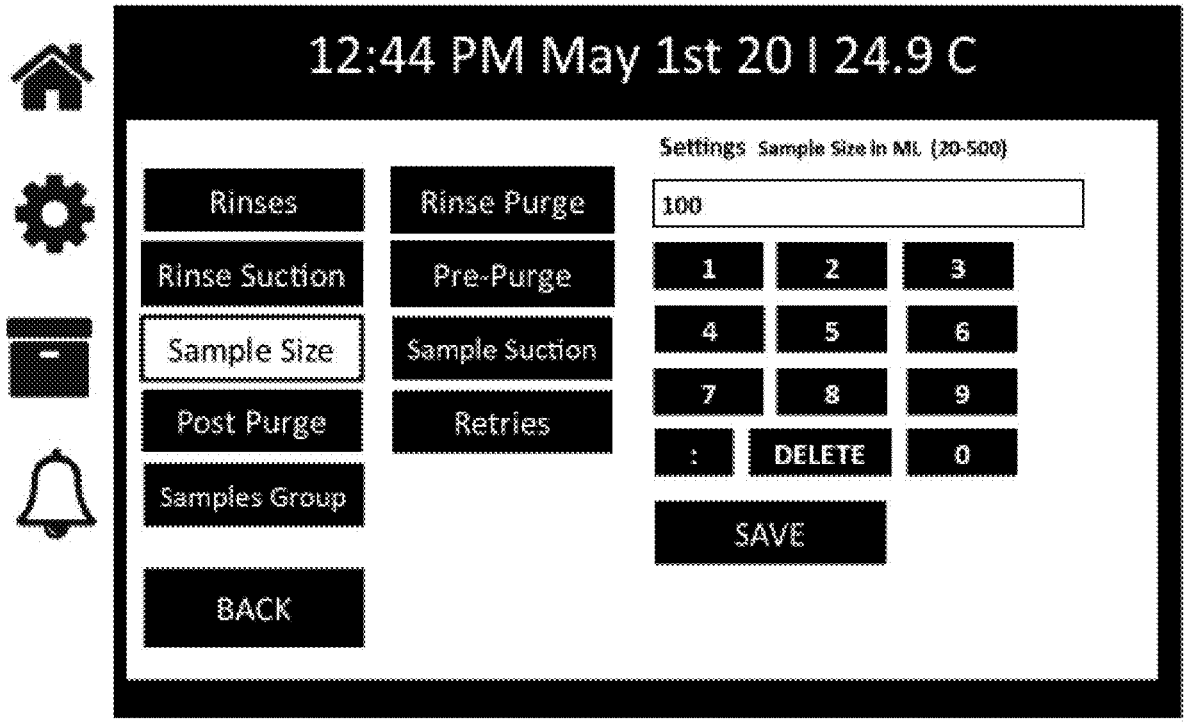
Figure 28:
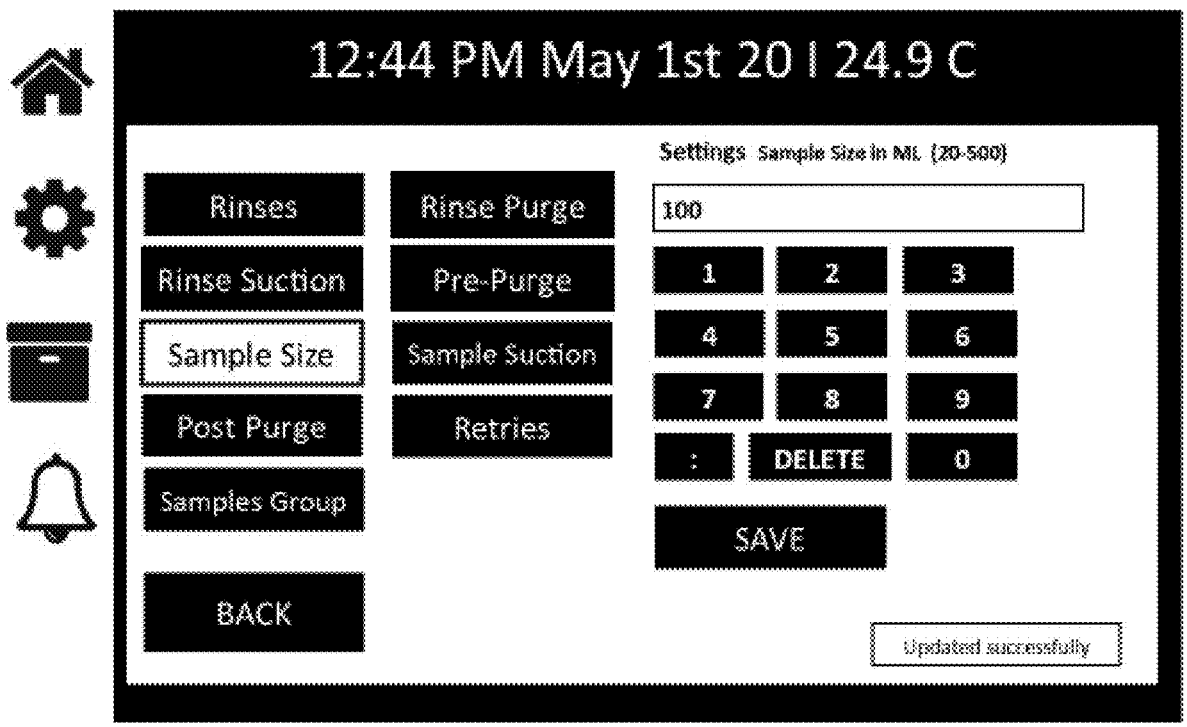

The Sample Size setting is the volume of sample to be measured and added to the sample container (FIG. 27). Selecting the "Sample Size" button provides access to the numeric entry keys used to enter the size of rinses in the window under "SETTINGS", in the range from 20-500 ml. After entering the desired Sample Size, press Save, and "Updated Successfully" appears in the lower right-hand corner if the value is accepted (FIG. 28).

Figure 29:
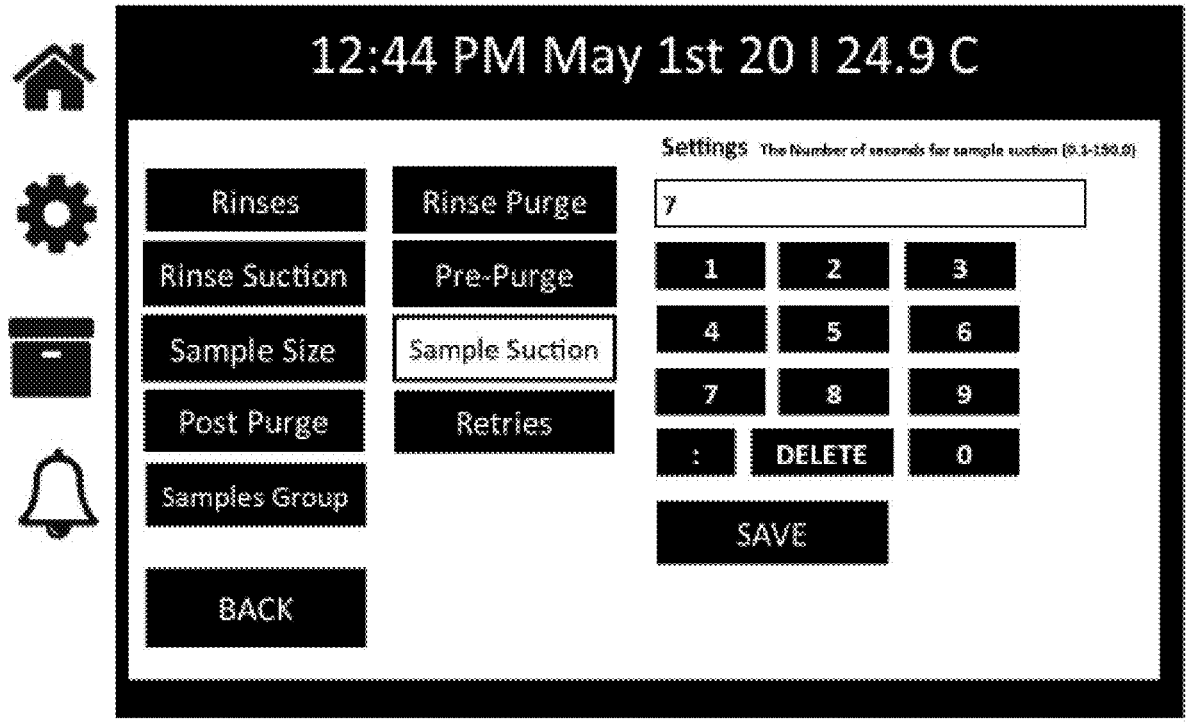
Figure 30:
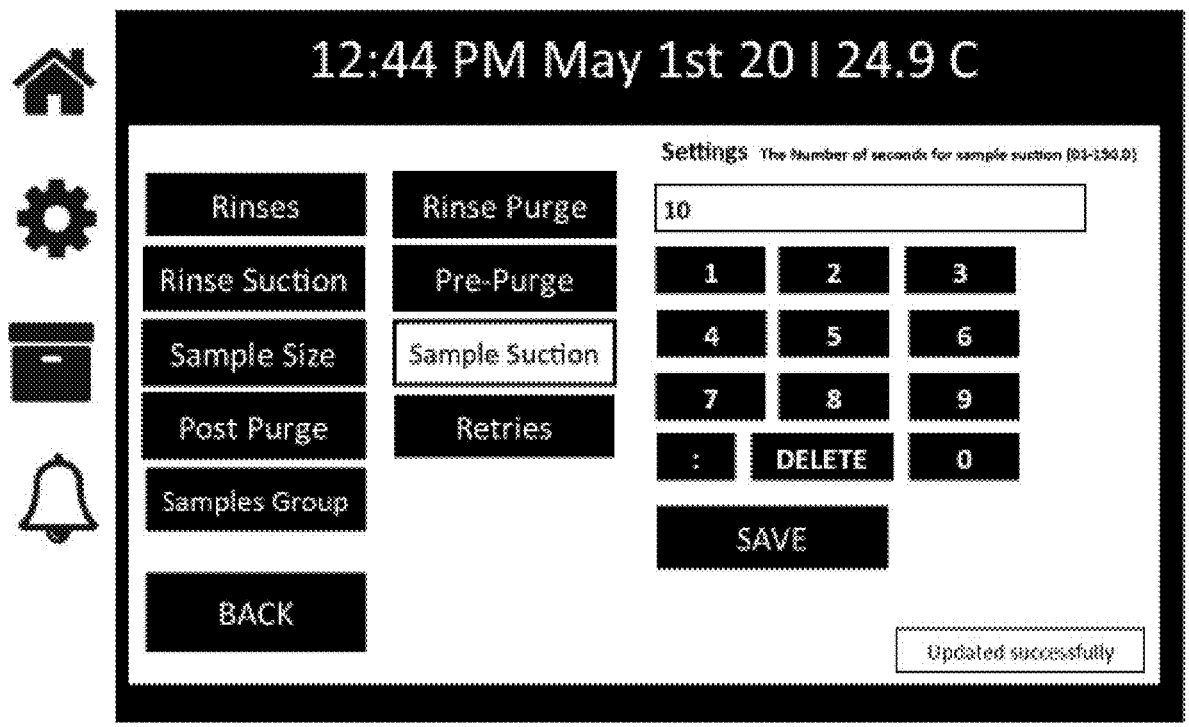

The Sample Suction setting is the amount of Vacuum Time needed to pull the desired sample into the sample chamber for collection (FIG. 29). Selecting the "Sample Suction" button provides access to the numeric entry keys used to enter the amount of time in the window under "SETTINGS". The amount of time may be entered from 0.1-150 seconds. After entering the time, press Save, and "Updated Successfully" will appear in the lower right-hand corner if the value is accepted (FIG. 30).

Figure 31:
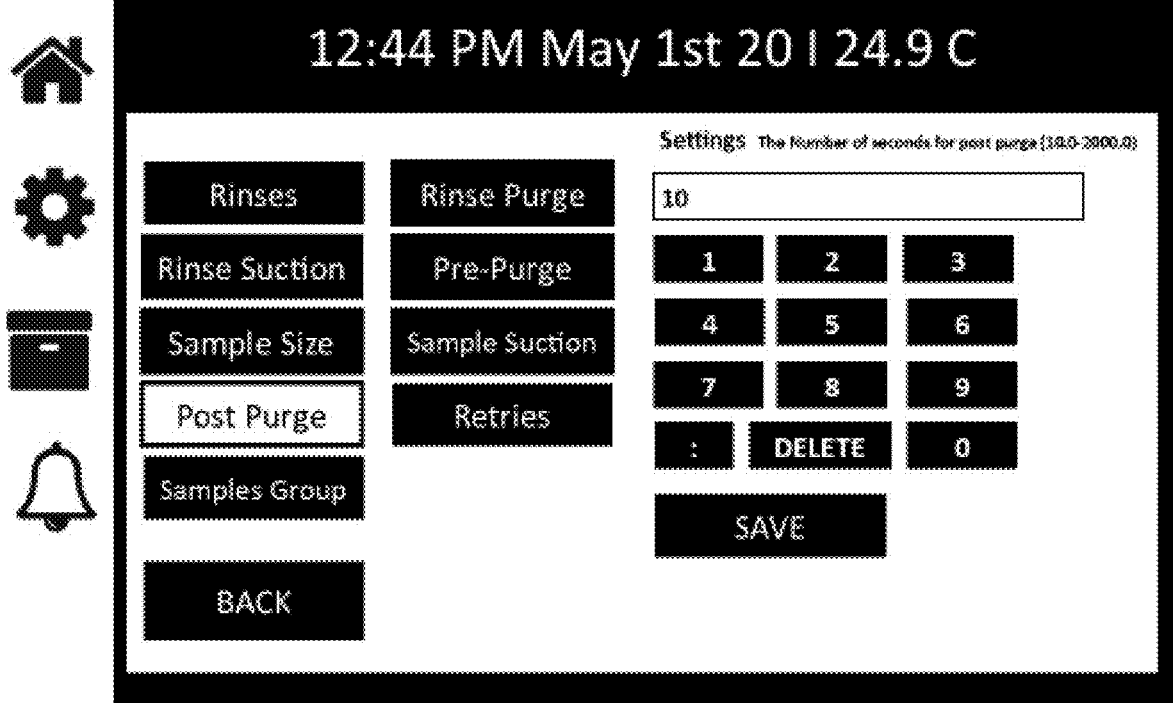
Figure 32:
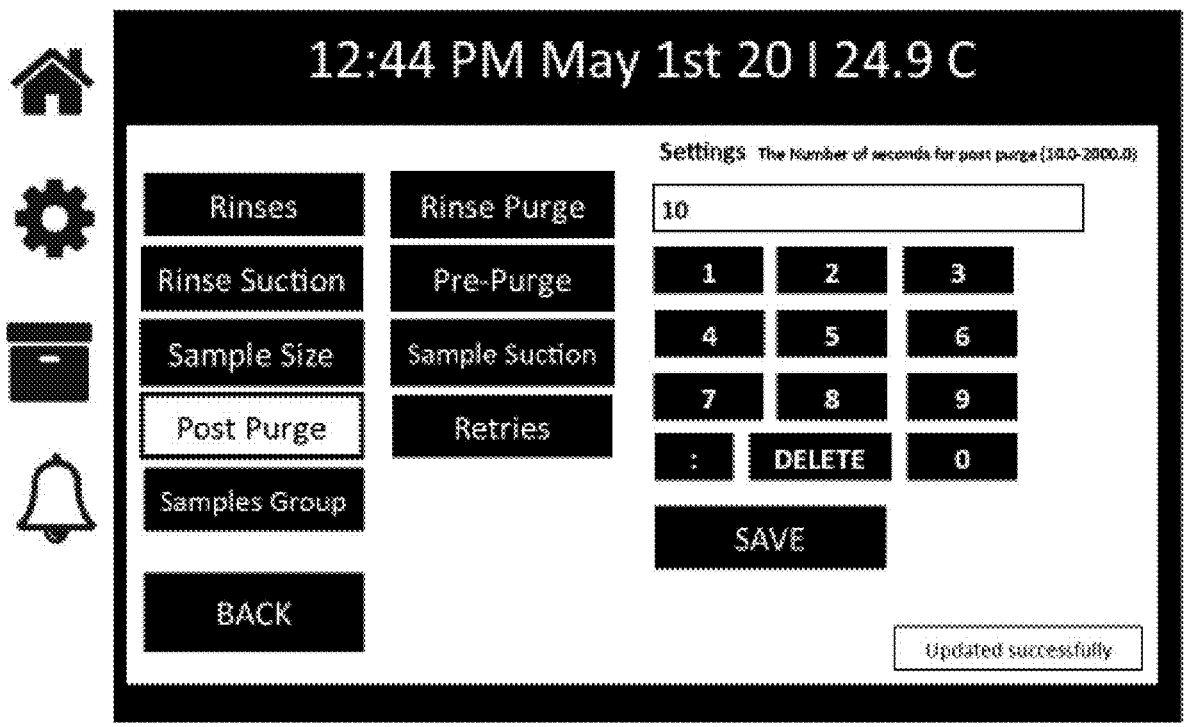

The Post Purge setting is the amount of time needed to clean the line out after the sample has been taken (FIG. 31). Select "Post Purge" to access the numeric entry keys used to enter the amount of time in the window under "SETTINGS". The range is from 10-200 seconds. After entering the time press Save, and "Updated Successfully" will appear in the lower right-hand corner if the value is accepted (FIG. 32).

Figure 33:
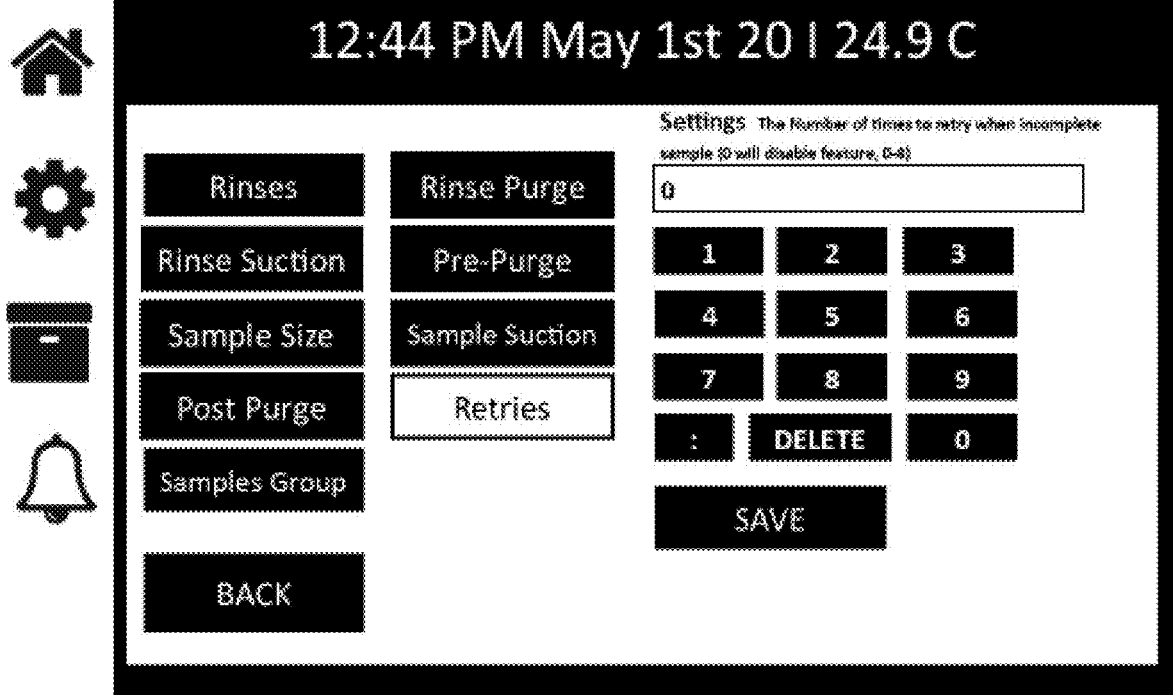
Figure 34:
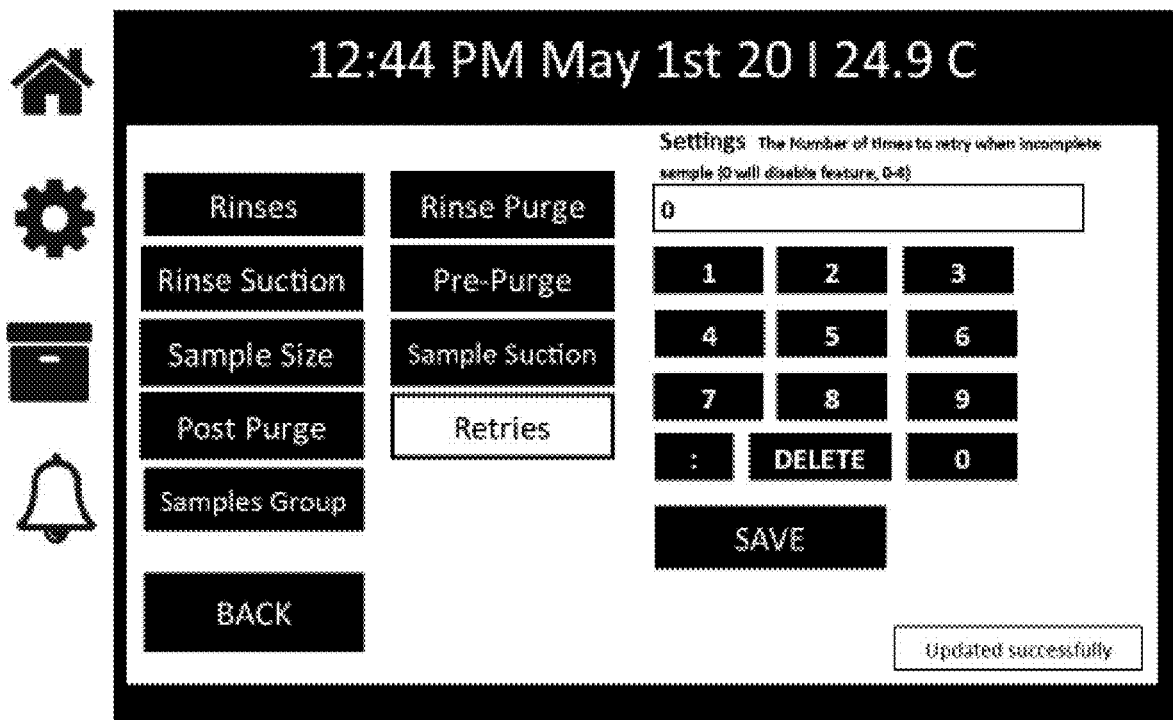

The Retries setting is the number of times the sampler will try to retake a sample if it fails to do so the first time (FIG. 33). This could be caused from the suction line being out of the water or not enough suction time or a partially plugged suction line. Selection of the "Retries" button provides to access the numeric entry keys used to enter the number of times in the window under "SETTINGS". The range may be from 0-4 or more times, for example. If zero is selected the setting is turned off. After entering the number of Retry times and pressing Save, the "Updated Successfully" will appear in the lower righthand corner if the value is accepted (FIG. 34).

Figure 35:
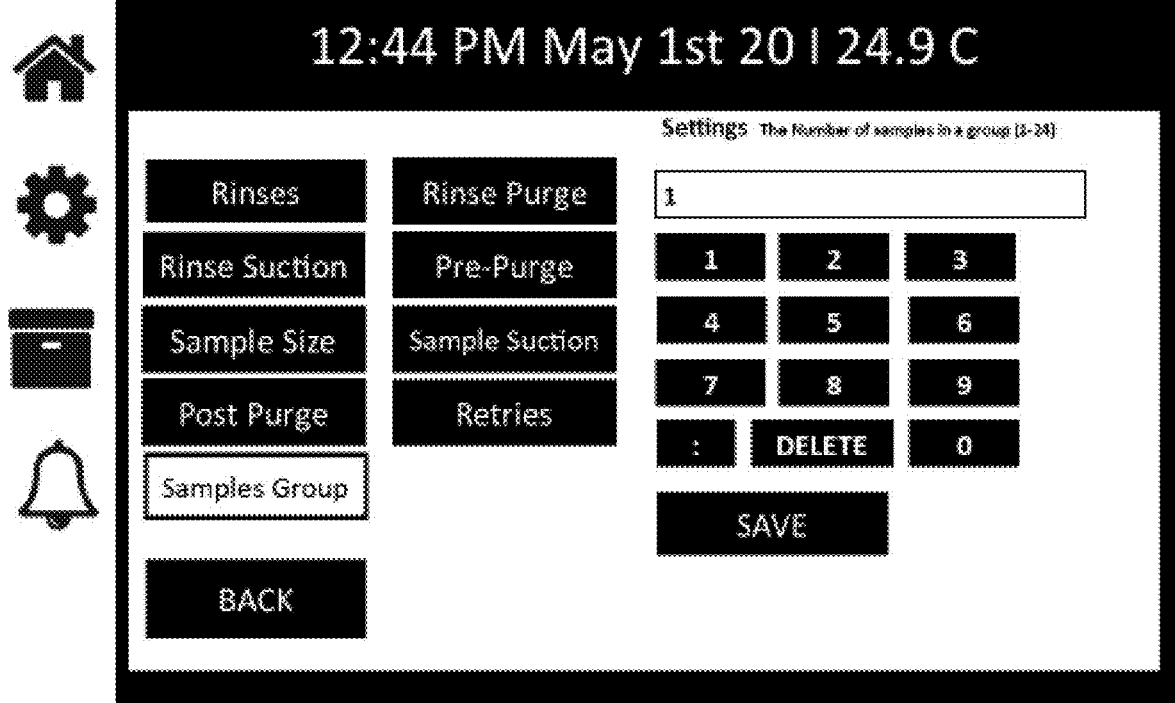
Figure 36:
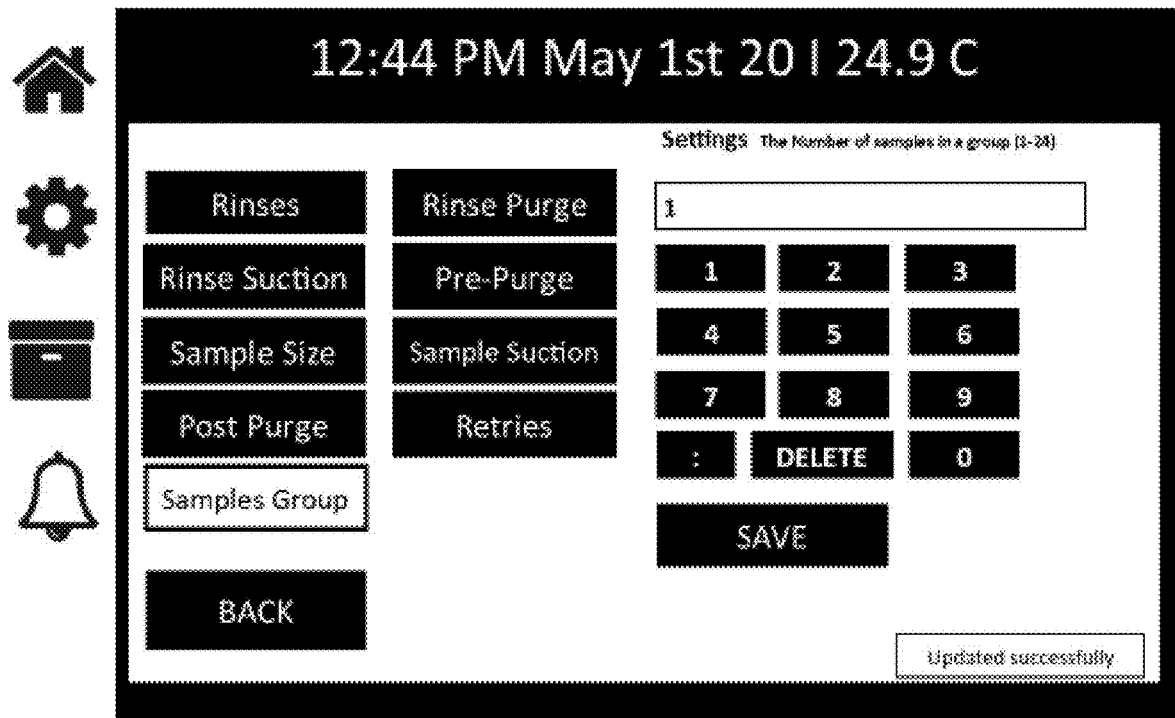

The Samples Group setting gives you the ability to collect samples larger than 500 ml (FIG. 35). By increasing the Sample group, the number of times the sampler is pulled will be repeated. For example, to pull 750 ml per sample, the sample size may be set to 250 and the Sample Groups set to 3. Press the "Samples Group" button to access the numeric entry keys used to enter the number of samples in the window under "SETTINGS". The range may be from 1-24, for example. After entering the numeric value press Save, and "Updated Successfully" will appear in the lower right-hand corner if the value is accepted (FIG. 36).

Figure 37:
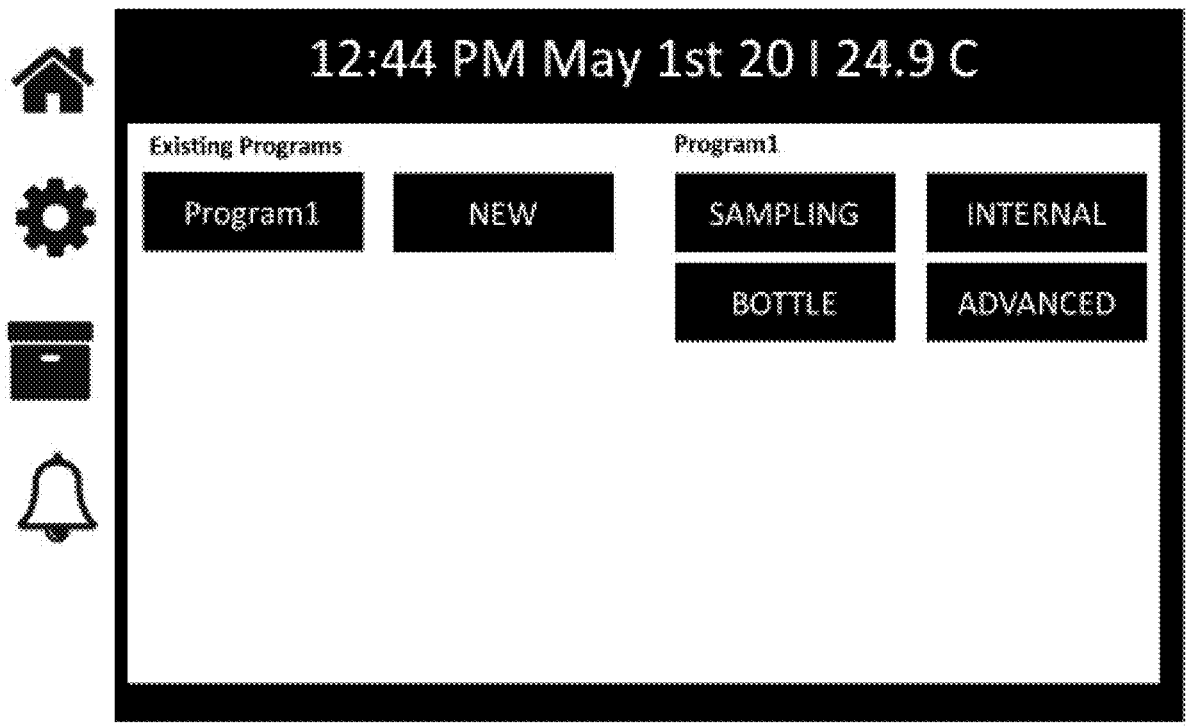
Figure 38:

If more program changes are needed after you have saved your changes, press the "BACK" button to take you back to the "EXISTING PROGRAMS" screen. Then select the next item requiring changes such as Interval, Bottle, or Advanced (FIG. 37). If all the program changes are complete, press the Home icon to view and verify the selections under their respective TAB. If all selections are correct press the "RUN" button when ready to sample. Any time the programming is complete press the Home icon to return to the Home screen (FIG. 38).

The "INTERVAL" settings allow changes to the how the sample will be taken, such as Time, Max Flow, Flow Pulses, Flow 4-20, Link Bottle, Random Samples, Random Program, Random Min, Sample on Start, and External Input, for example.

Figure 39:
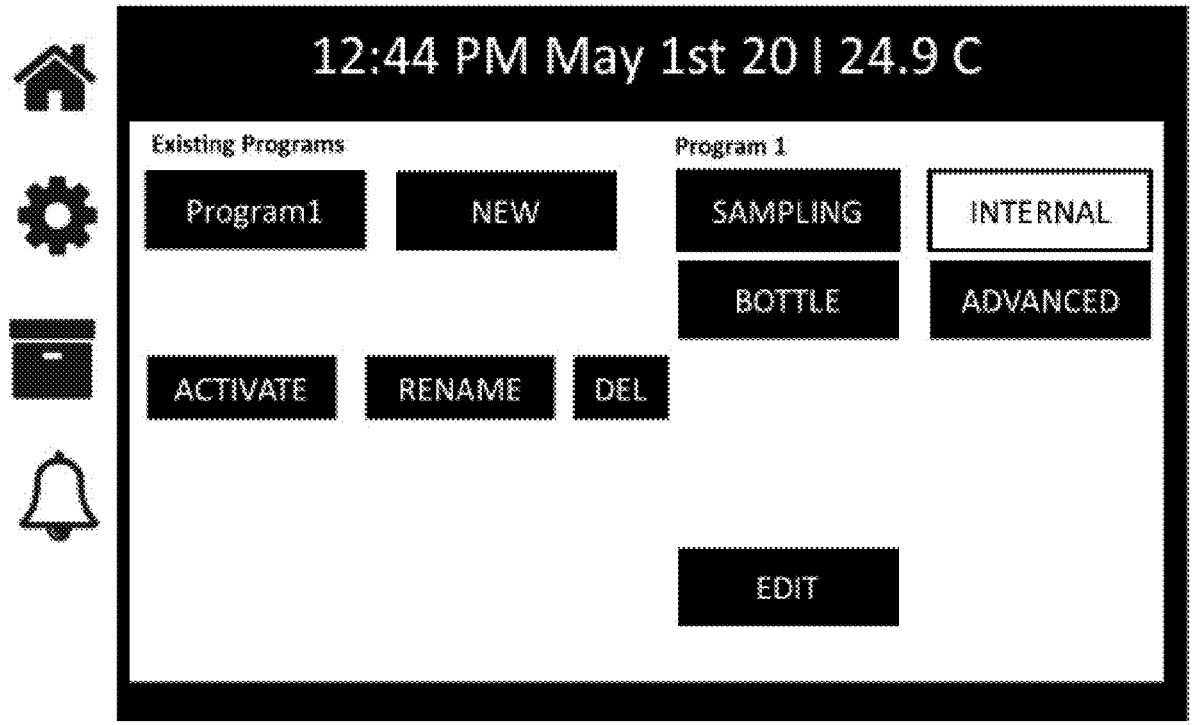
FIGS. 39-61 are interval setting screens of the present invention.
Figure 40:
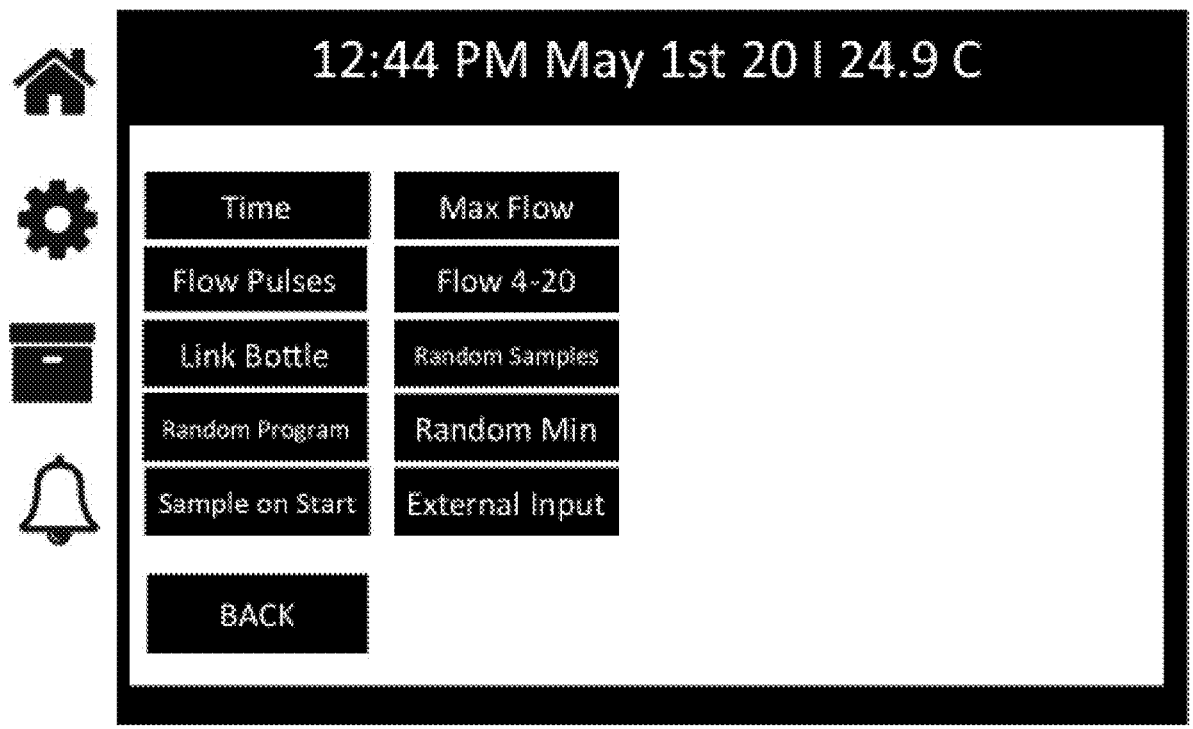

From the "EXISTING PROGRAMS" screen press the "INTERVAL" button and the "EDIT" button will appear on the screen (FIG. 39). Press the "EDIT" button to access to the INTERVAL settings screen (FIG. 40). On the main INTERVAL settings screen, choose from the settings listed above or select the "BACK" button to go to the previous screen. All "Settings" may be accessed and changed from the same screen. Just press the next button you want to make changes in.

Figure 41:
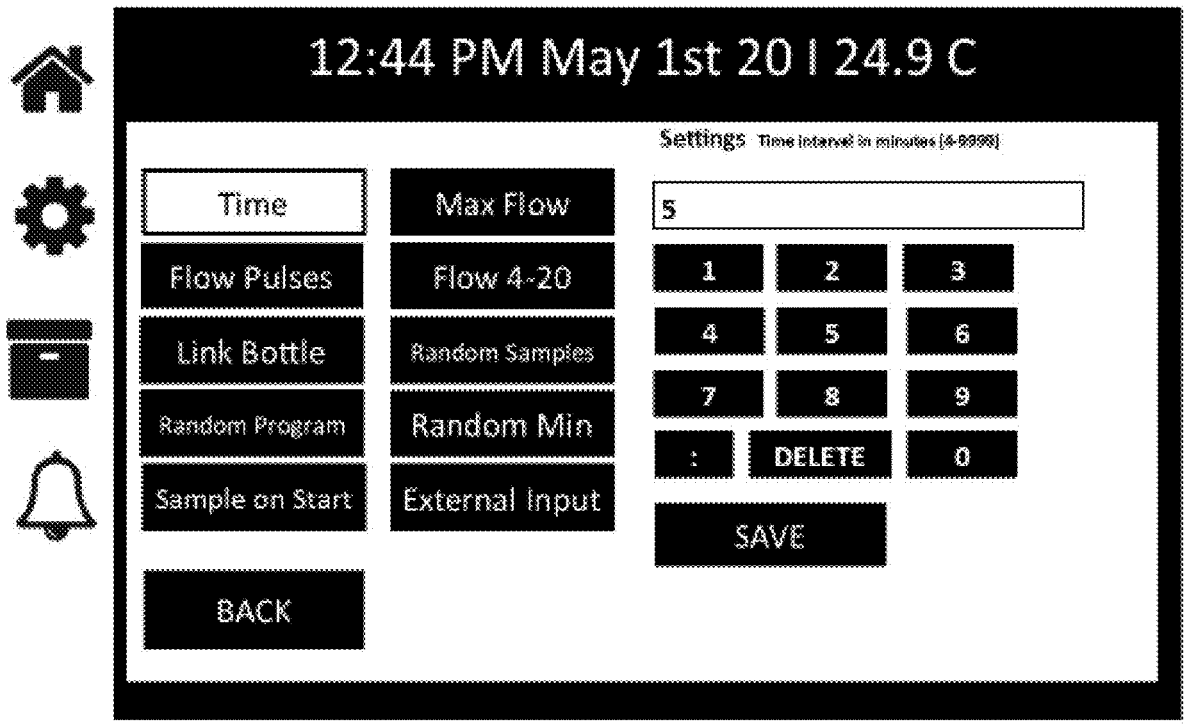
Figure 42:
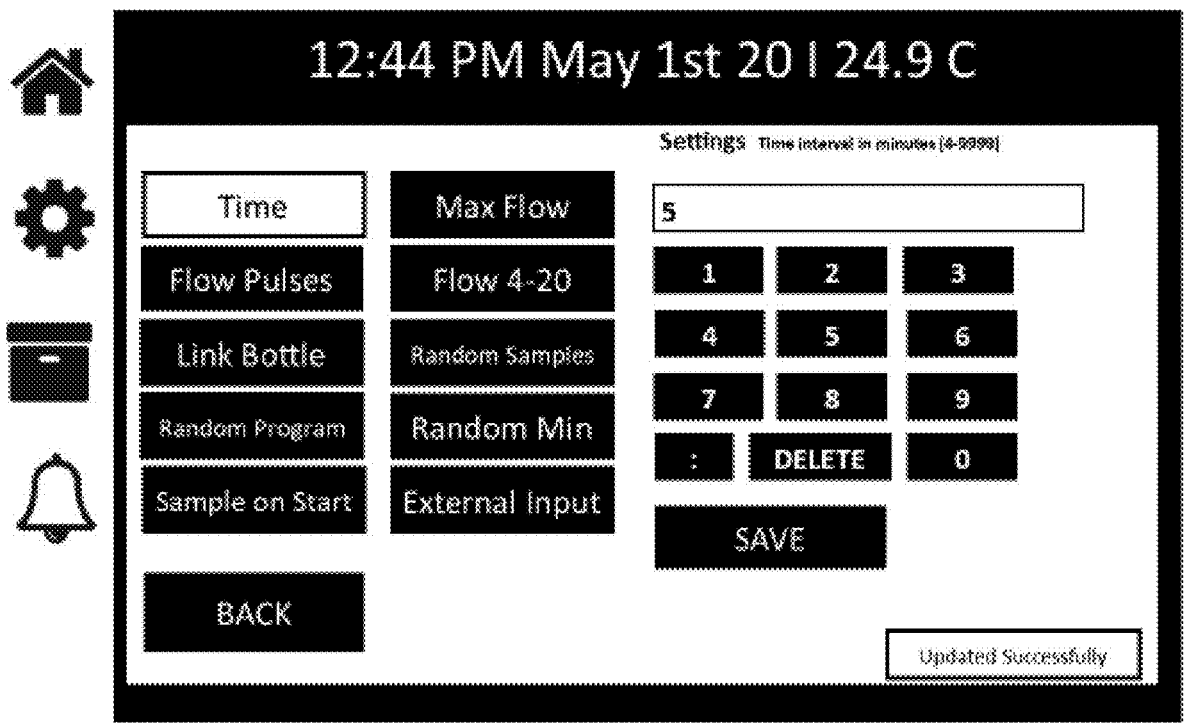

The Time setting is the interval of time that you want to have between each sample or how often you want the sample to be pulled (FIG. 41). Press the "Time" button to access the numeric entry keys used to enter the time in the window under "SETTINGS". The Time interval range is from 4-9999 minutes in between each sample, for example. After entering the time, press Save, and "Updated Successfully" will appear in the lower right-hand corner if the value is accepted (FIG. 42).

Figure 43:
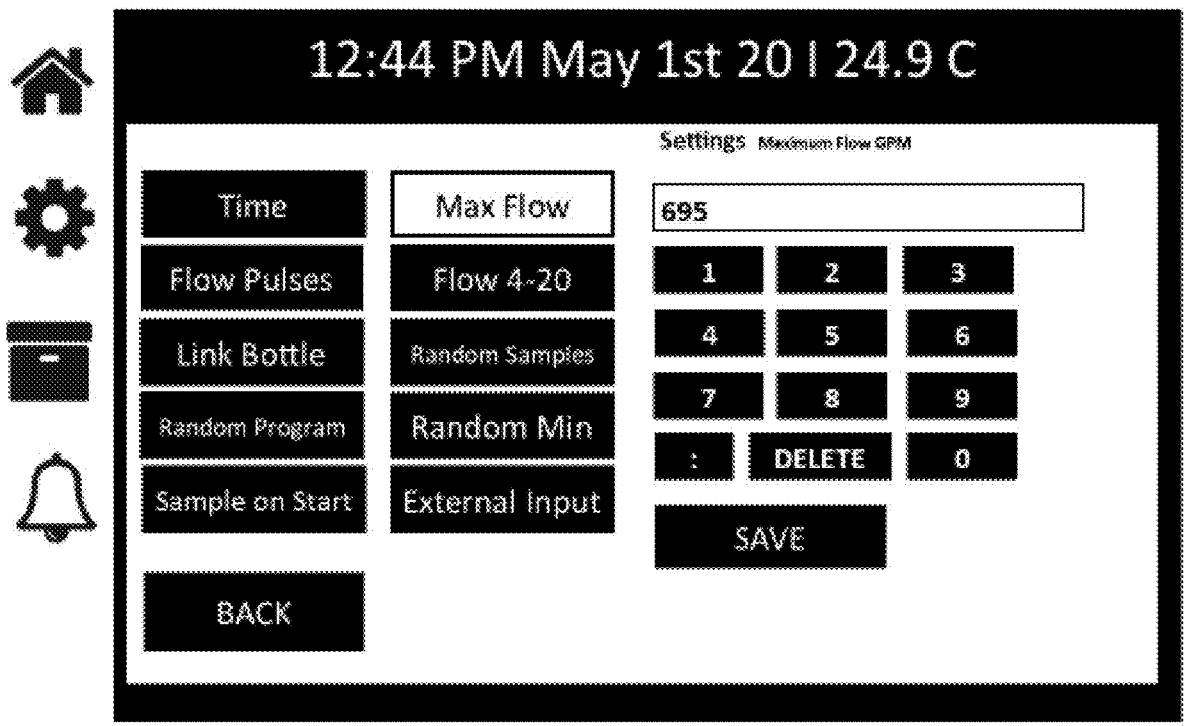
Figure 44:
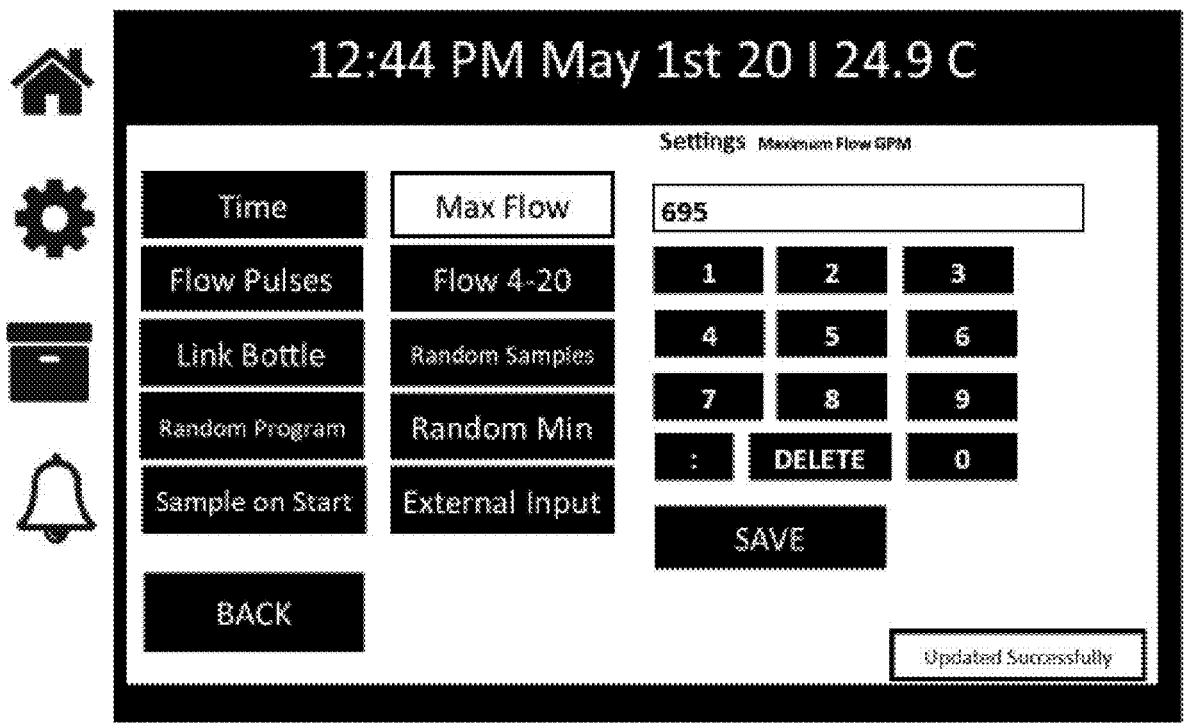

The Max Flow setting is based on Gallons Per Minute (GPM). The GPM is the maximum flow of the flowmeter scaling (FIG. 43). For example, if a flowmeter range is from 4-20, which equals 4 mA=0 GPM and 20 mA equals 695 GPM (1 Million gallons per day), then would be entered 695 in the numeric entry window. The sampler will determine the flow based on the sample information provided. Press the "Max Flow" button to access the numeric entry keys used to enter the size of sample in the window under "SETTINGS". Enter the Maximum Flow in GPM that the flowmeter mA signal represents. After entering the Maximum Flow, press Save, and "Updated Successfully" will appear in the lower right-hand corner if the value is accepted (FIG. 44).

Figure 45:
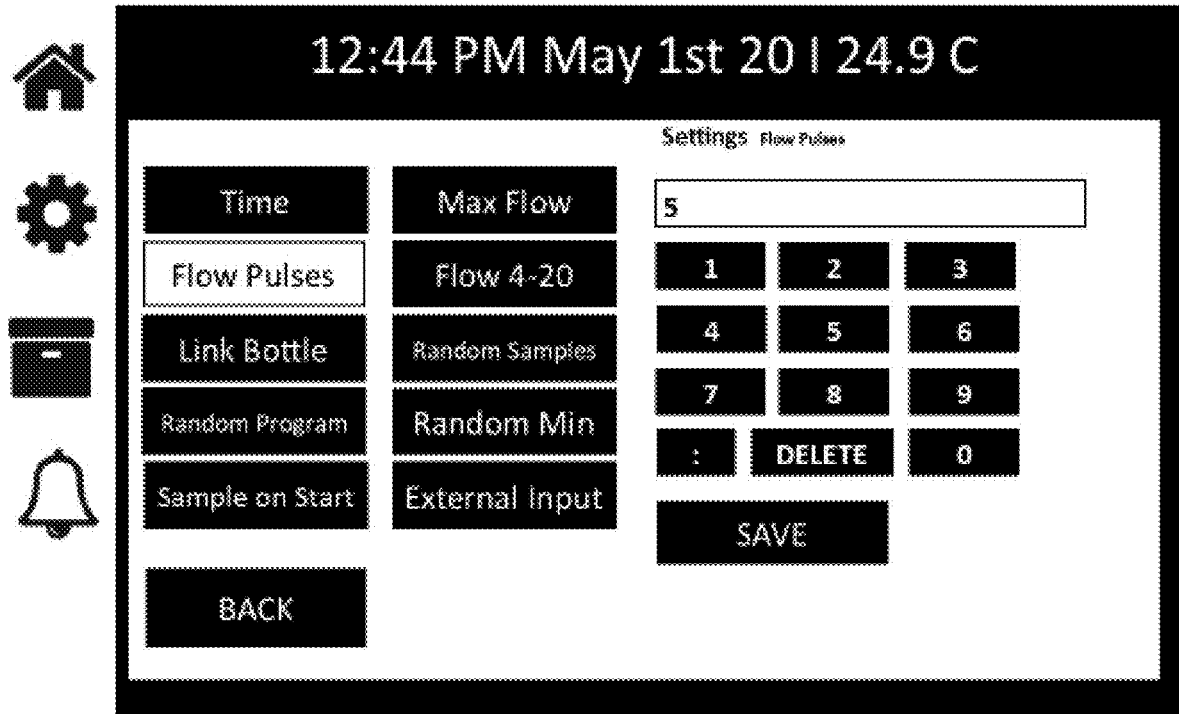
Figure 46:
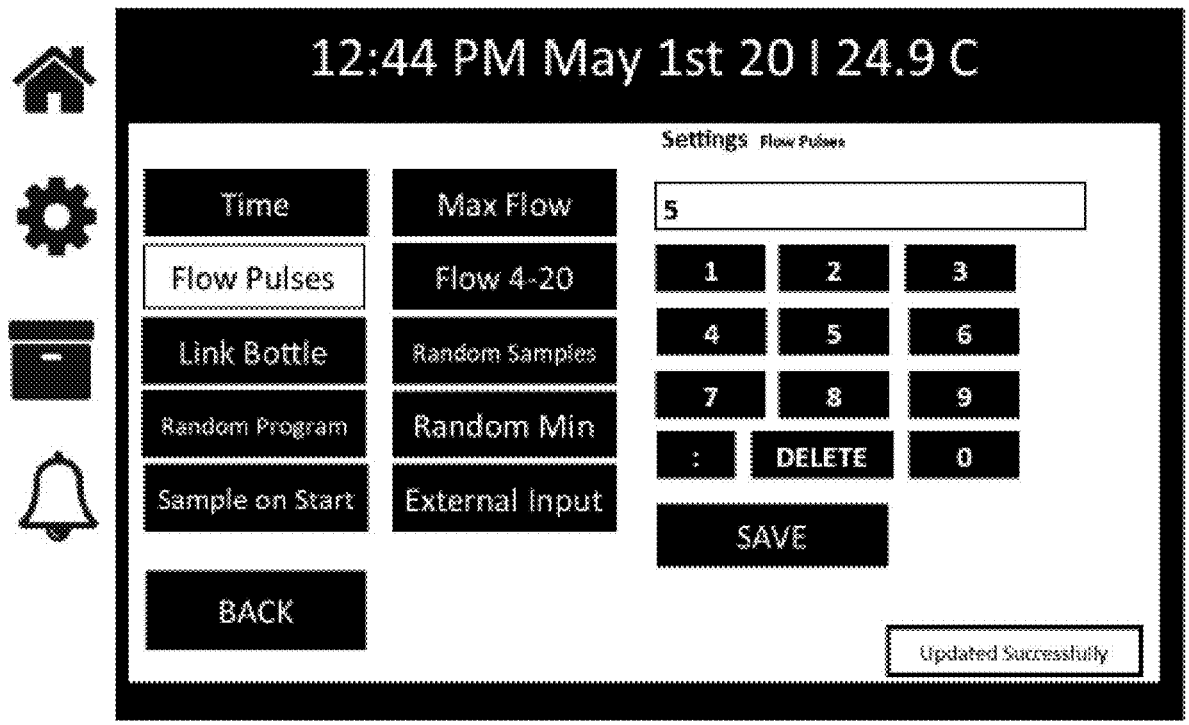

The Flow Pulses setting is the number of pulses to receive before the sampler pulls a sample (FIG. 45). For example, if the flowmeter produces a pulse every 1,000 gallons and a sample is desired every 5,000 gallons, 5,000÷1,000=5 flow pulses. Press the "Flow Pulses" button to access the numeric entry keys used to enter the number of pulses in the window under "SETTINGS". After entering the numeric value, press Save, and "Updated Successfully" will appear in the lower right-hand corner if the value is accepted (FIG. 46).

Figure 47:
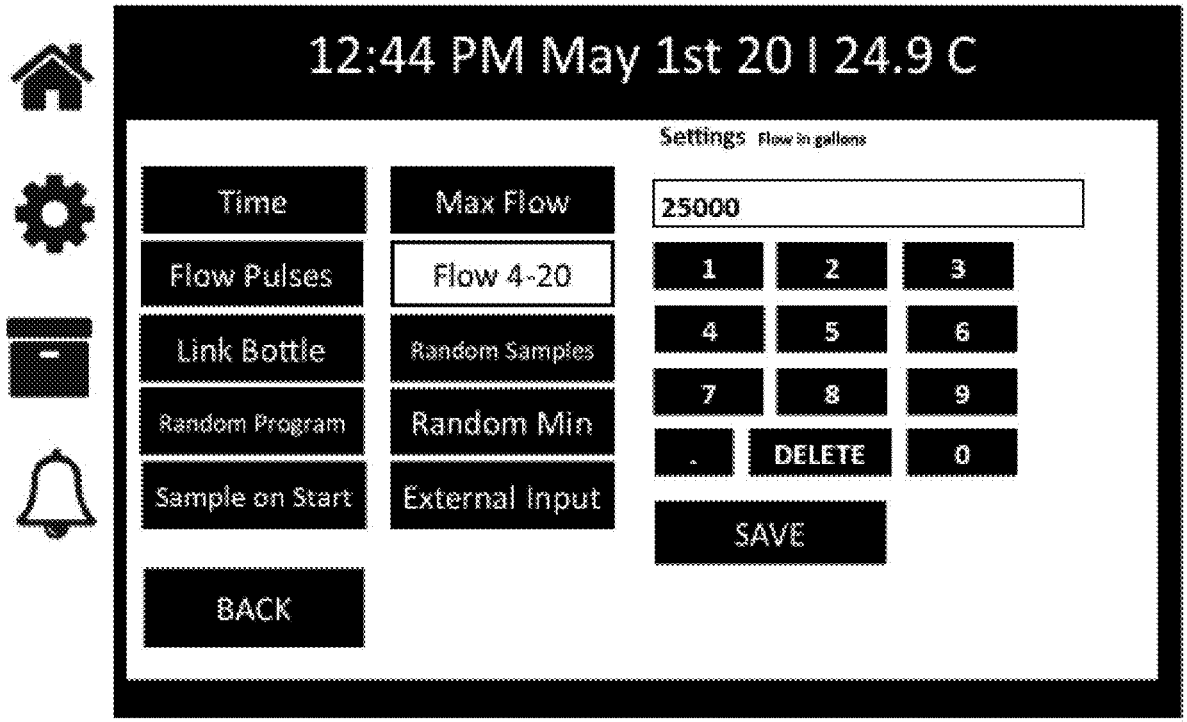
Figure 48:
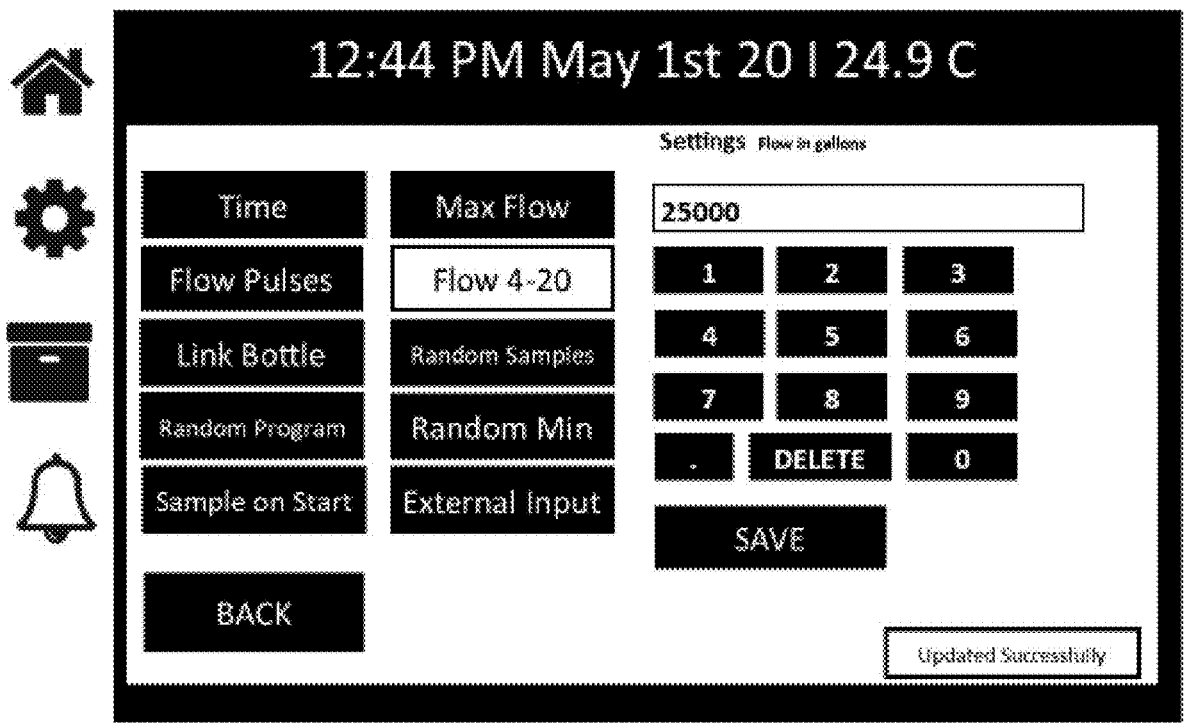

The Flow 4-20 setting is used to set the sample rate in gallons between samples (FIG. 47). This setting is used in conjunction with Max Flow above. Enter the gallons between samples. For example, to take a sample every 2500 gallons based on flow, enter 2500. Press the "Flow 4-20" button to access the numeric entry keys used to enter the rate in the window under "SETTINGS". The range is from 4-20, for example. After entering the numeric value, press Save, and "Updated Successfully" will appear in the lower right-hand corner if the value is accepted (FIG. 48).

Figure 49:
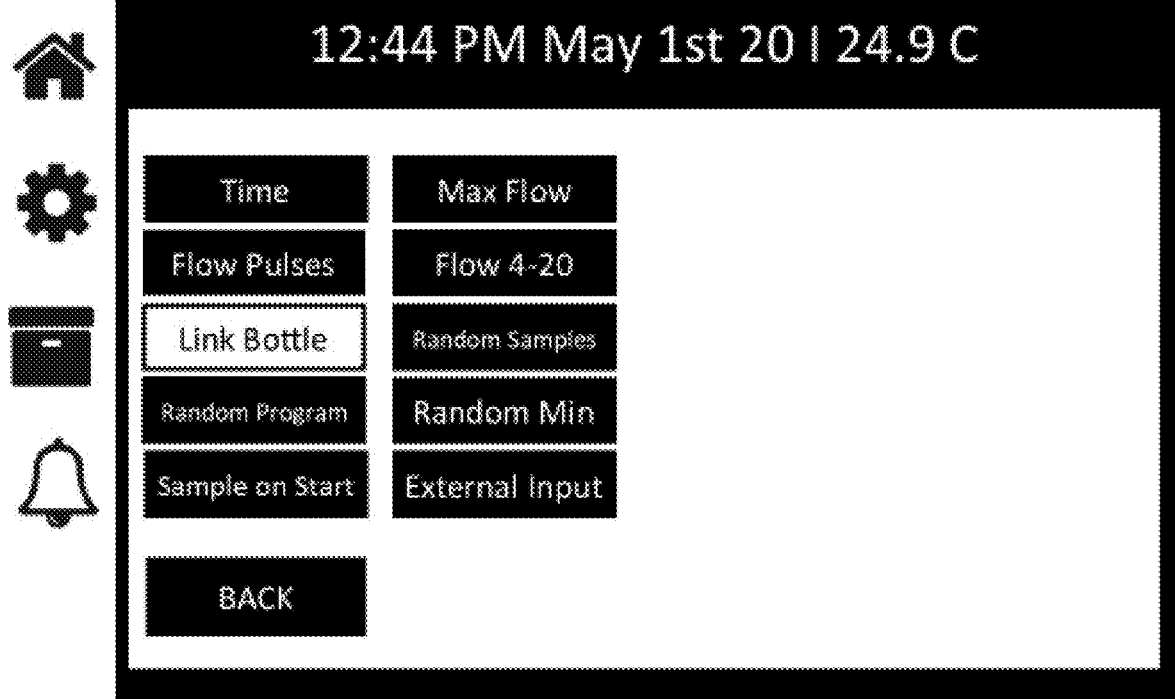

The Link Bottle setting allows linking bottles from different samples (FIG. 49).

Figure 50:
Figure 51:
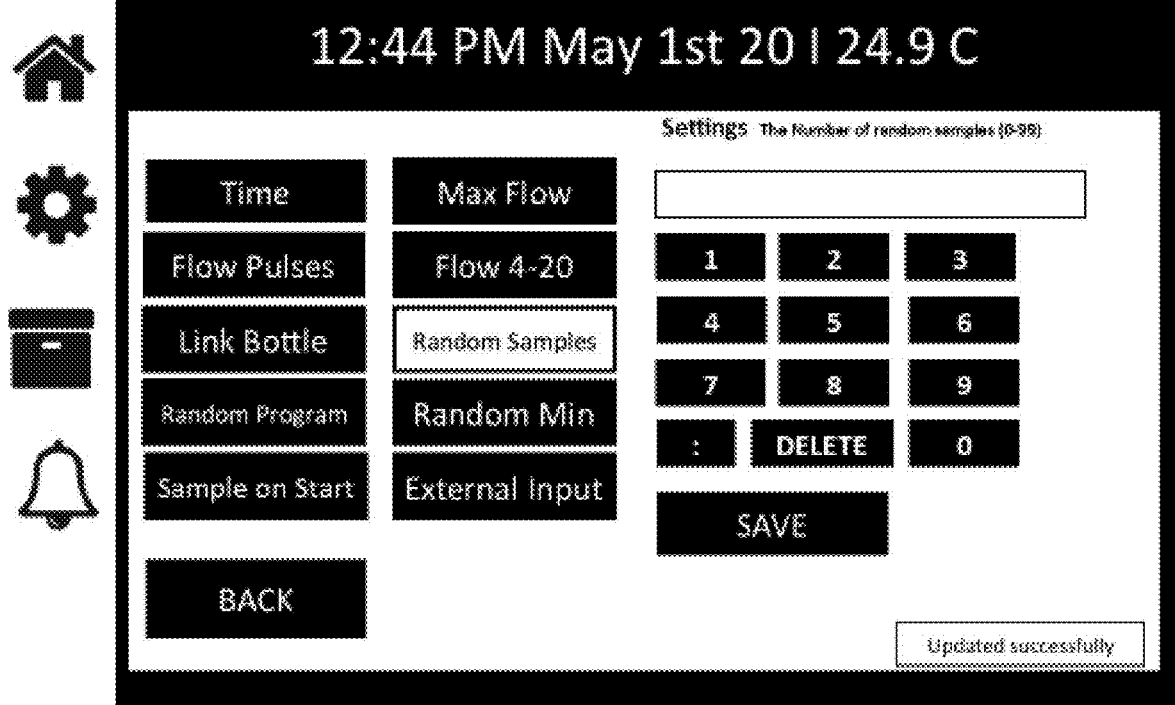

The Random Samples setting allows the sampler to pull a specific number of samples at random times within a set time (FIG. 50). This setting allows setting of the number of Random Samples to take, the time frame (Random Program) and the minimum amount of time (Random Min) between each sample. Press the "Random Samples" button to access the numeric entry keys used to enter the number of samples in the window under "SETTINGS". The Random Samples range from 0-99 samples. After entering the number of samples, press Save, and "Updated Successfully" will appear in the lower right-hand corner if the value is accepted (FIG. 51).

Figure 52:
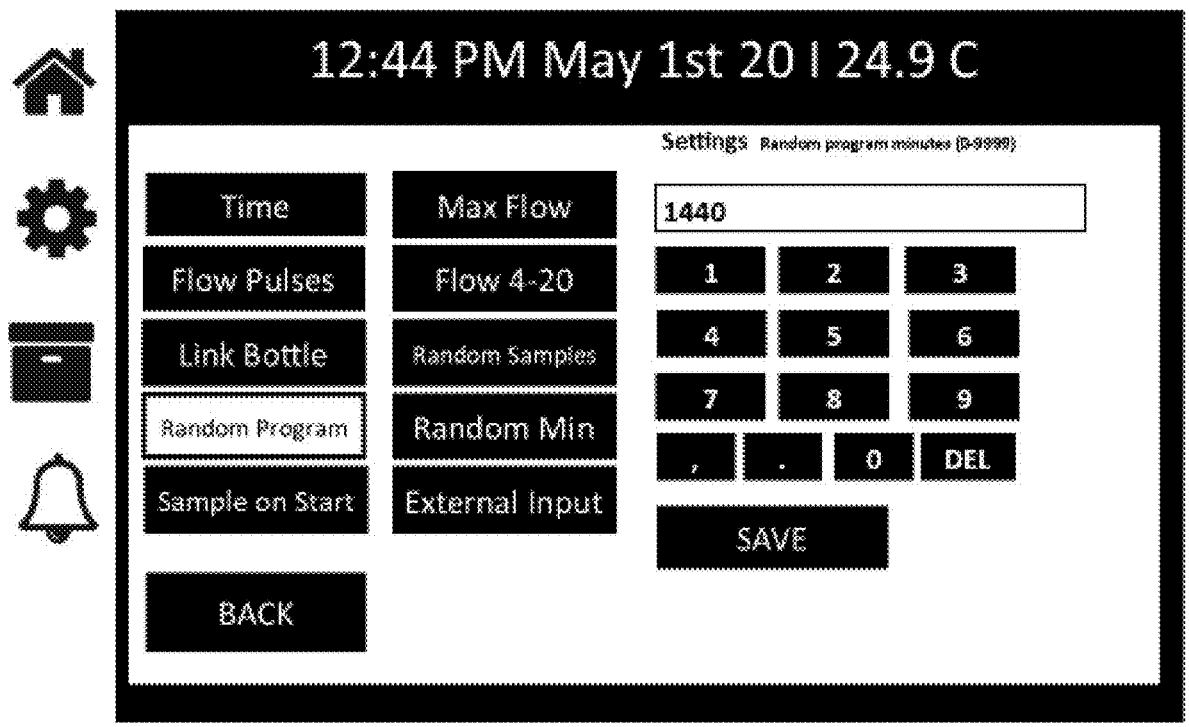
Figure 53:
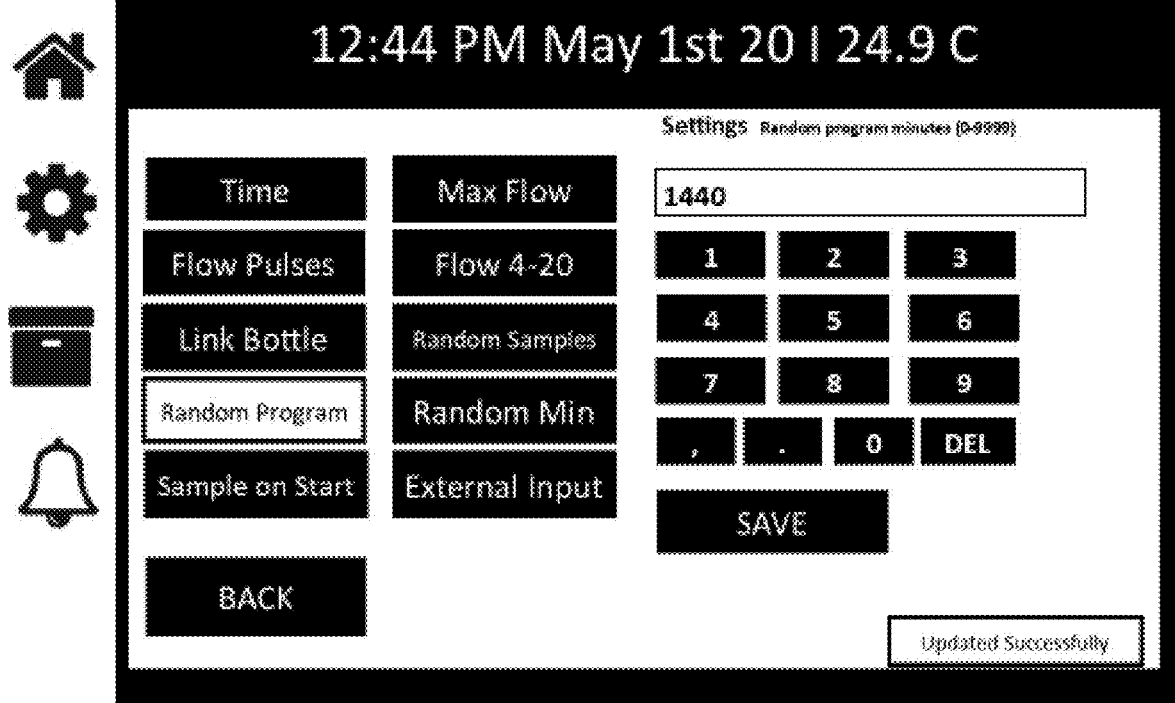

The Random Program setting is the time frame the sampler is set to pull the number of samples set in the Random Samples step above (FIG. 52). Press the "Random Program" button to access the numeric entry keys used to enter the time in the window under "SETTINGS". The Random Program range is from 0-9999 minutes. Enter the amount of time for the sampler to pull the samples. After entering the time value, press Save, and "Updated Successfully" will appear in the lower right-hand corner if the value is accepted (FIG. 53).

Figure 54:
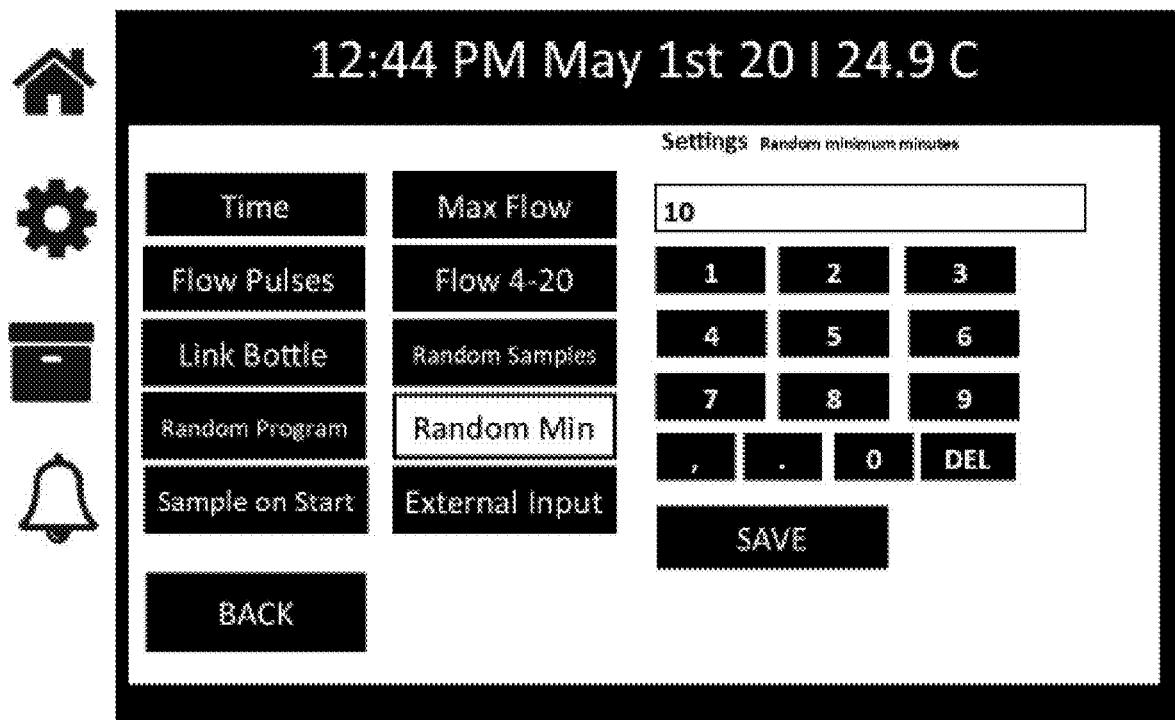
Figure 55:
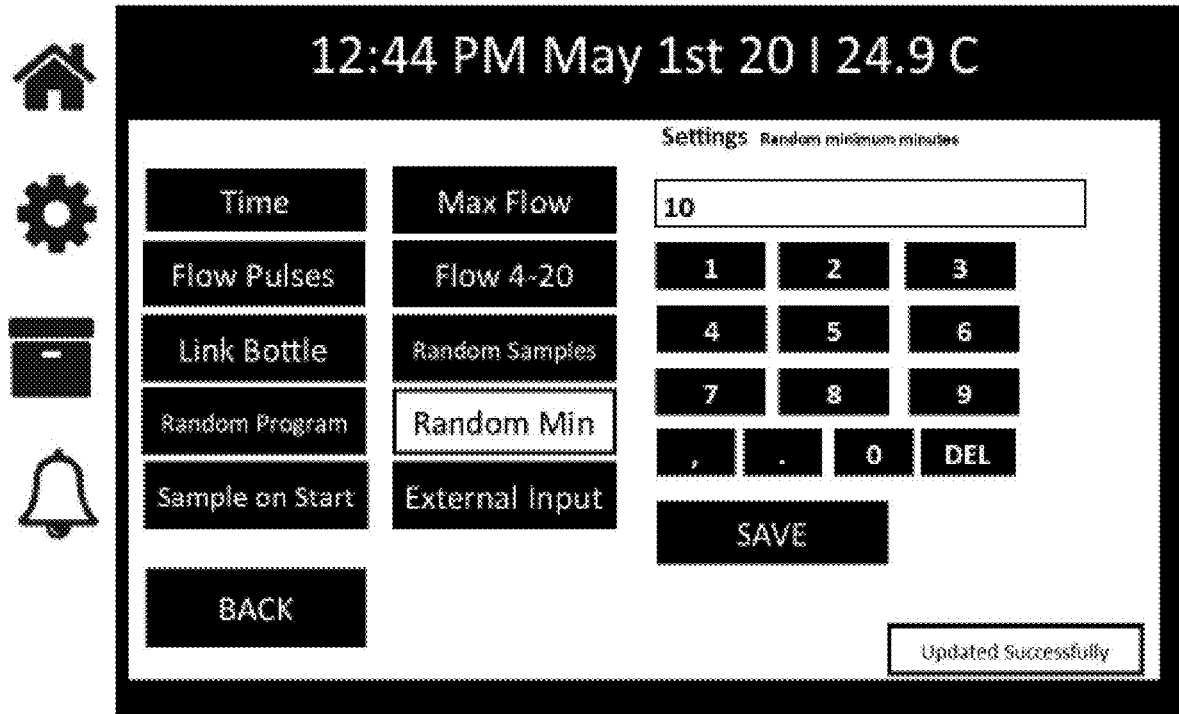

The Random Min setting is the minimum time between samples the sampler will use based on the number of samples set in the Random Samples setting and within the time set in the Random Program setting (FIG. 54). Press the "Random Min" button to access the numeric entry keys used to enter the time in the window under "SETTINGS". The Random Min range is from 10-9999 minutes. Enter the time the sampler will pause between samples. After entering the minimum time between samples value, press Save, and "Updated Successfully" will appear in the lower right-hand corner if the value is accepted (FIG. 55).

Figure 56:
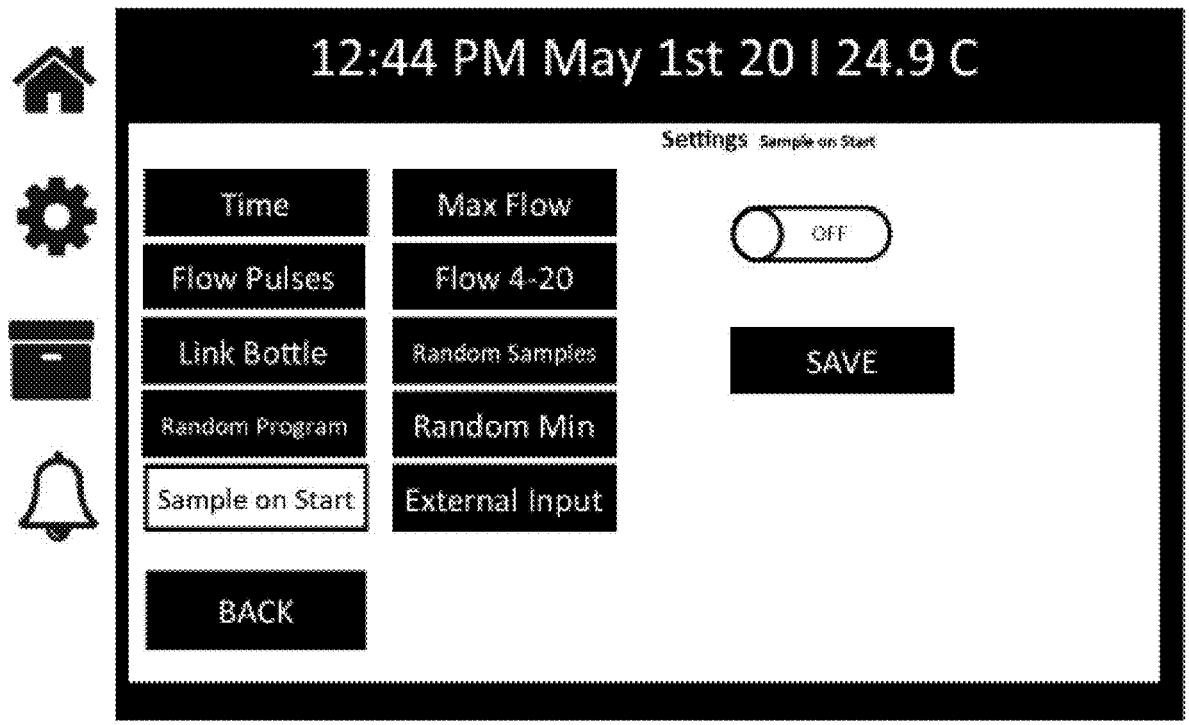
Figure 57:
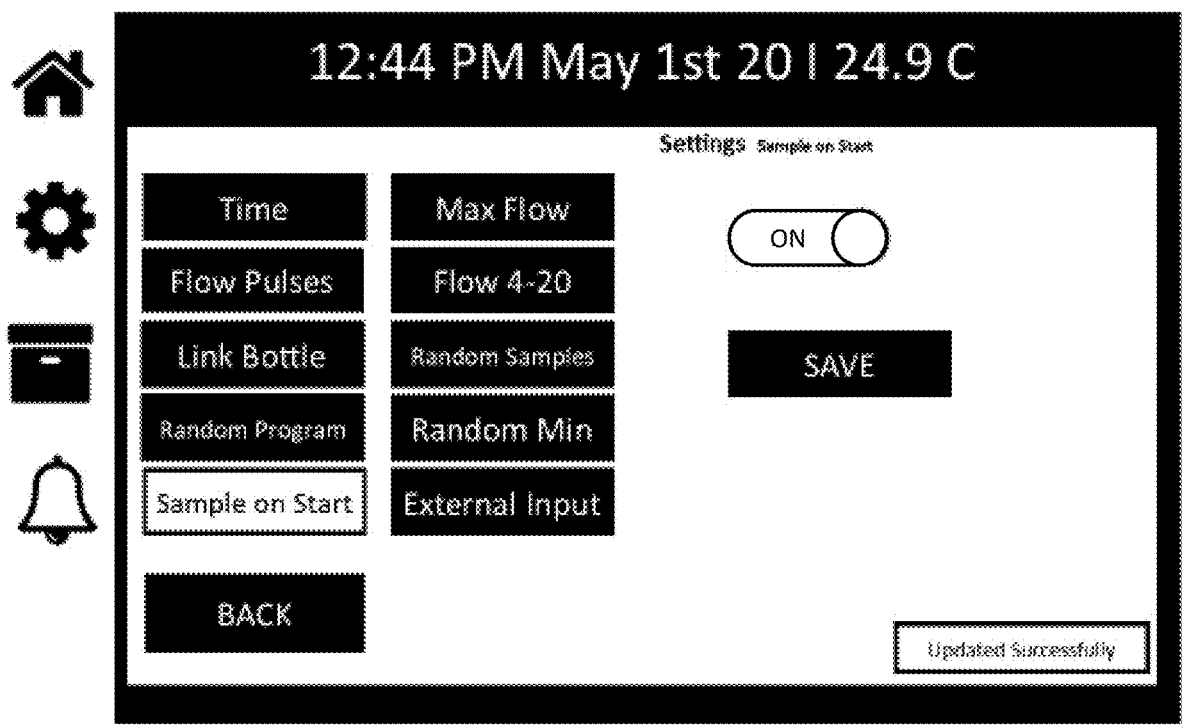

The Sample on Start setting allows the choice, if desired to take a sample first when starting the program or based on the program time of flow (FIG. 56). When a program is started with this setting ON, it pulls a sample immediately providing immediate feedback (FIG. 57).

Figure 58:
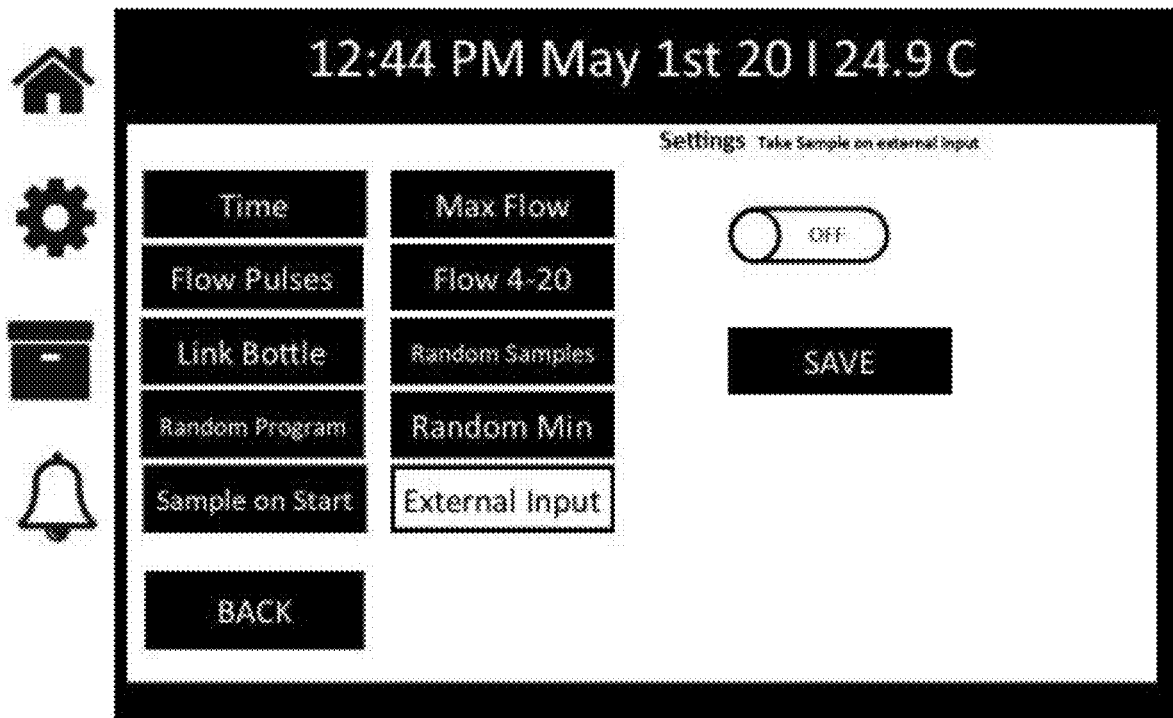
Figure 59:
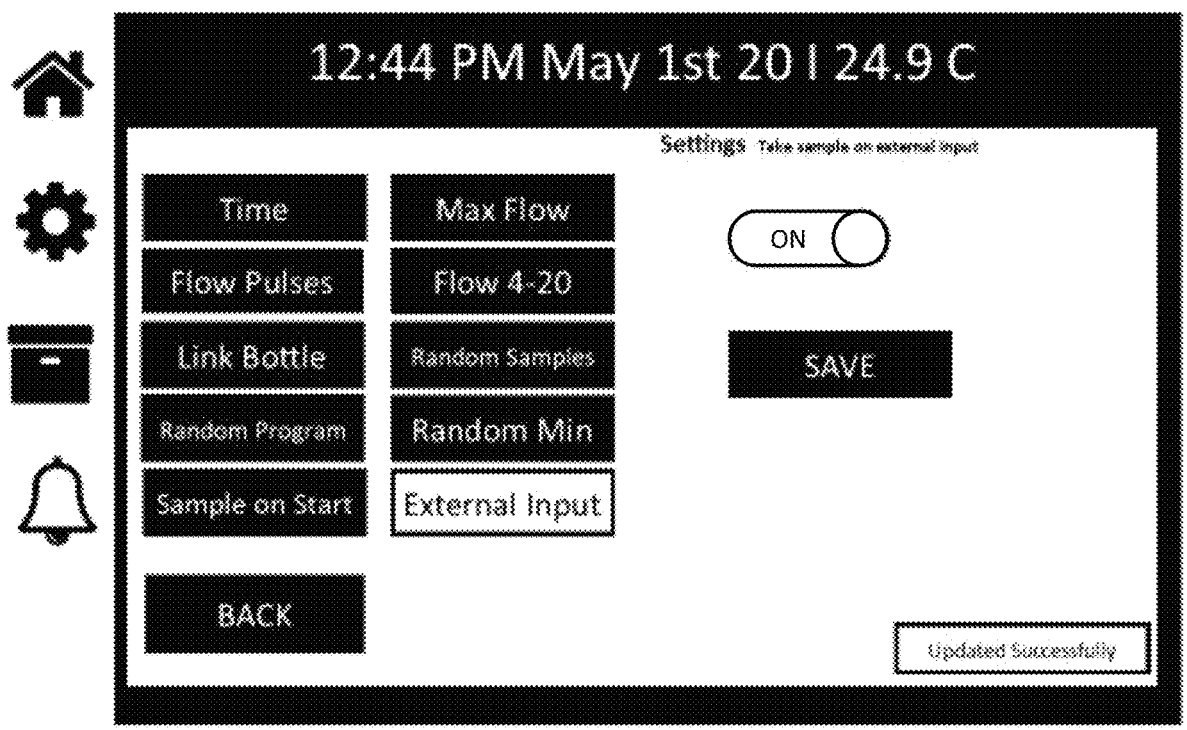

The External Input setting allows for an immediate sample to be taken outside of the sample parameters (FIG. 58). Every time the contact is closed a sample is taken. Press the "External Input" button to access the entry window. If this setting is OFF (under "SETTINGS") the button will be white with the words OFF. If this setting is ON, the button will be Green with the words ON. Select the desired setting ON or OFF. After selecting ON/OFF per your preference, press Save, and "Updated Successfully" will appear in the lower right-hand corner if the value is accepted (FIG. 59).

Figure 60:
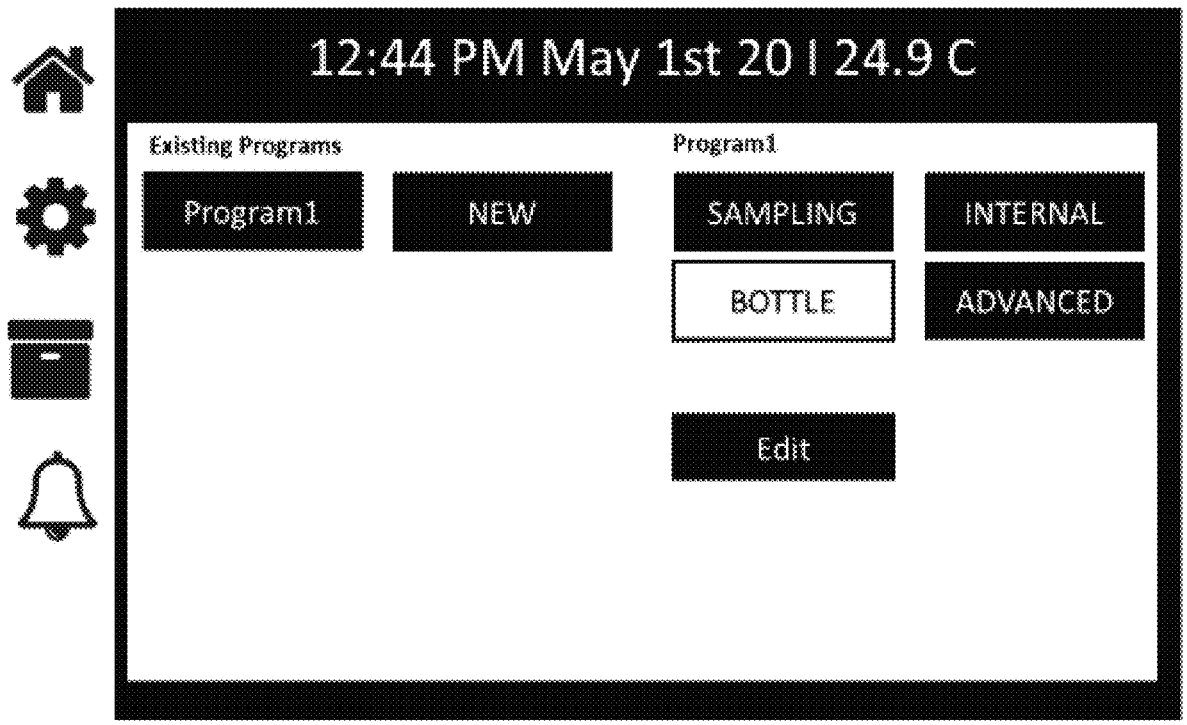
Figure 61:
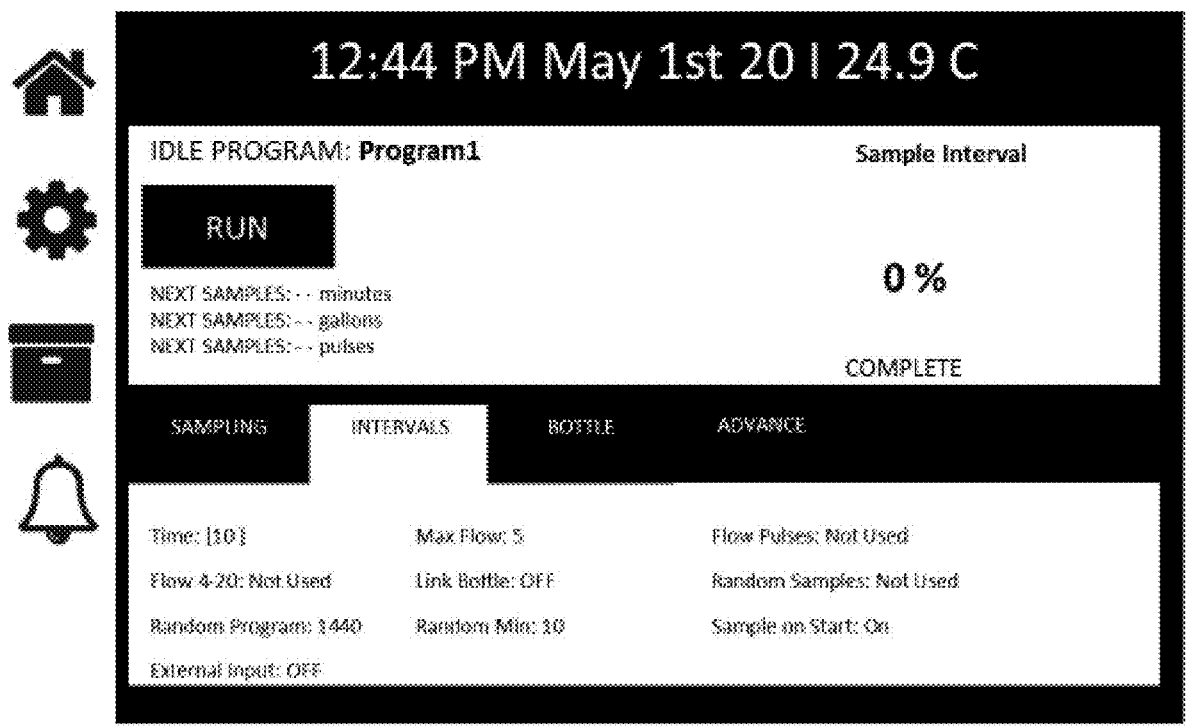

If more program changes are needed after you have saved your changes, press the "BACK" button to display the "EXISTING PROGRAMS" screen (FIG. 60). If all the program changes are complete, press the Home icon to view and verify your selections under their respective TAB. If all selections are correct press the "RUN" button when ready to sample (FIG. 61). Any time the programming is complete press the Home icon to return to the Home screen.

Figure 62:
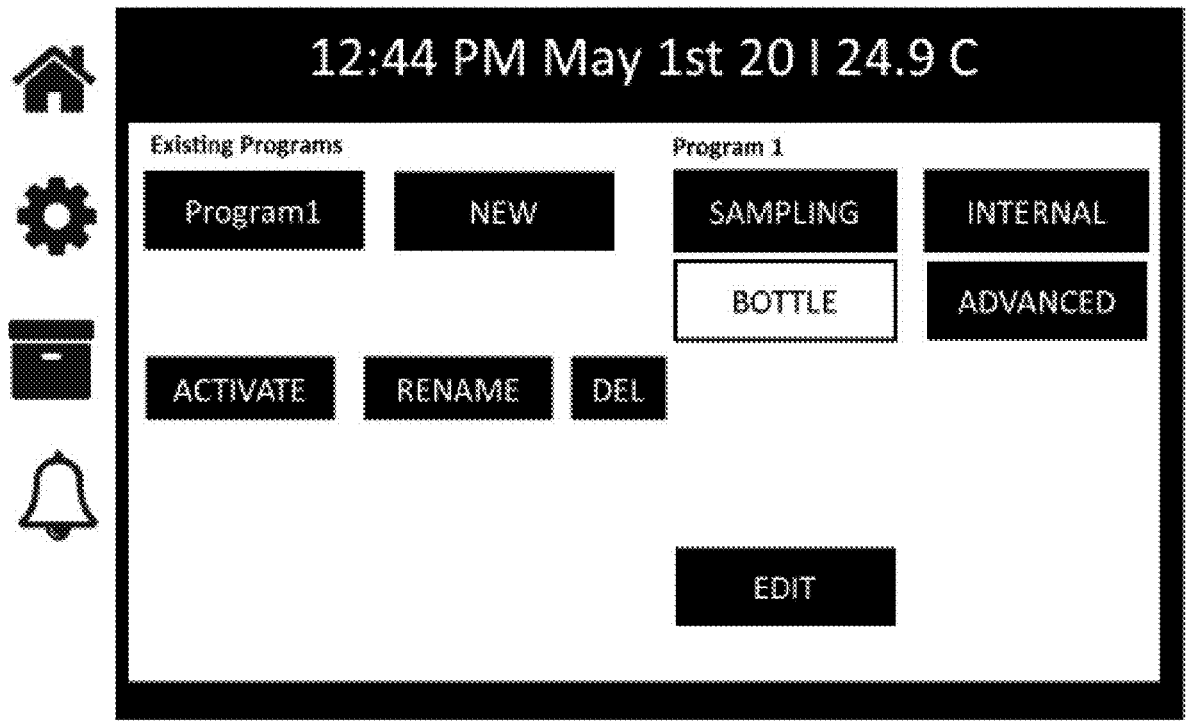
FIGS. 62-73 are bottle setting screens of the present invention.
Figure 63:
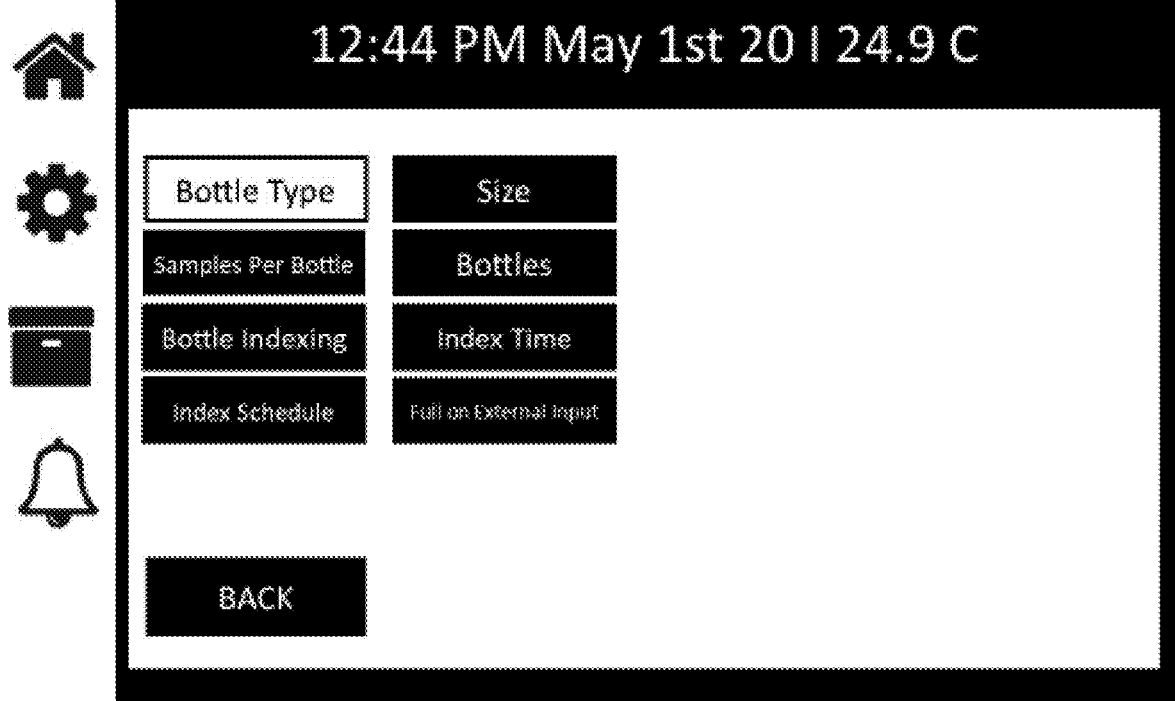

The "BOTTLE" settings define the information about a sample bottle. From the "EXISTING PROGRAMS" screen press the "BOTTLE" button and the "EDIT" button will appear on the screen (FIG. 62). Press the "EDIT" button to access to the BOTTLE functions screen (FIG. 63). All "Settings" may be accessed and changed from the same screen.

Figure 64:
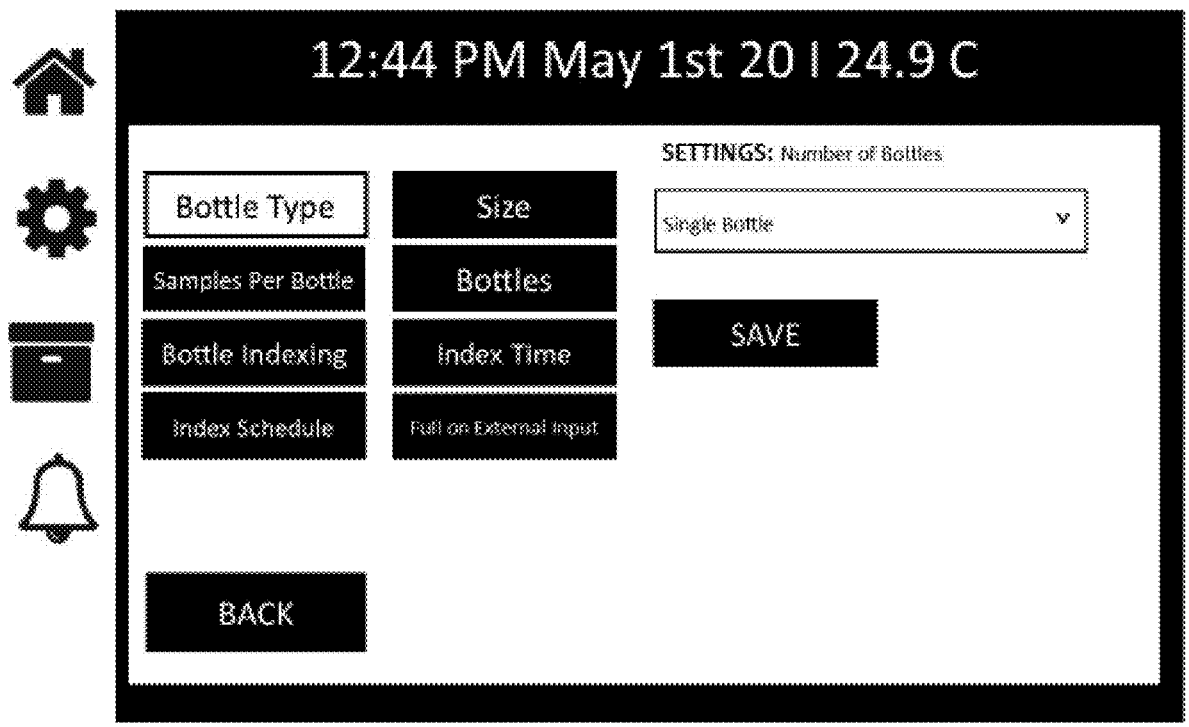
Figure 65:
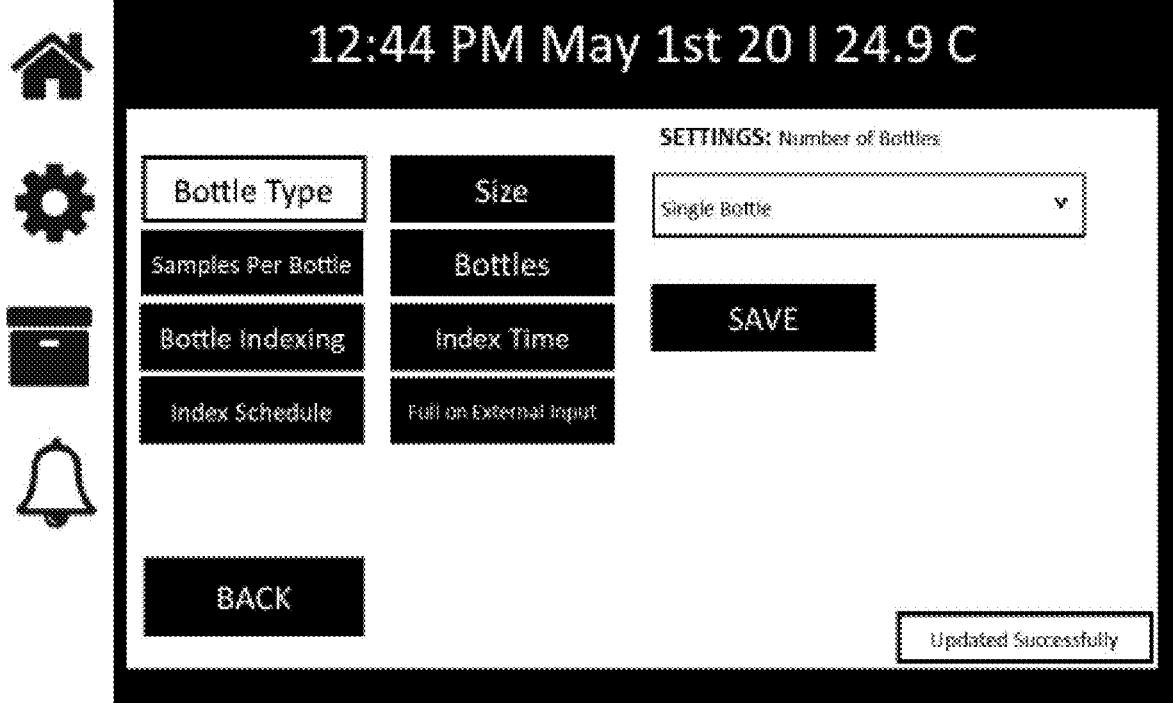

Press the "Bottle Type" button to display the options of single and multiple bottles under "SETTINGS" (FIG. 63). Open the pulldown window by pressing the down arrow on the right side of the box. This pulldown window will show single bottle or multiple bottles. Select single bottle (FIG. 64). After selecting "single bottle", press Save, and "Updated Successfully" will appear in the lower right-hand corner if the value is accepted.

Figure 66:
Figure 67:
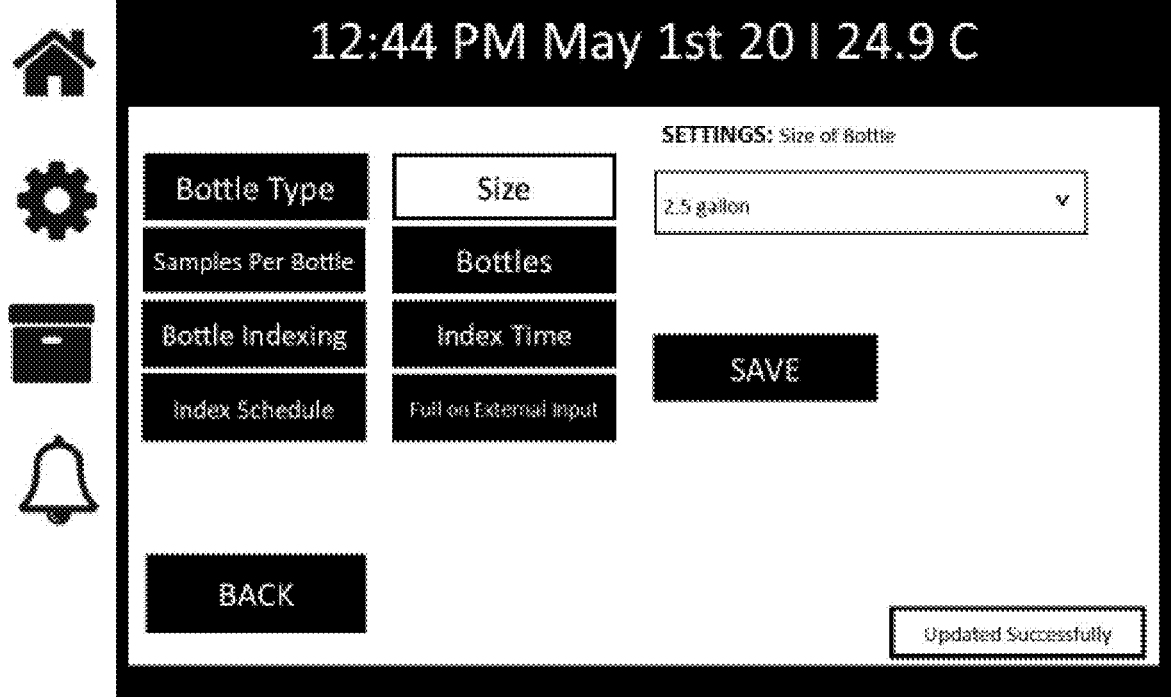
Figure 68:
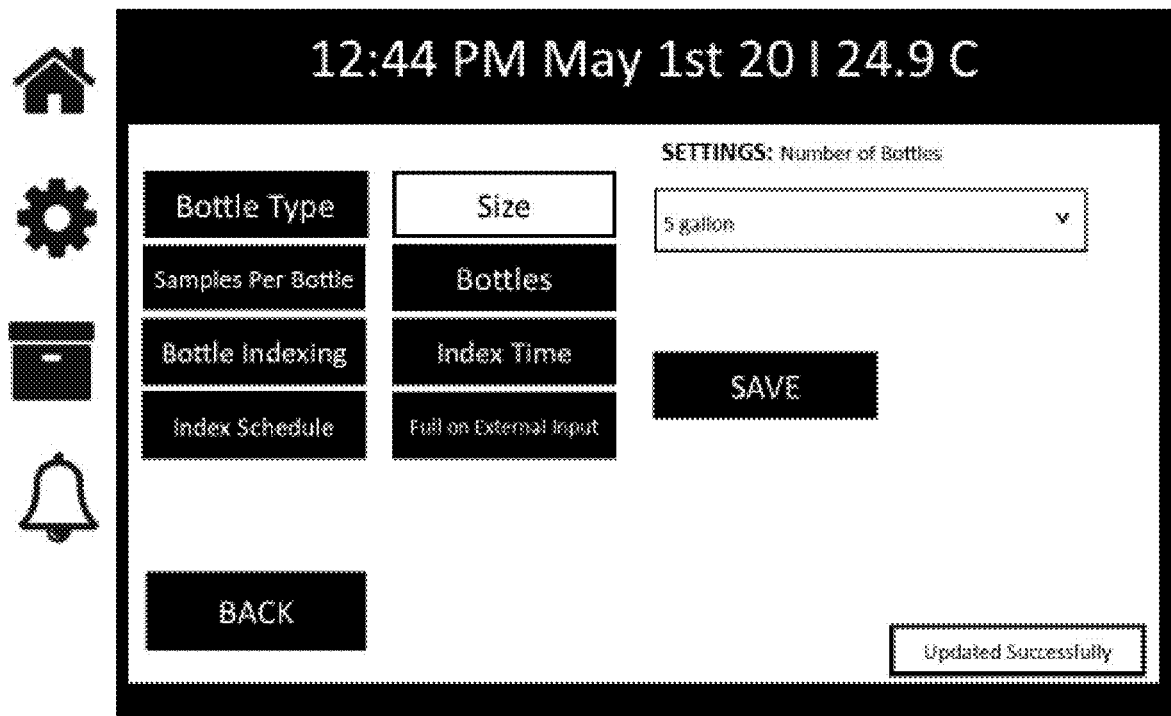

The Size setting button allows the bottle size to be changed for the current program. Press the "Size" button to display the options of bottle sizes under "SETTINGS" (FIG. 66). The pulldown window may be opened by pressing the down arrow on the right side of the box. This pulldown window will show a bottle size such as 2.5 gallon or 5.0 gallon, for example. Select the desired Bottle size. After selecting the bottle size, press Save, and "Updated Successfully" will appear in the lower right-hand corner if the value is accepted (FIGS. 67 and 68).

Figure 69:
Figure 69:
Figure 69:
Figure 69:
Figure 70:
Figure 70:
Figure 70:
Figure 70:

Samples Per Bottle setting is the number of samples that are needed to fill a 2.5 or 5-gallon bottle, for example. Press the "Samples per Bottle" button to access the numeric entry keys used to enter the samples per bottle in the window under "SETTINGS" (FIG. 69). Enter the number of Samples Per Bottle for this program. After entering the number of samples per bottle, press Save, and "Updated Successfully" will appear in the lower right-hand corner if the value is accepted (FIGS. 69 and 70).

Figure 71:
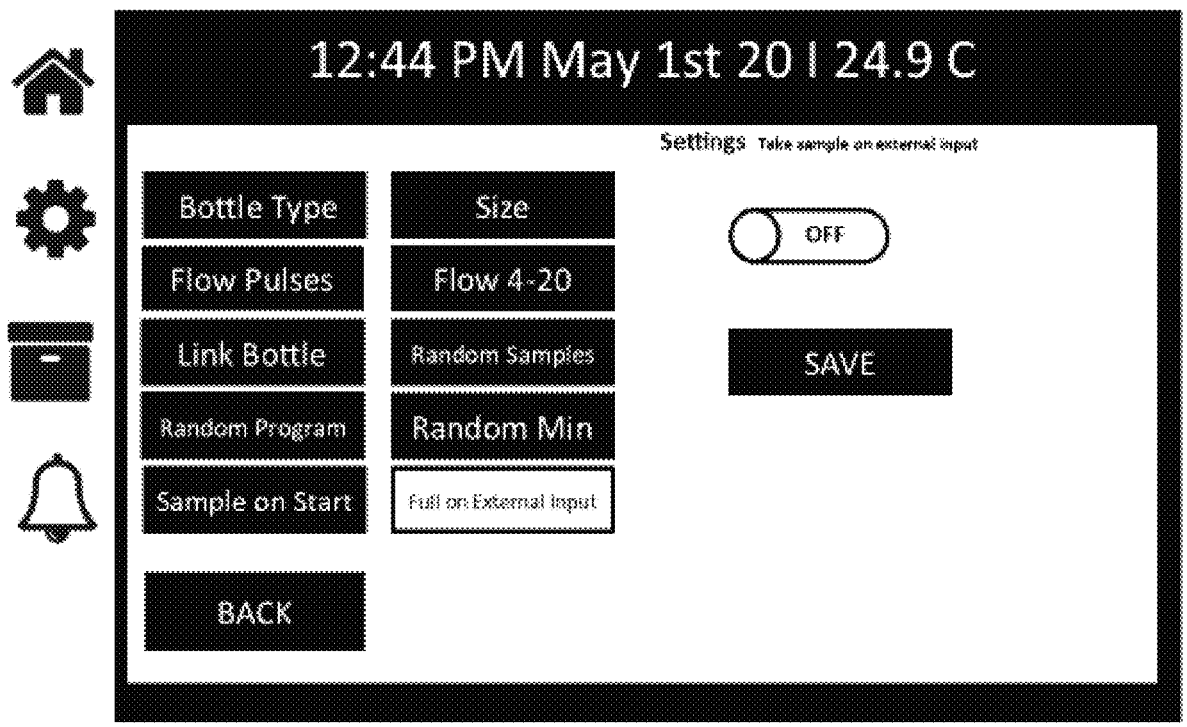
Figure 72:
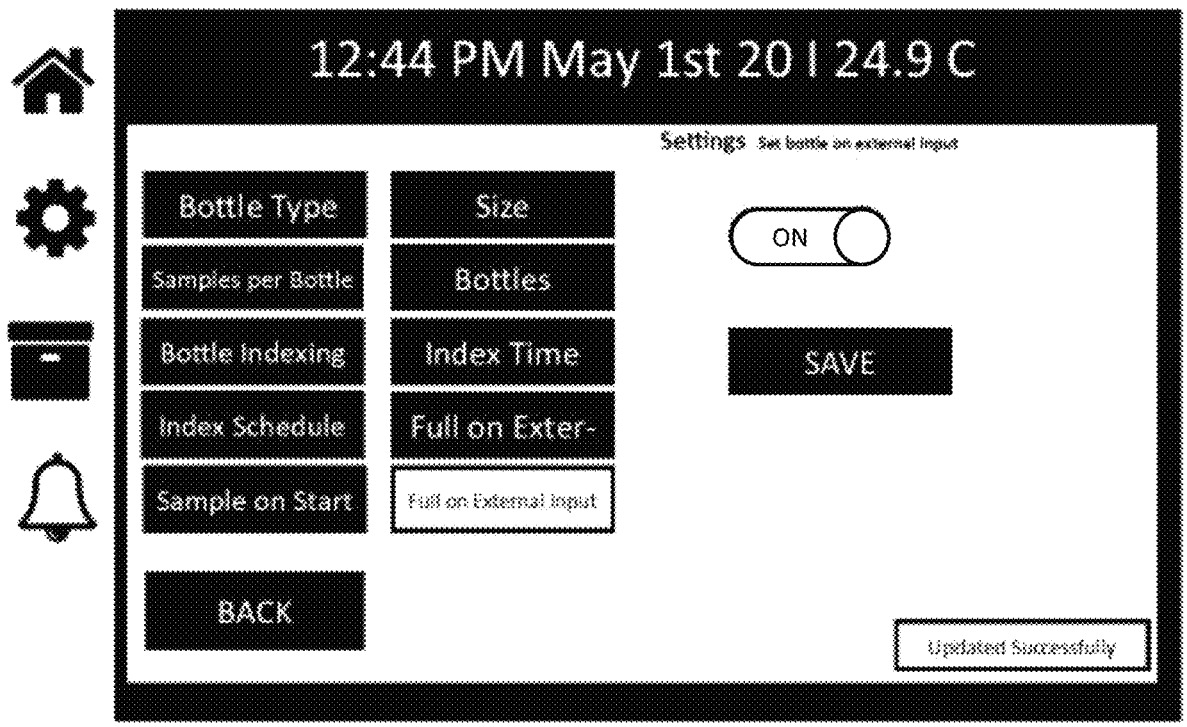

The Full on External Input setting is used with the Full Bottle Float Switch. The float switch mounts in the lid of a bottle. If the bottle becomes too full, it will trigger the float switch and shut the sampling program off to prevent a spill inside the sampler. When the container is emptied the program will start running again. Press the "Full on External Input" button to display the options of ON or OFF under "SETTINGS" (FIG. 71). The window will show ON or OFF. Select the desired setting ON or OFF. After selecting ON/OFF per your preference, press Save, and "Updated Successfully" will appear in the lower right-hand corner if the value is accepted (FIG. 72).

If more program changes are desired after saving the changes, press the "BACK" button to return to the "EXISTING PROGRAMS" screen, then select the next item requiring changes.

Figure 73:

If all the program changes are complete, press the Home icon to view and verify selections under their respective TAB. If all selections are correct press the "RUN" button when ready to sample (FIG. 73). Any time the programming is complete press the Home icon to return to the Home screen.

Figure 74:
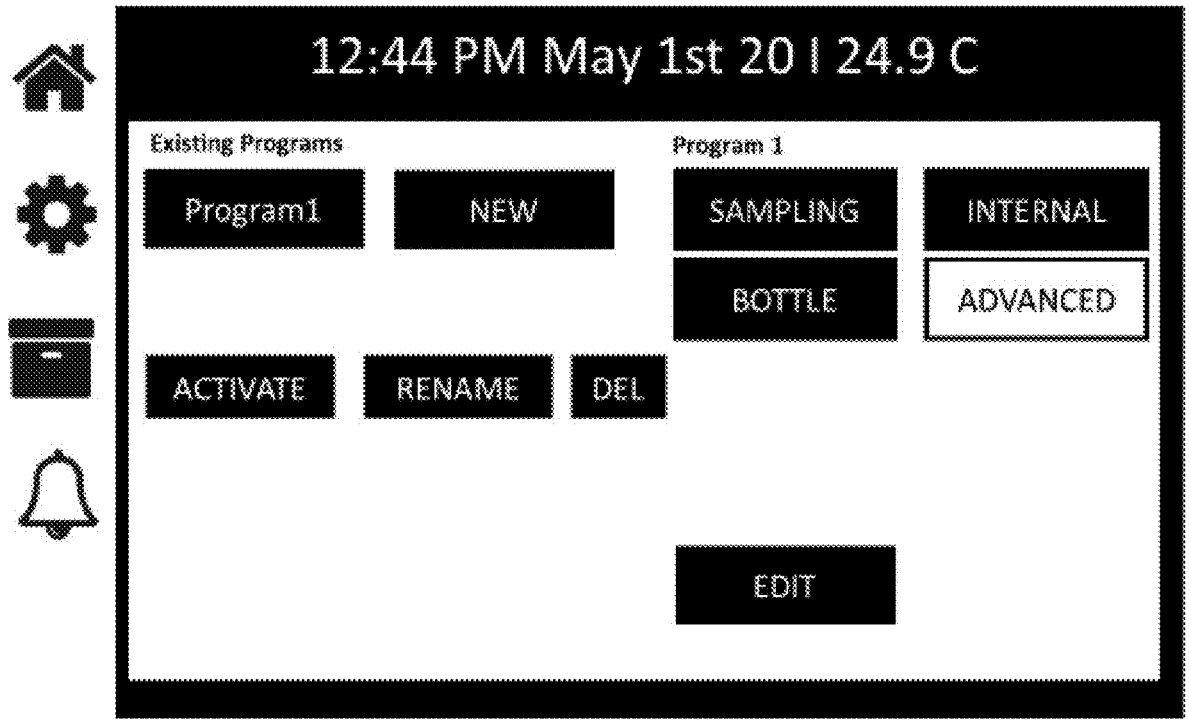
FIGS. 74-99 are advanced screens of the present invention.

The ADVANCED settings allow you to set up the Menu items (FIG. 74).

Figure 75:
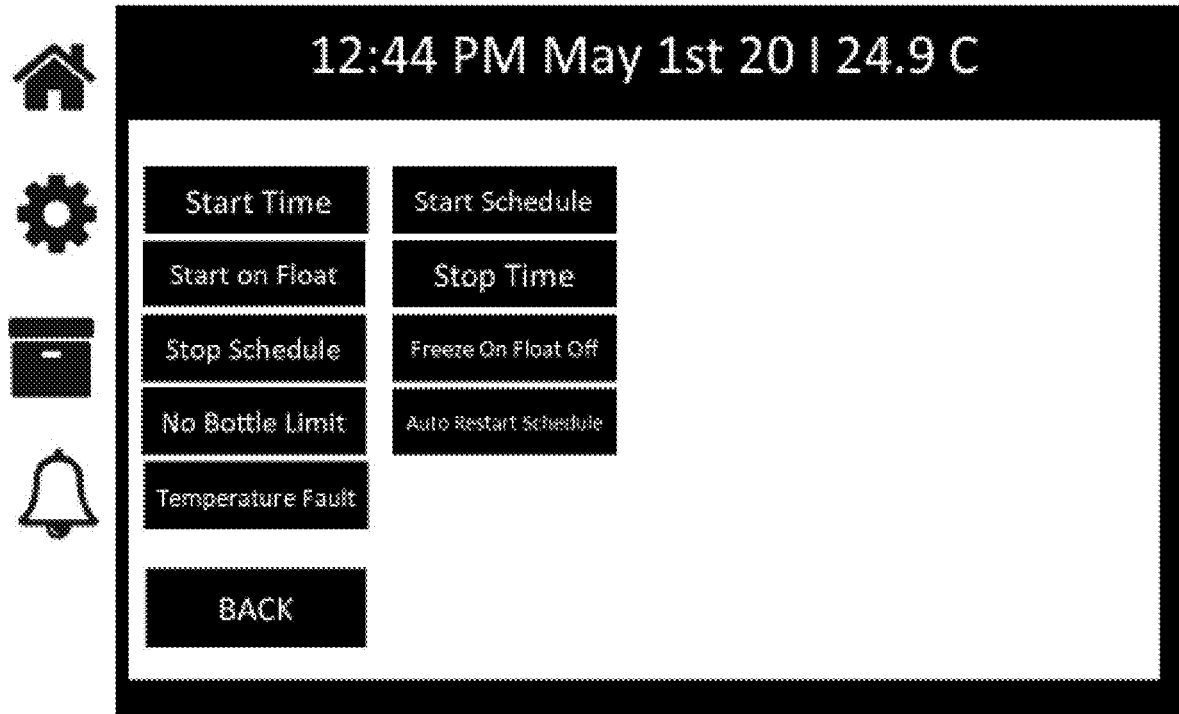

From the "EXISTING PROGRAMS" screen press the "ADVANCED" button and the "EDIT" button will appear on the screen. Press the "EDIT" button to access the ADVANCED settings screen (FIG. 75). All "Settings" may be accessed and changed from the same screen.

Figure 76:
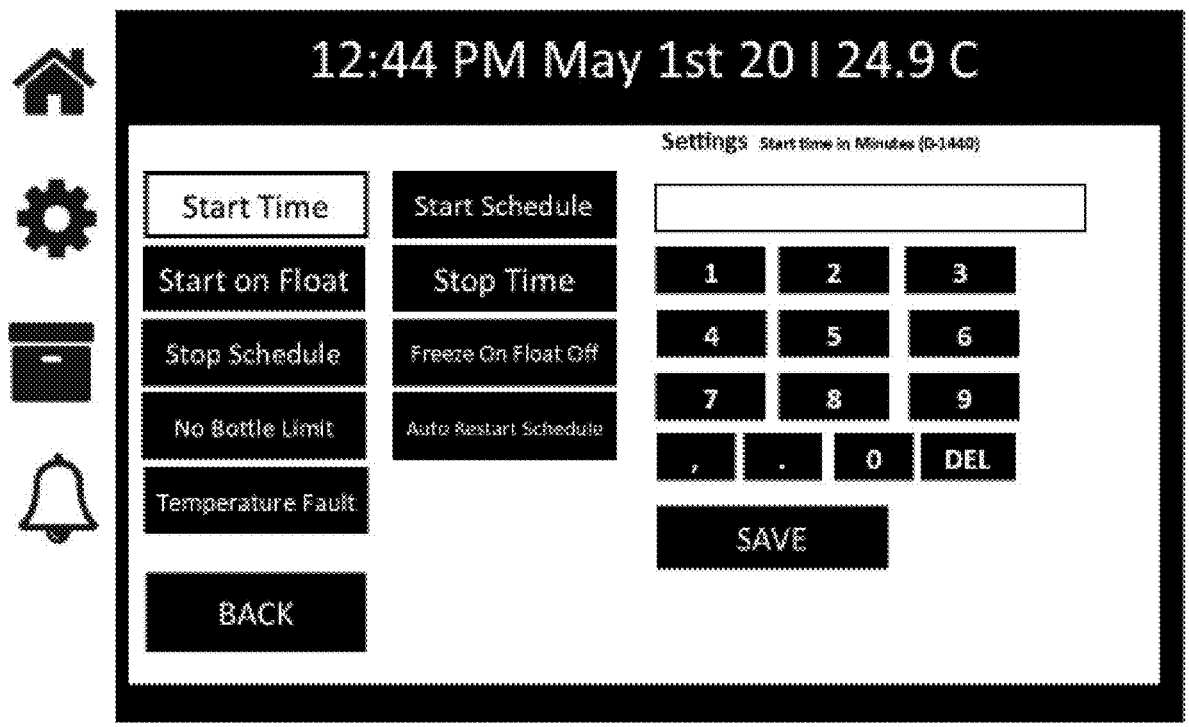
Figure 77:
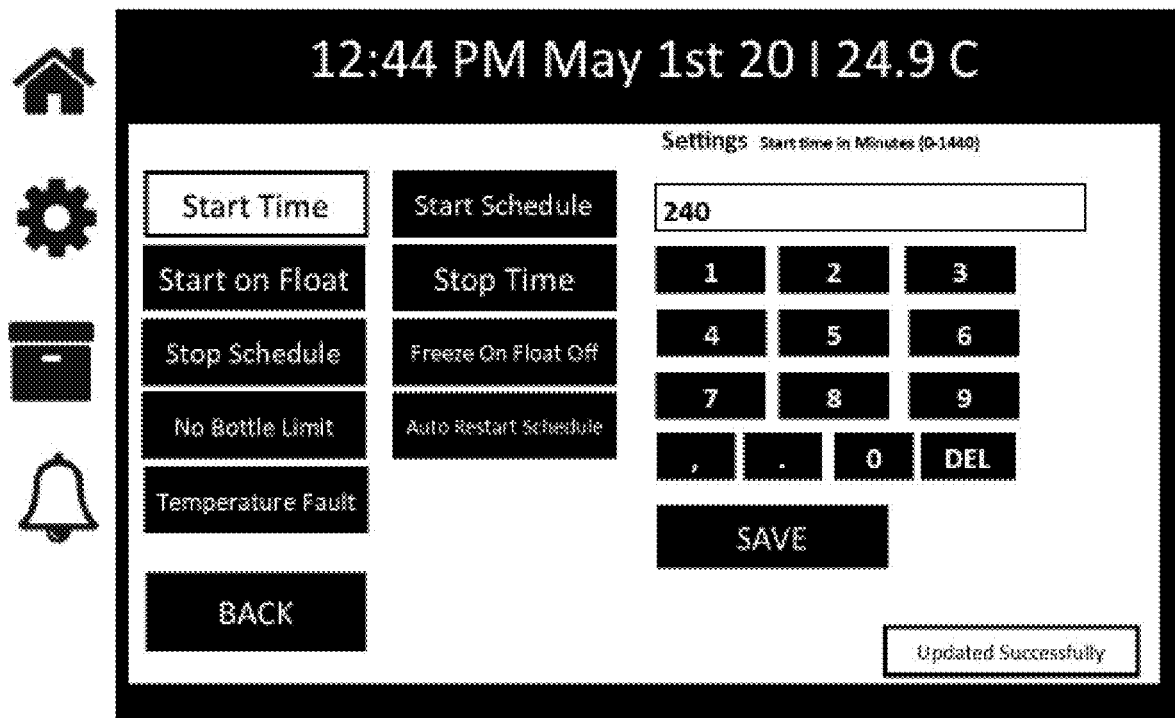

The Start Time setting allows for programming a specific amount of time delay before the program starts running (FIG. 76). For example, if the current time is 8:00 am and it is desired to start sampling at 12:00 p.m., 240 minutes would be entered (4×60=240) into the program line window (FIG. 77). Press the "Start Time" button to access the numeric entry keys used to enter the time in the window under "SETTINGS".

Figure 78:
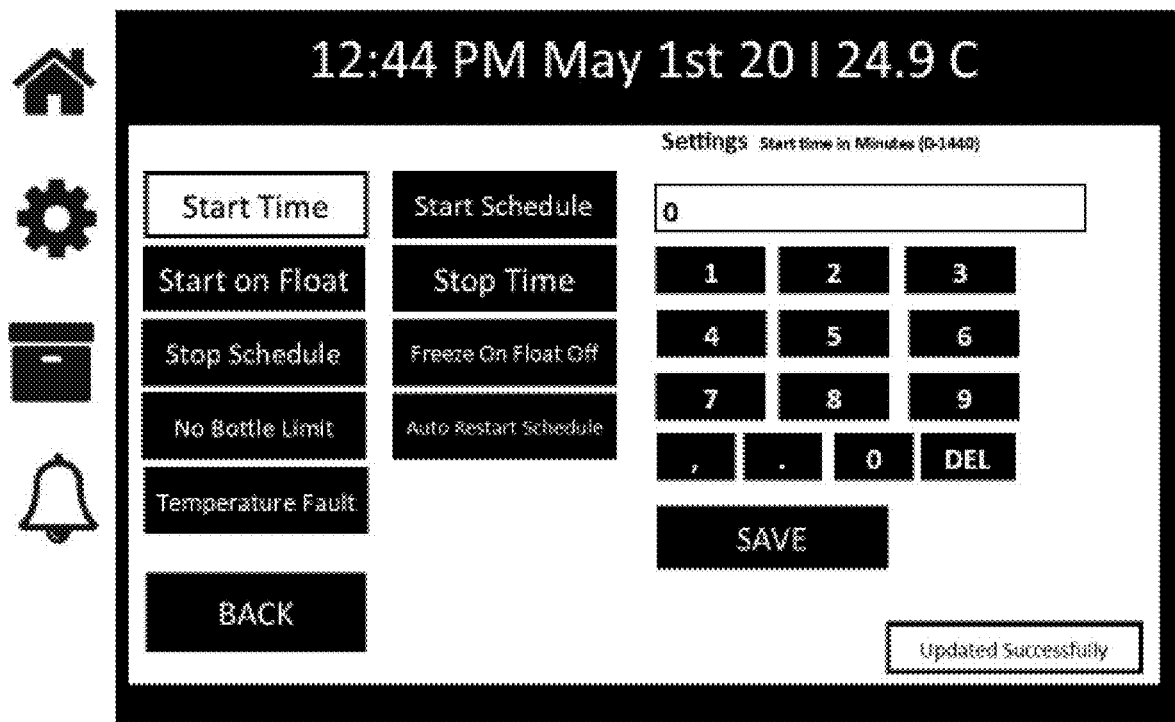

To run a Time or Flow based sample program with NO "Start Time" delay, set the value to "0" (FIG. 78). This will make the program start counting immediately. Enter the time value, and press Save, and "Updated Successfully" will appear in the lower right if the value is accepted.

Figure 79:
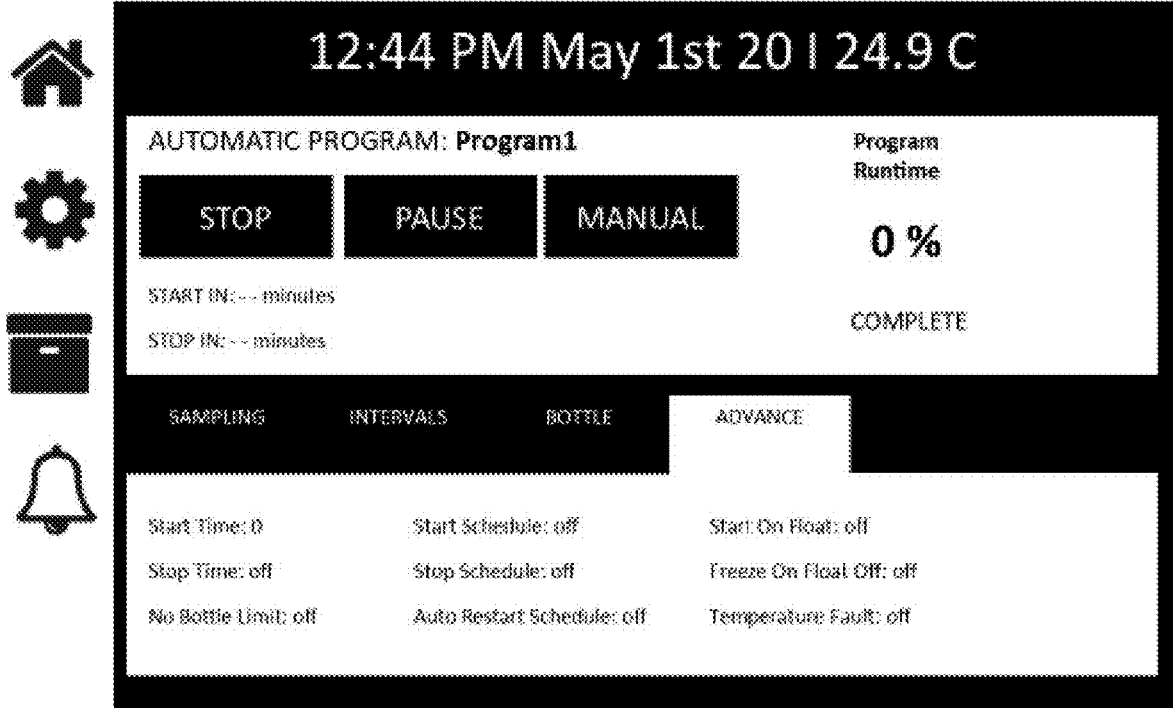

For example, if the programming is set to pull a sample every 10 minutes and it should start counting the 10 minutes down immediately, set "Time" under the Intervals settings to 10 and the "Start Time" to "0". Verify that the program is running correctly by pushing the program run FIG. 79).

Figure 80:
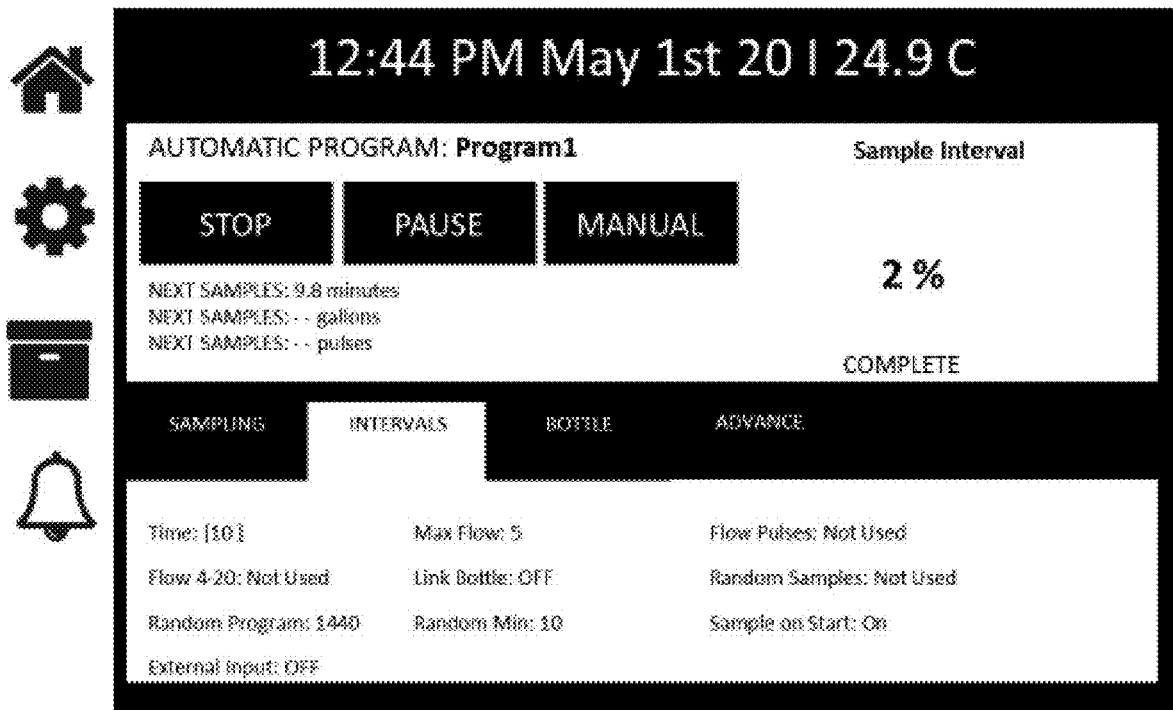

Press the Home icon then Run, the screen will advance from IDLE PROGRAM to Active Program. Select the ADVANCED TAB (FIG. 79), the Start Time displays 0. Select INTERVALS TAB, the Time will show [10] and just above it, directly underneath STOP, NEXT SAMPLES: 9.8 minutes shows that the counter is counting down (FIG. 80).

Figure 81:
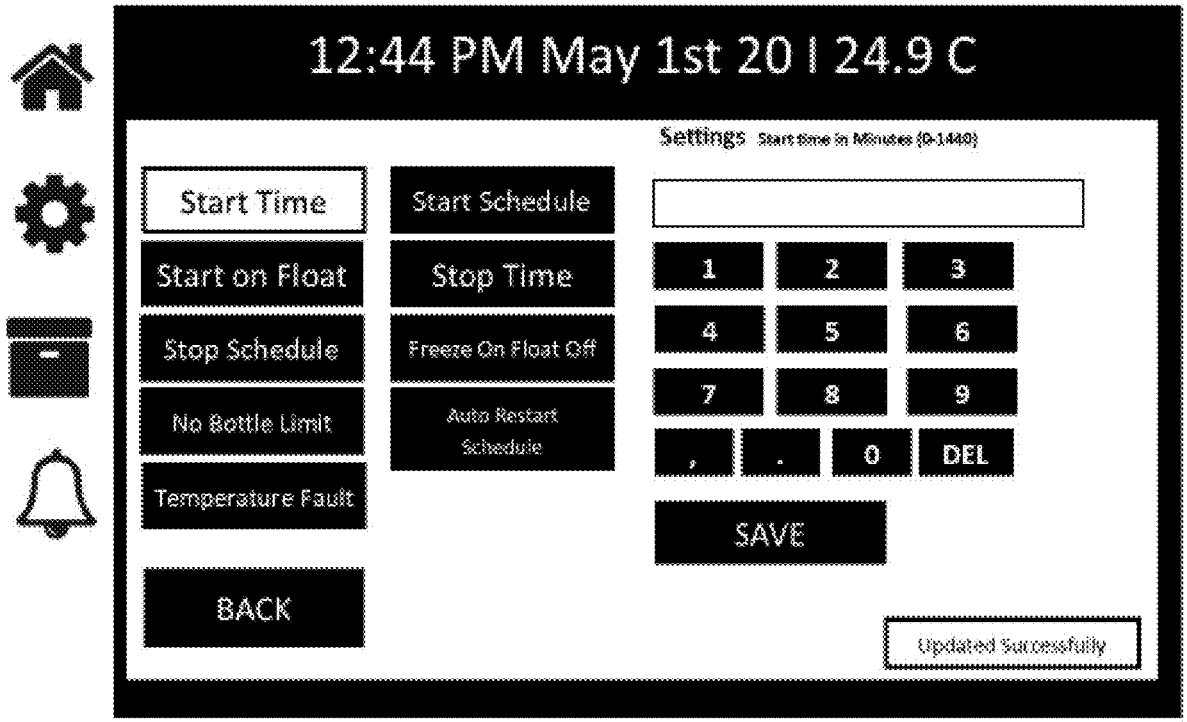
Figure 82:
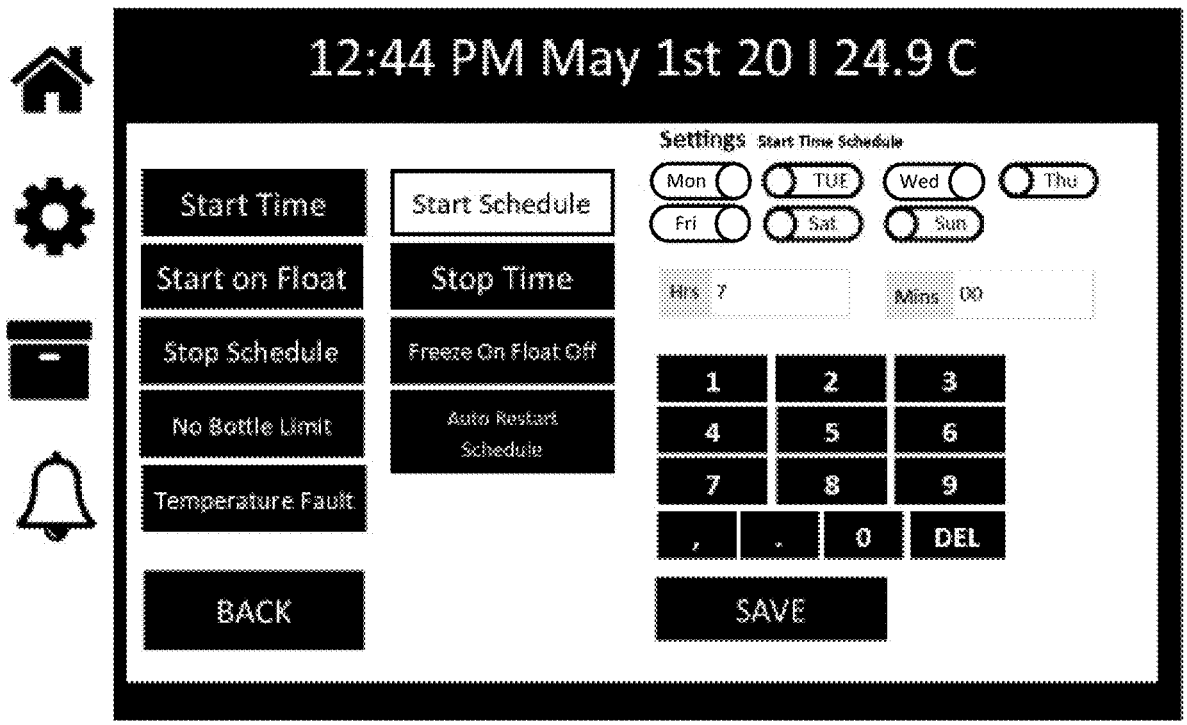

If a "Start Schedule" program will be run, the "Start Time" will be blank (FIG. 81). The Start Schedule setting is when a weekly or daily start program is needed. A "Start Schedule" is the day and time the program to start running (Sampling). Press the "Start Schedule" button to access the numeric entry keys used to enter the day(s) in the area under "SETTINGS" (FIG. 82). Touch the days desired for the program to take samples and they will become active.

Figure 83:
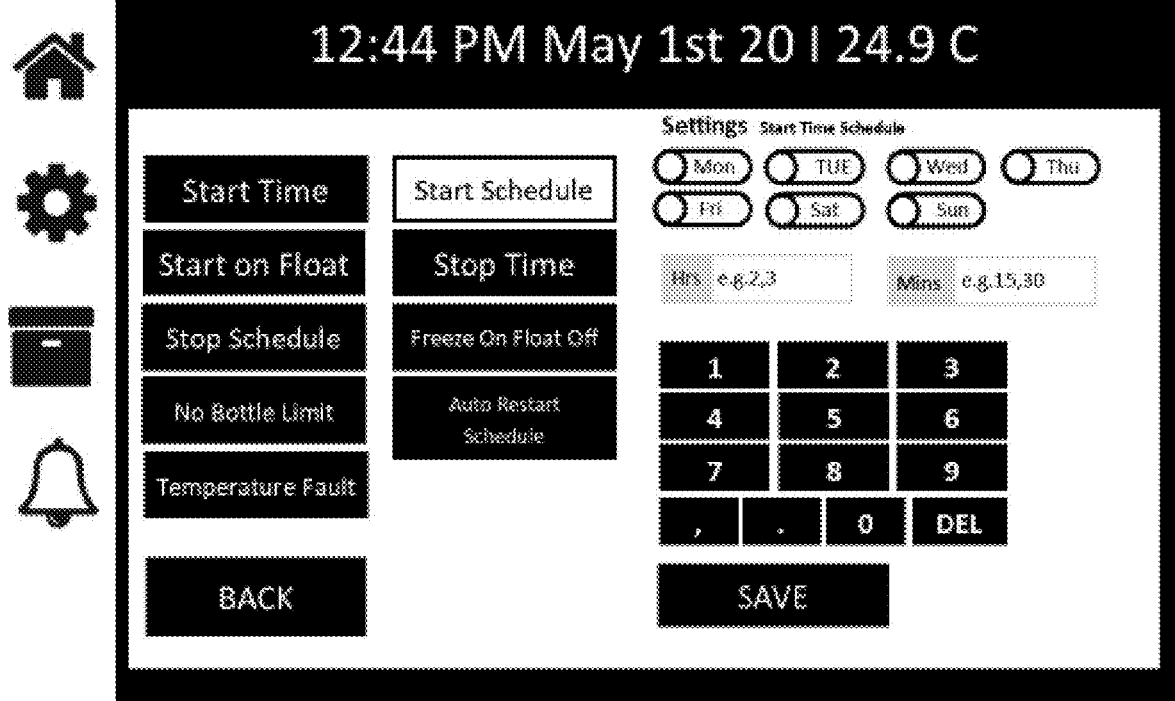
Figure 84:
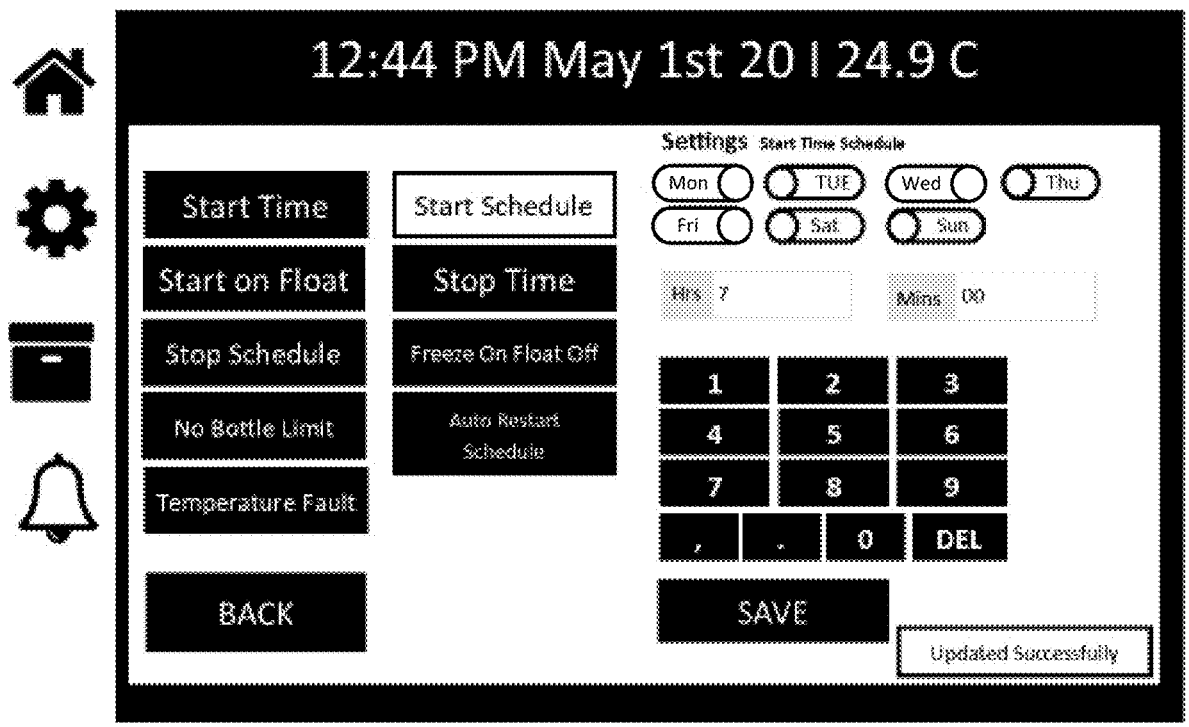

Enter the Hrs. and Min. in their respective box for the start time (FIG. 83). Time entries use 24 hr clock but will be displayed in standard. For example, sampling Mon, Wed, Fri and starting at 7:00 a.m. (FIG. 84). After ensuring all selections are correct, press Save, and "Updated Successfully" will appear in the lower right-hand corner if the value is accepted.

Figure 85:
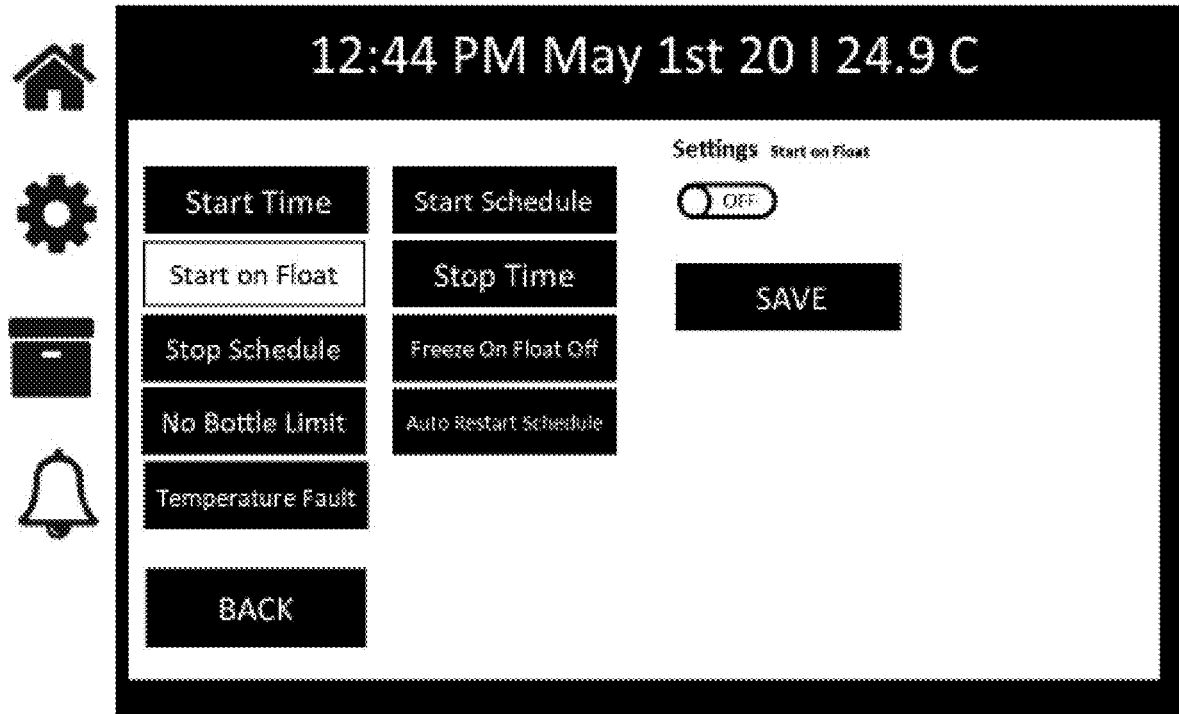
Figure 86:
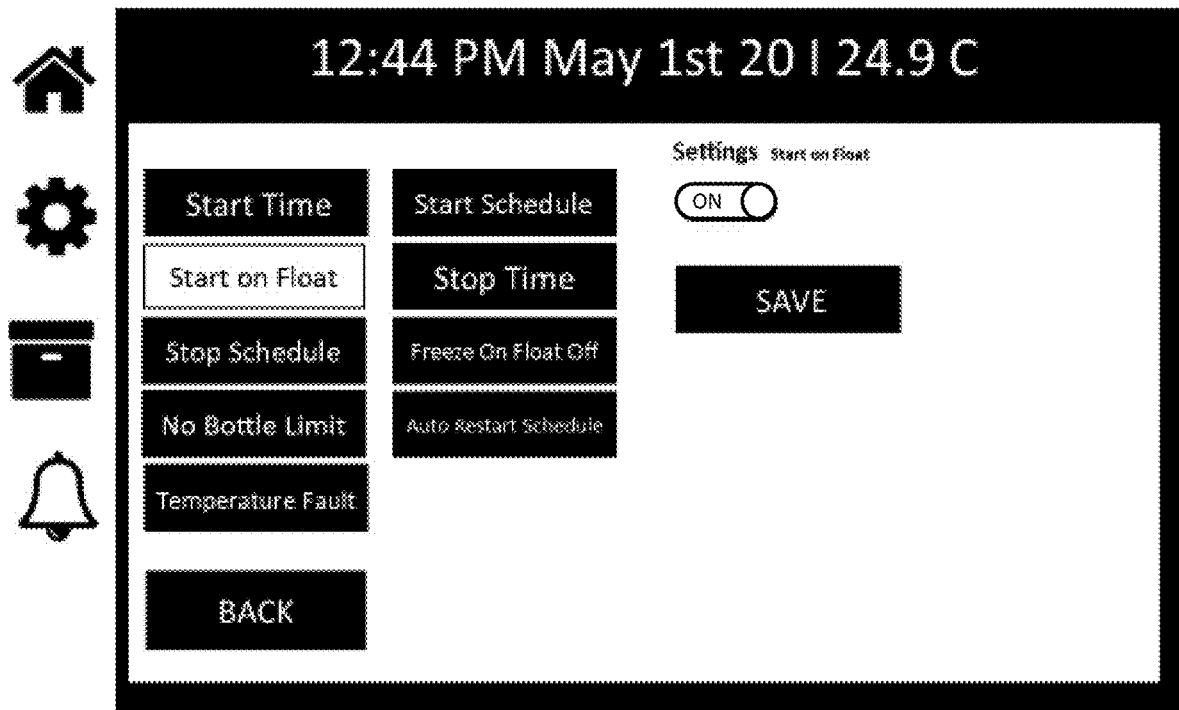

The Start on Float setting allows for an external float or switch to provide the sampler with a run signal (FIGS. 85 and 86). Once this run signal is received the program will run as scheduled until it is completed. This is a one-shot contact. For example, if monitoring the pH of a stream that must maintain 6.5 or above, the pH controller may be programmed to give an alarm (contact closure) when the pH falls below the 6.5. This contact then closes and makes the sampler run the program until it is complete. This also could be used as a float/contact start, once the contact closes the sampler runs the program.

Figure 87:
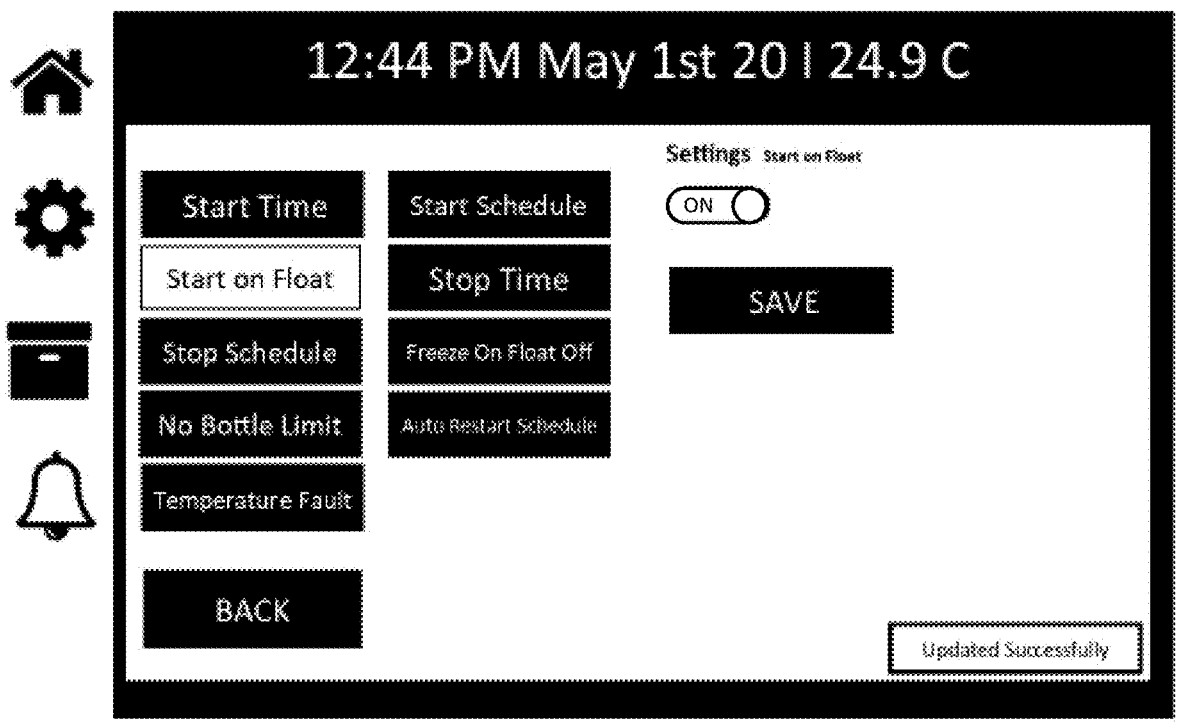

Press the "Start On Float" button to access the input window under "SETTINGS". If this setting is OFF the button will have the words OFF in it (FIG. 85). If this setting is ON the button will have the word ON in it (FIG. 86). After selecting ON/OFF, press Save, and "Updated Successfully" will appear in the lower right-hand corner if the value is accepted (FIG. 87).

Figure 88:
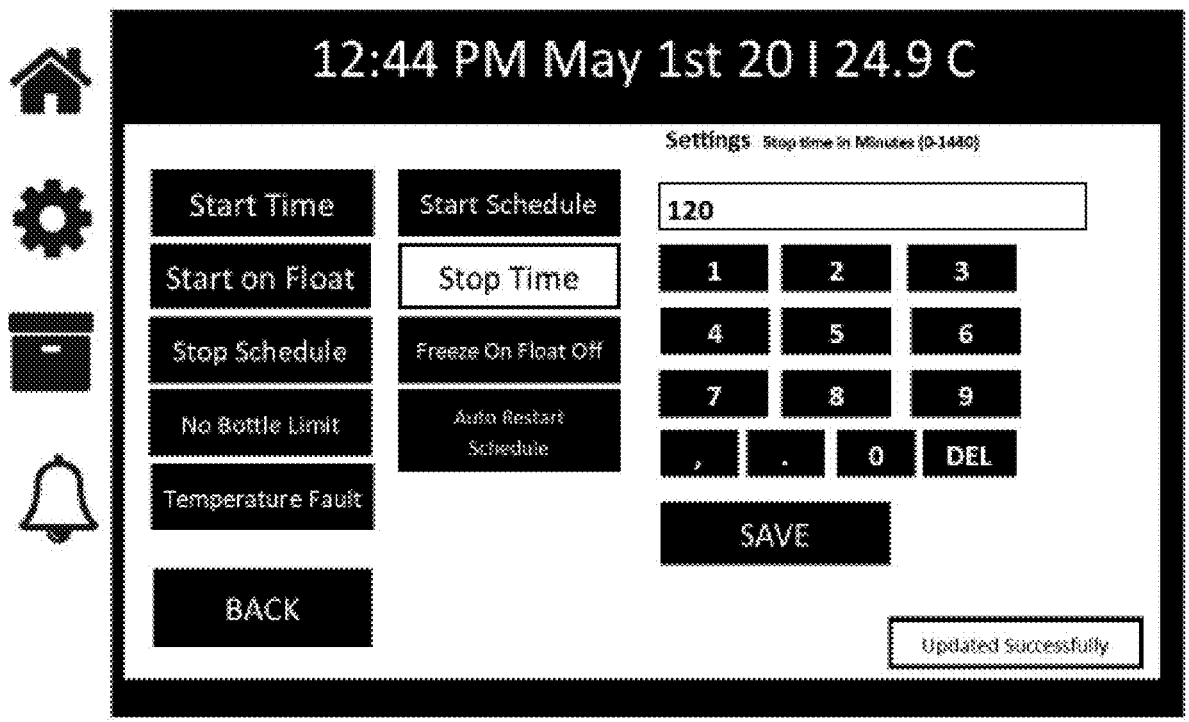

The Stop Time setting is the amount of time the sampler program is to run in minutes. The range is from 0 to 1440 minutes. Press the "Stop Time" button to access the numeric entry keys used to enter the desired amount of time in the window under "SETTINGS" (FIG. 88). Enter the desired time values, press Save, and "Updated Successfully" will appear in the lower right-hand corner if the value is accepted.

Figure 89:
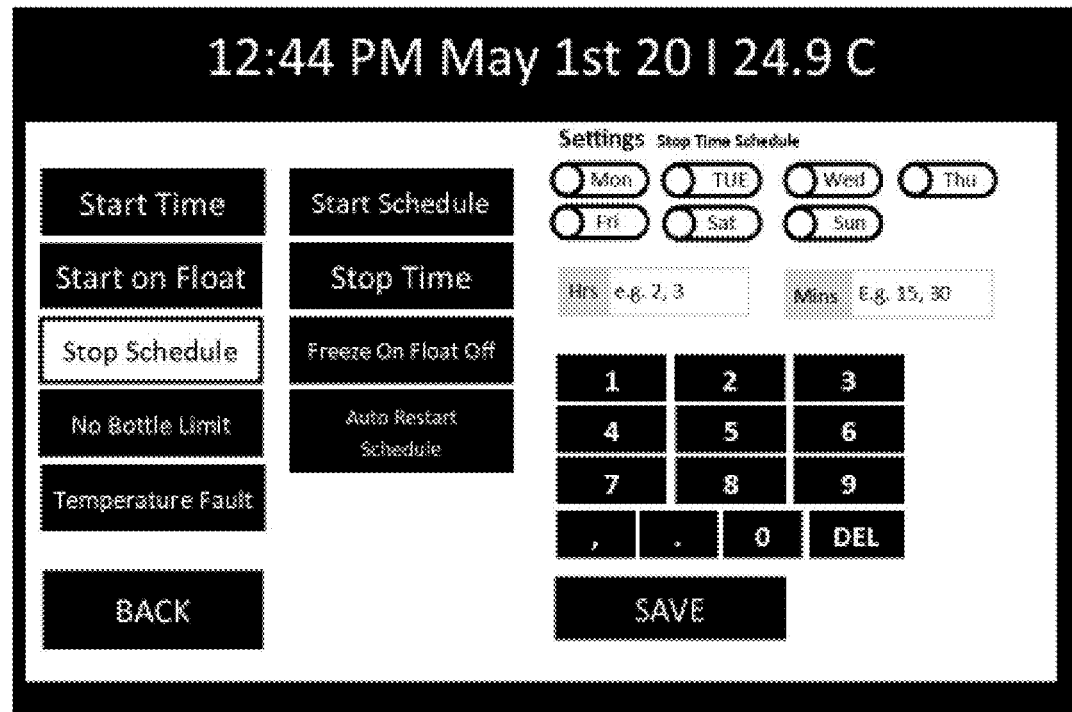
Figure 90:
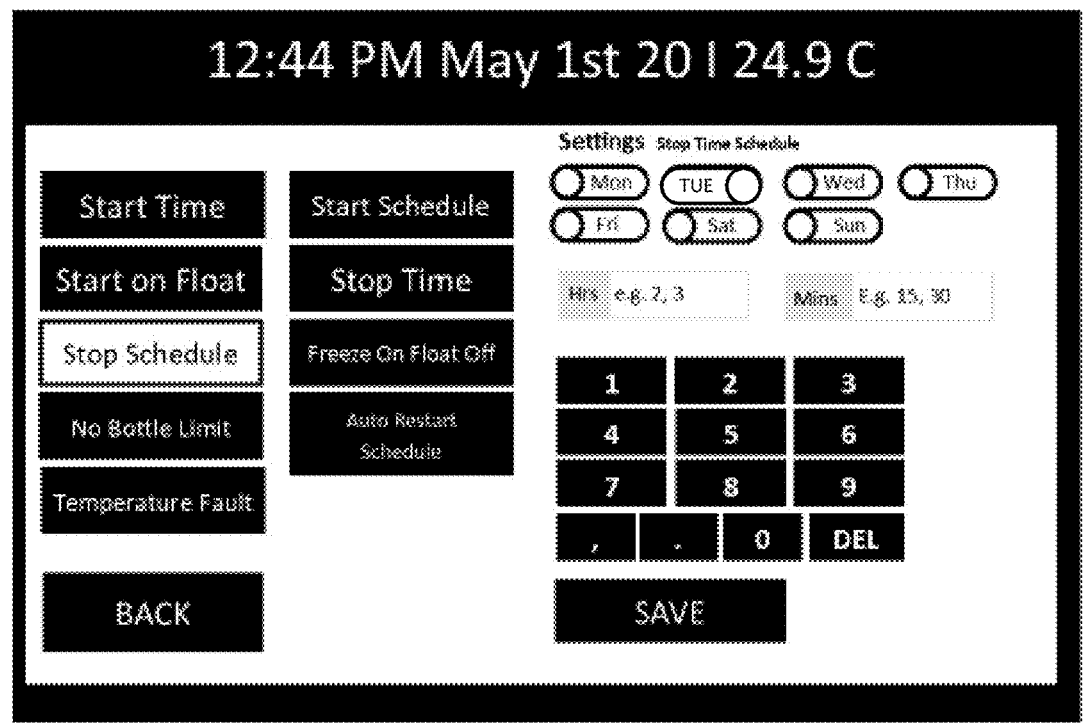
Figure 91:
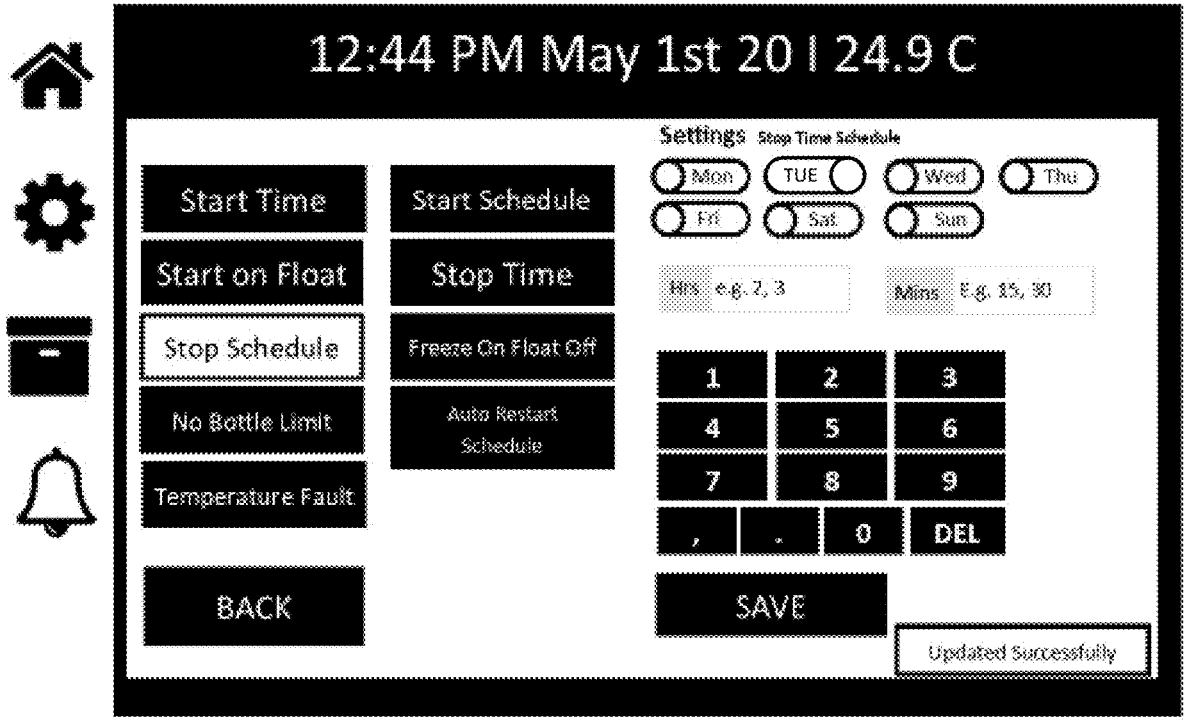

The Stop schedule setting may be used when programing a "Start Schedule". A "Stop Schedule" setting is the day and time the program is to stop running (sampling) (FIG. 89). For example, a programmed "Start schedule" may be scheduled for every Monday at 3:00 pm and to stop on Tuesday at 7:00 am (FIG. 90). Press "Stop Schedule" button to access the numeric entry keys used to enter the stop time in the window under "SETTINGS". Touch the days desired for the program to stop taking samples and they will become active. Enter the Hrs. and Min. in their respective box for the start time. Time entries use 24 hr clock but will be displayed in standard format. After entering the date(s) time(s), press Save, and "Updated Successfully" will appear in the lower right-hand corner if the value is accepted (FIG. 91).

Figure 92:
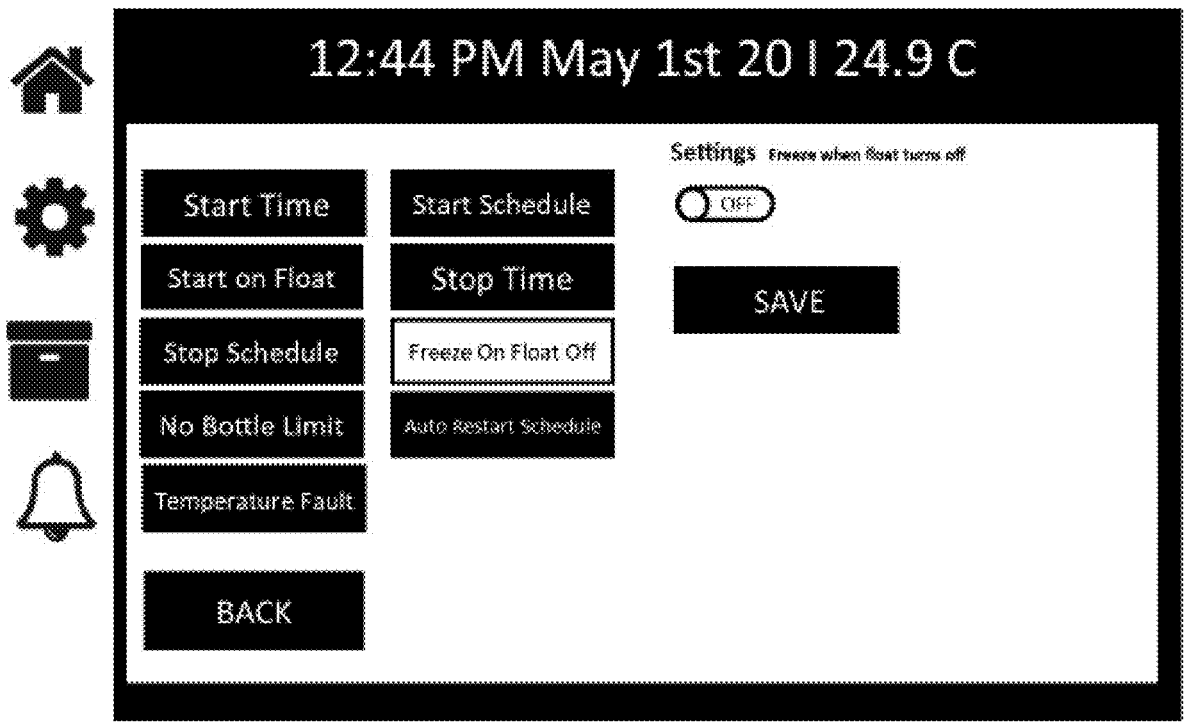

The Freeze On Float Off setting allows running samples based on water levels or pH levels, or any external contact input. When the external contact is closed, the scheduled program will run, when the contact opens, the program will stop. The program will resume every time the contact is closed, or the program is complete, and the sampler shuts off (FIG. 92).

For example, a for stream that does not have running water all the time, it may be desirable to be able to sample the stream when there is water present. Installation of a float will trigger based on a certain level. When that level is reached, the float will close a contact and trigger the sampler to run its program. When the level of the water goes down and the float switch turns off, the sampler stops and when the level rises again the float closes a contact and the sampler runs its program again.

Figure 93:
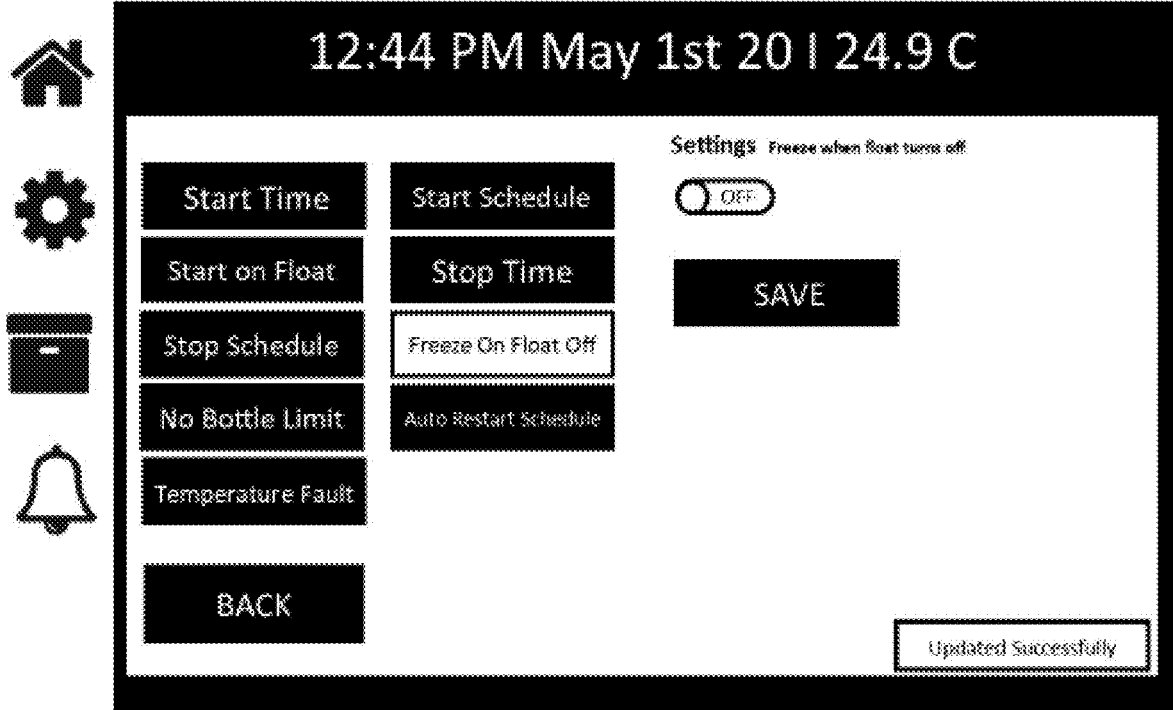

Press "Freeze On Float Off" button to access the numeric entry keys used to select ON/OFF under "SETTINGS". After selecting ON/OFF per your preference press Save, and "Updated Successfully" will appear in the lower right-hand corner if the value is accepted (FIG. 93).

Figure 94:
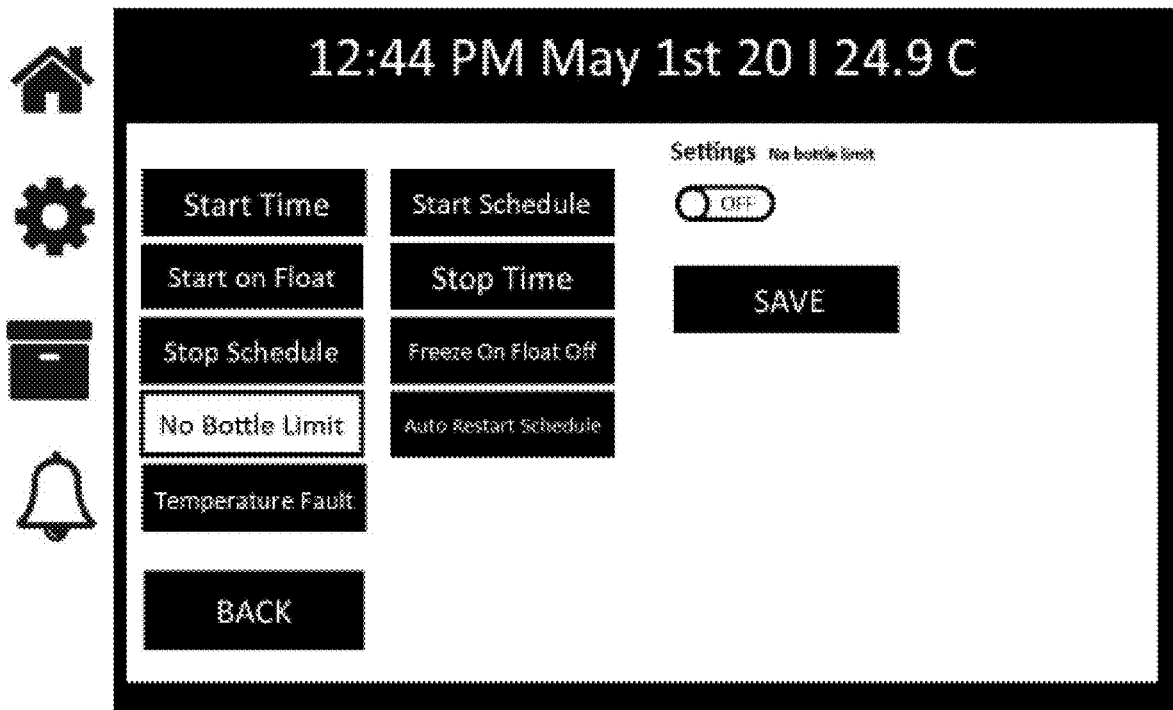
Figure 95:
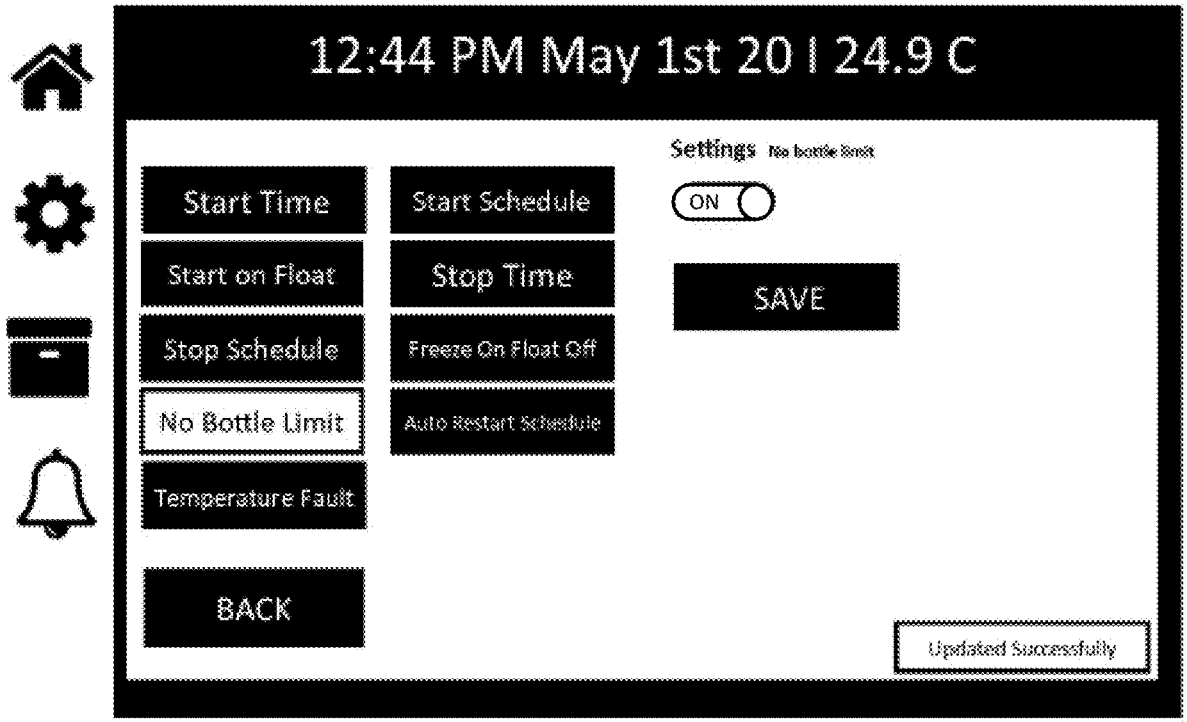

The No Bottle Limit setting allows pulling as may samples as desired per bottle and cancelling out any number in the "Samples Per Bottle" program (FIG. 94). Press the "No Bottle Limit" button to access the window under "SETTINGS". Select the desired setting ON or OFF. After selecting ON/OFF press Save, and "Updated Successfully" will appear in the lower right-hand corner if the value is accepted (FIG. 95).

Figure 96:
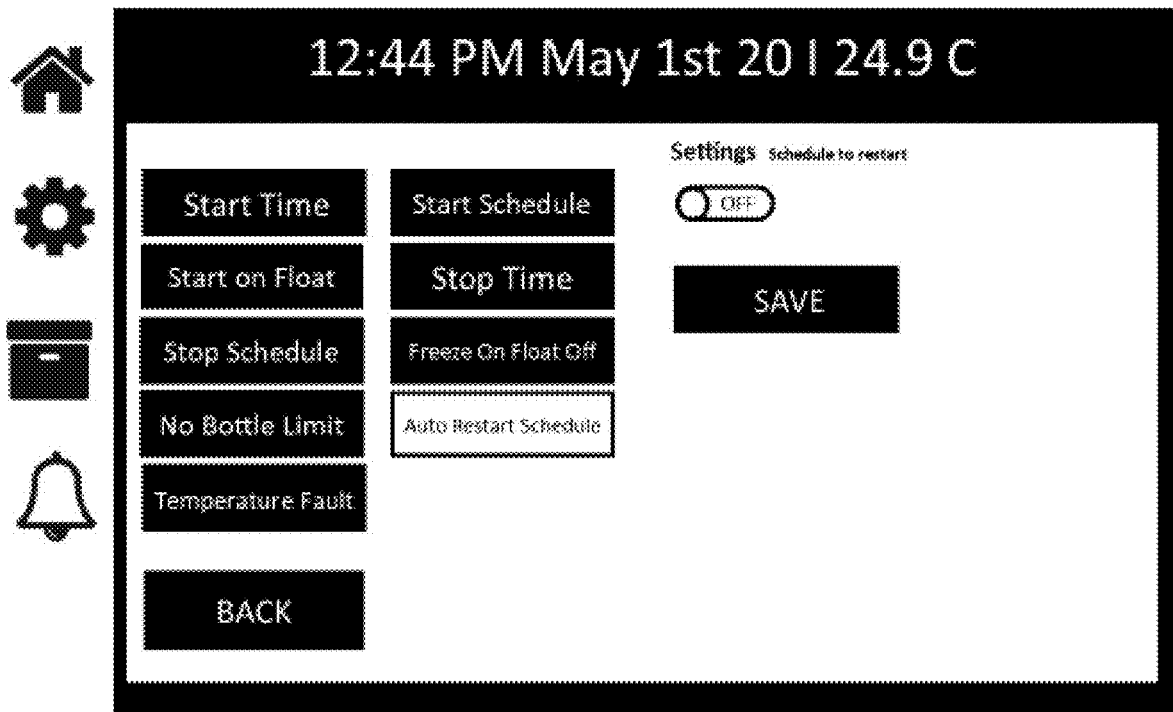
Figure 97:
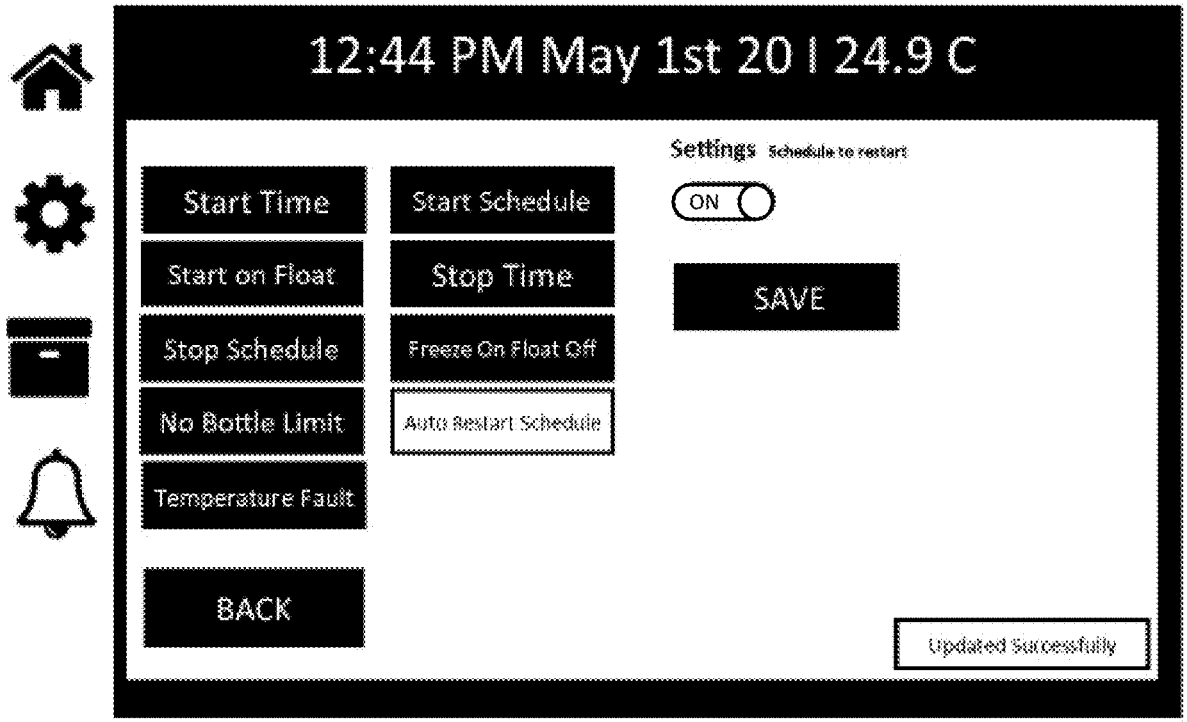

The Auto Restart Schedule setting allows the scheduled programs to run continuously without being reset. By turning this setting ON, the schedule programs will automatically start/start without being manually reset. Select the desired setting ON or OFF (FIG. 96). After selecting ON/OFF per your preference press Save, and "Updated Successfully" will appear in the lower right-hand corner if the value is accepted (FIG. 97).

Figure 98:
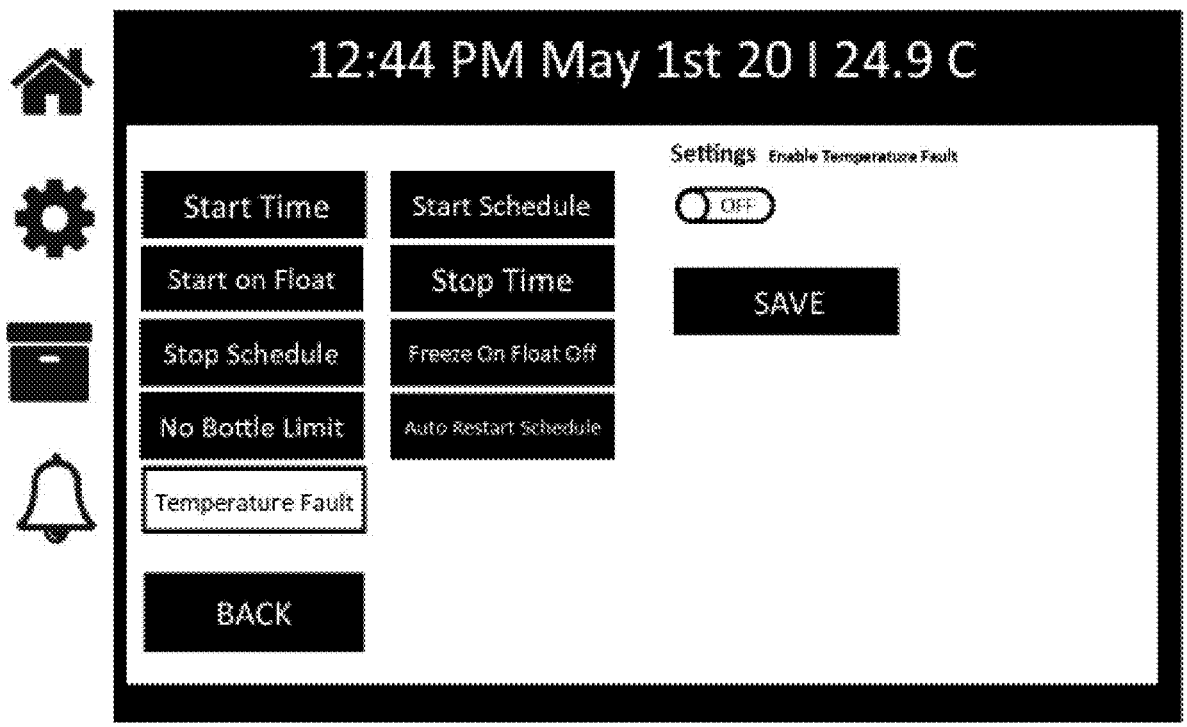

Temperature Fault setting provides an alarm output if the Temperature gets above a set level for a set period of time (FIG. 98).

Figure 99:

When the "ADVANCED" programming is completed, all the selections can viewed and verified under the ADVANCED TAB on the Home screen (FIG. 99).

Figure 100:
FIGS. 100-146 are program settings screens of the present invention.

The sampler may include a program will be set up for time-based sampling. It may be modified as desired for specific needs. At start up the Home screen will be displayed (FIG. 100). This may be the screen from which all programs may be started and stopped, and all program settings may be viewed under their respective setting TABS.

Figure 101:
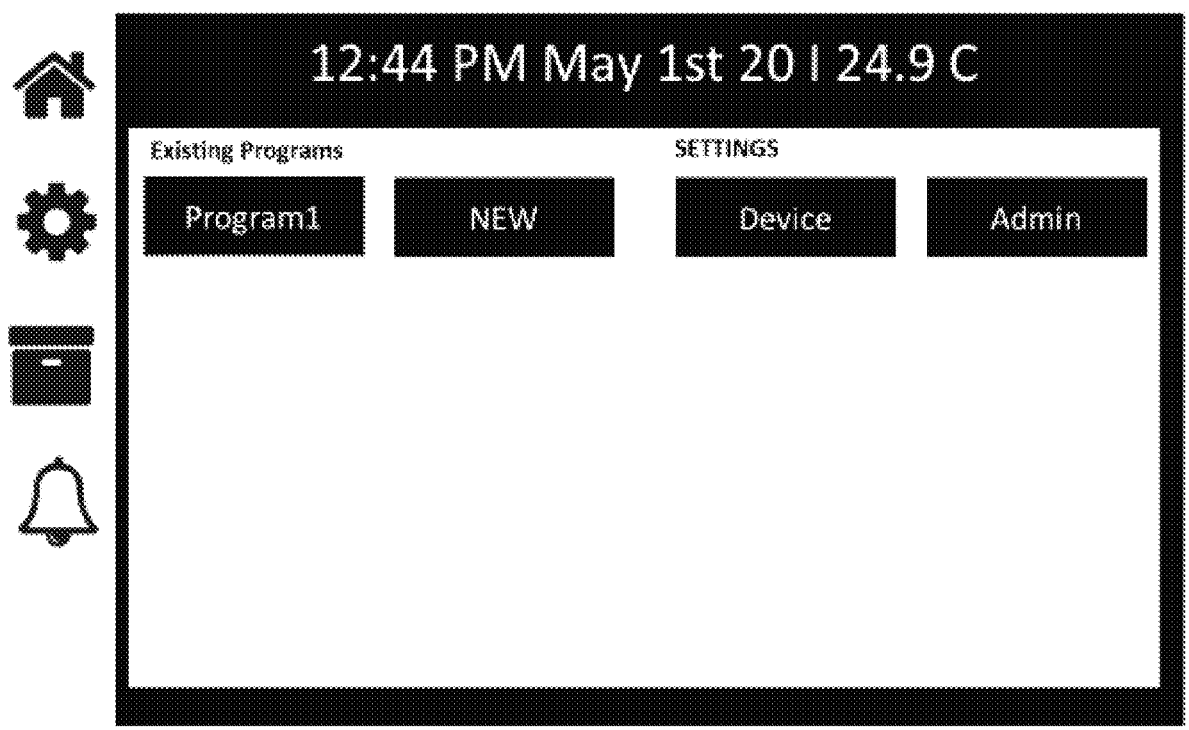
Figure 102:
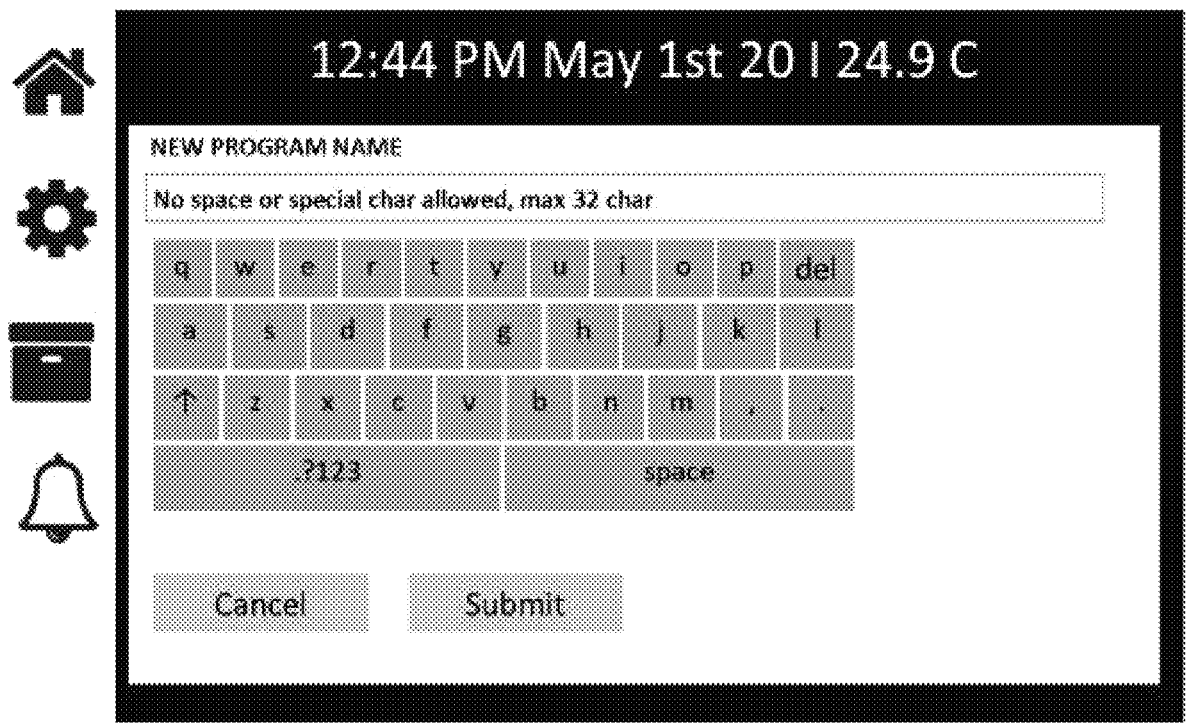
Figure 103:
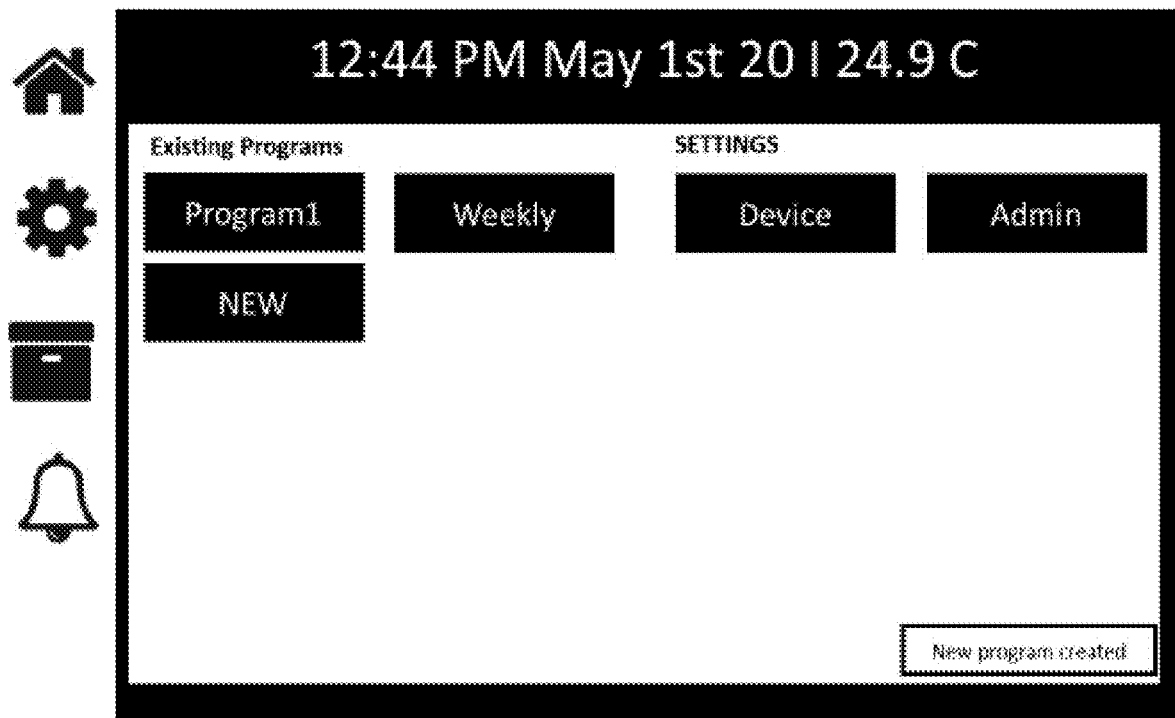

To set up a NEW Program, press the Configuration icon on the left of the Home screen and it will advance to the "EXISTING PROGRAMS" screen (FIG. 101). Press the "NEW" program button to change to the keyboard display and prompt to change (type in) the name of the new program (FIG. 102). After a new name is typed in the window ("weekly" for example) and the "SUBMIT" button is pressed, the "EXISTING PROGRAMS" screen is displayed (FIG. 103). On the "EXISTING PROGRAMS" screen the "new program created" banner will be displayed in the lower right corner and a button with the name of the new program "weekly" will be displayed next to the "Program1" button.

Figure 104:
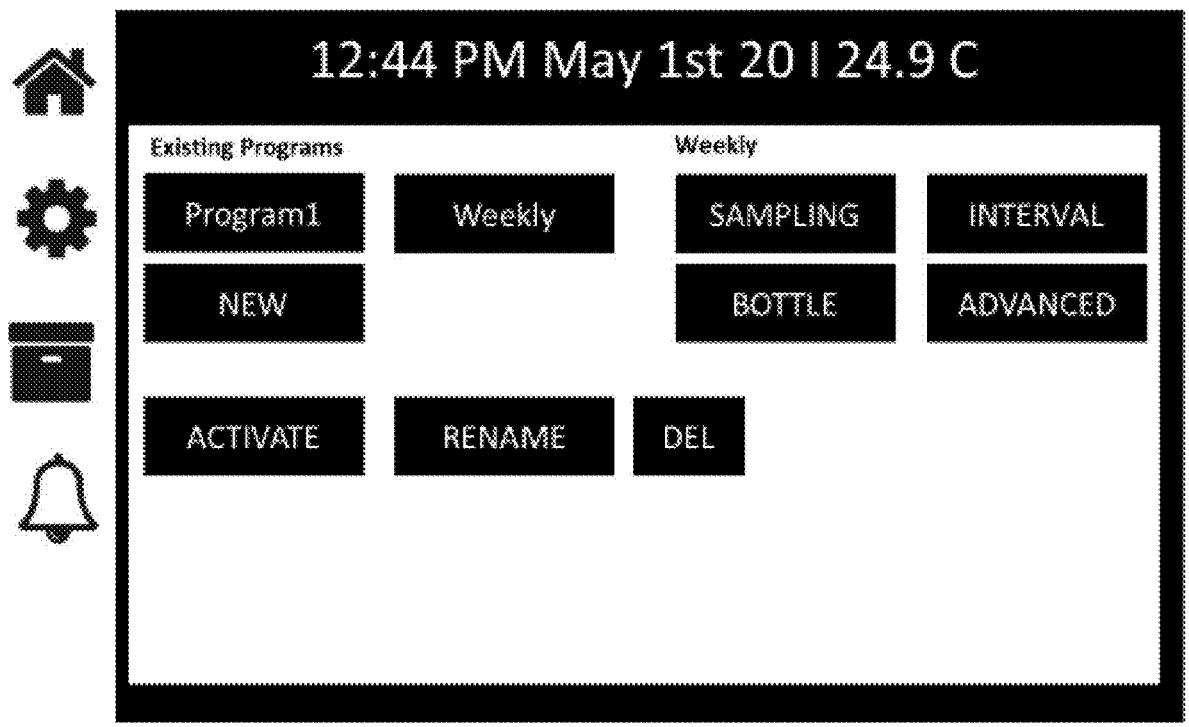

To begin building the new program, press the "weekly" program button and it will be highlighted to indicate it is active. From this screen you may also ACTIVATE, RENAME, or DELETE (DEL) any program listed (FIG. 104). Pressing the "weekly" button allows access to and change of the four settings of the program: SAMPLING, INTERVAL, BOTTLE, and ADVANCED. The process is the same as changing or modifying an existing program, which is described hereinabove.

Figure 105:
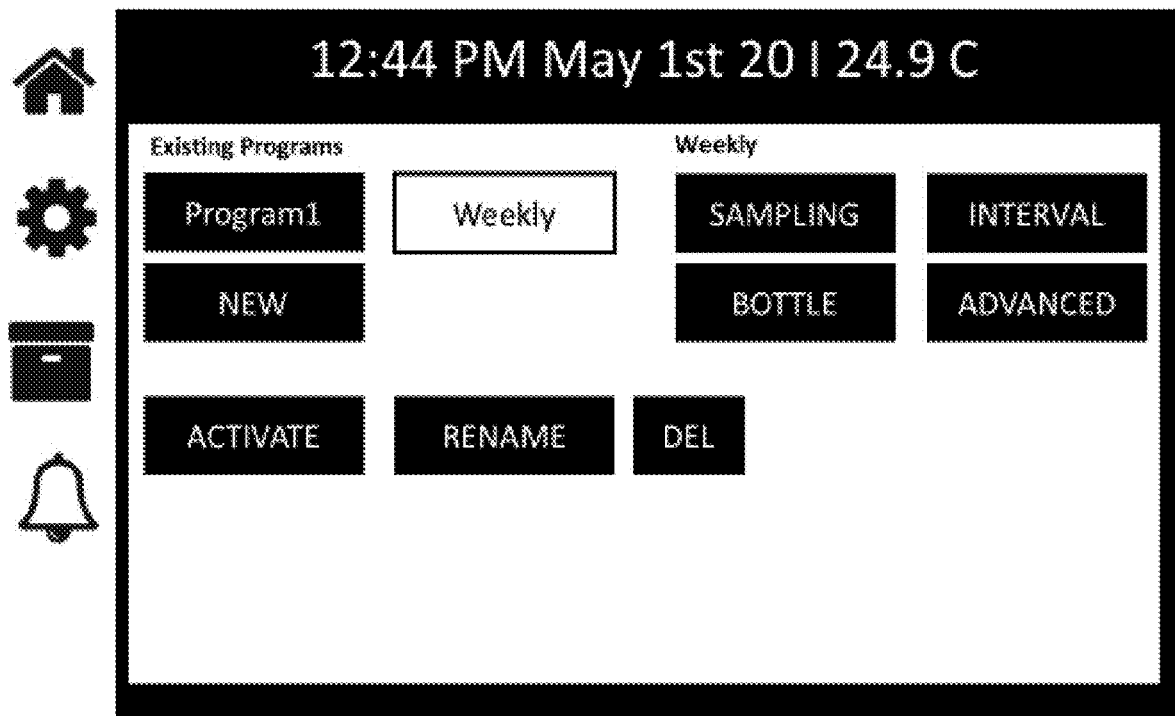
Figure 106:
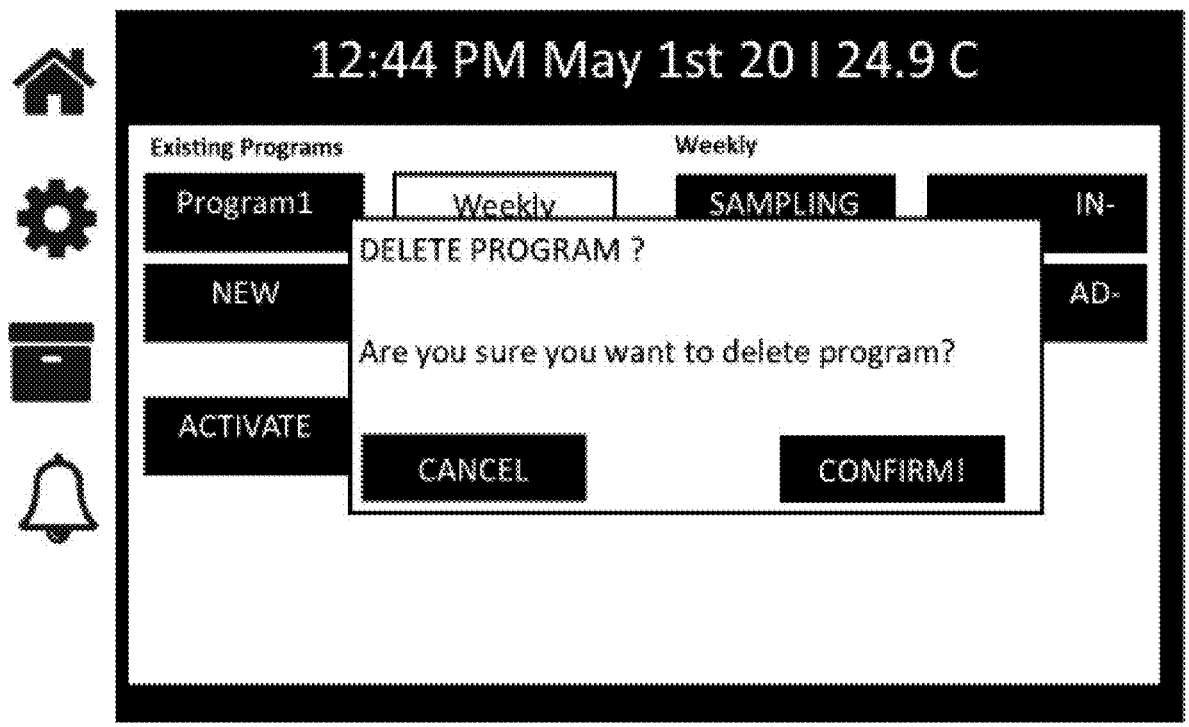

The Deleting Programs setting allows the easy removal of an existing or newly created program from the unit. By pressing the program button that you want to remove you will be prompted to select ACTIVATE, RENAME or DEL (FIG. 105). Press the "DEL" button and confirmation to delete the program with a popup or cancel will be displayed (FIG. 106). Press confirm to delete the program.

Figure 107:
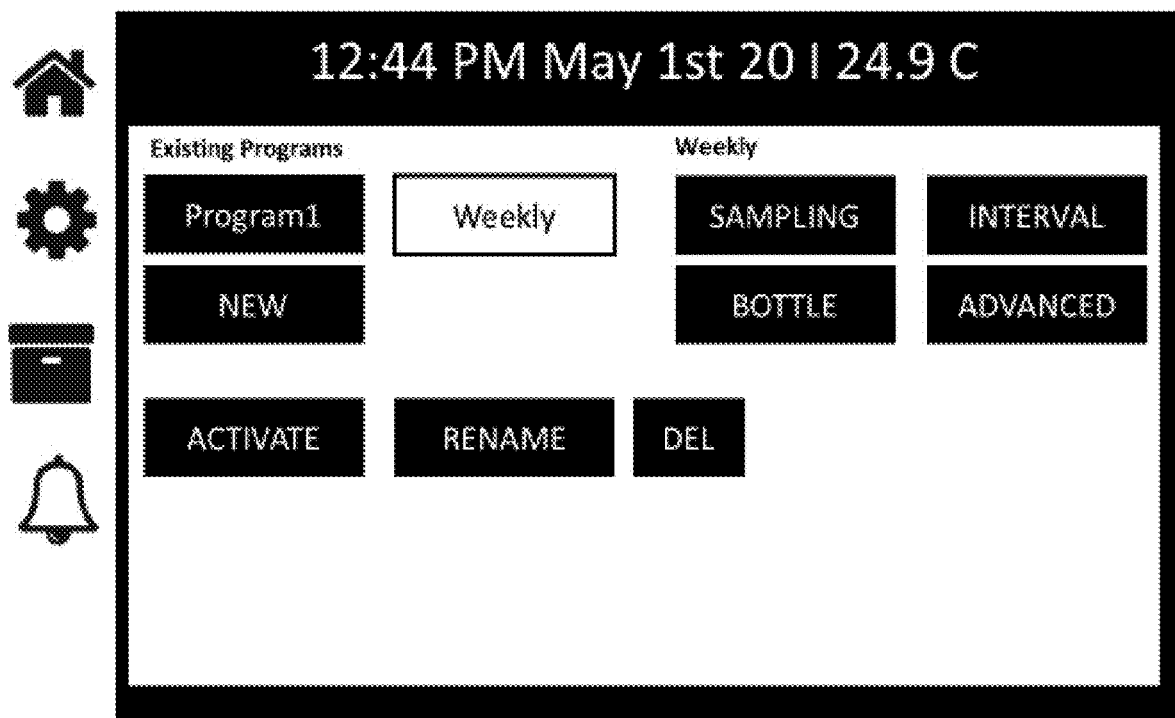
Figure 108:
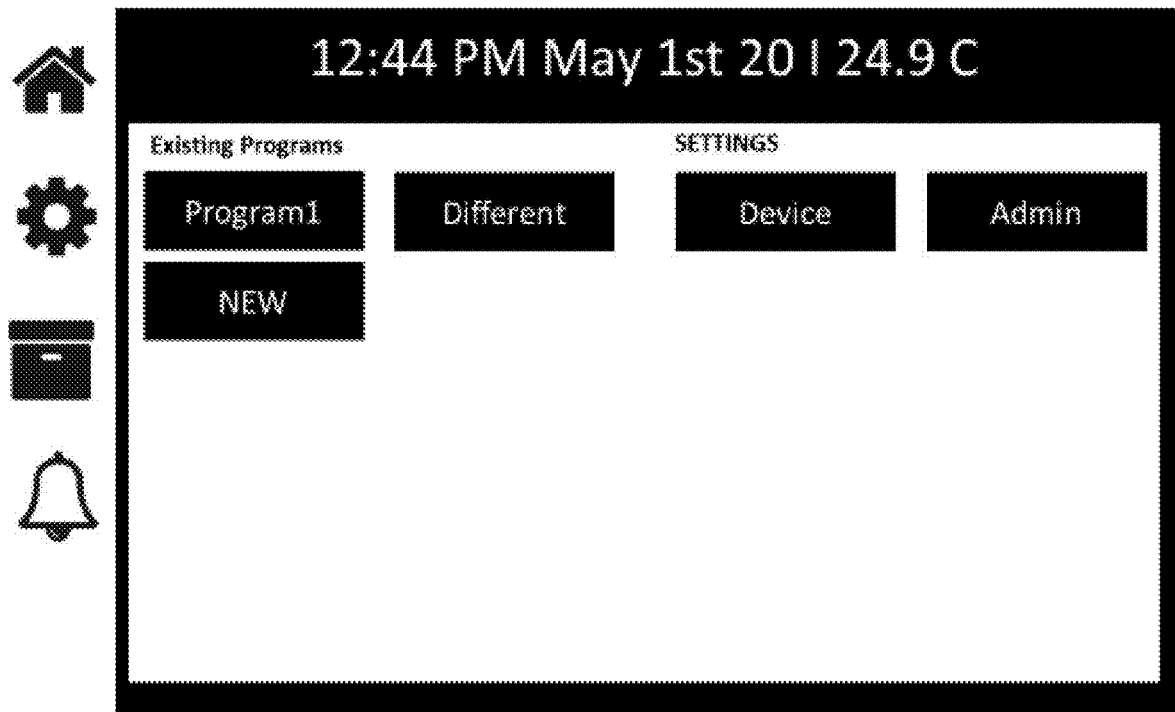

The Rename Program setting allows the easy renaming of a program (FIG. 107). If the new program name was misspelled or a different name is desired, select the desired button, press rename and correct/rename the program (FIG. 108). Press confirm to accept the changes.

Figure 109:
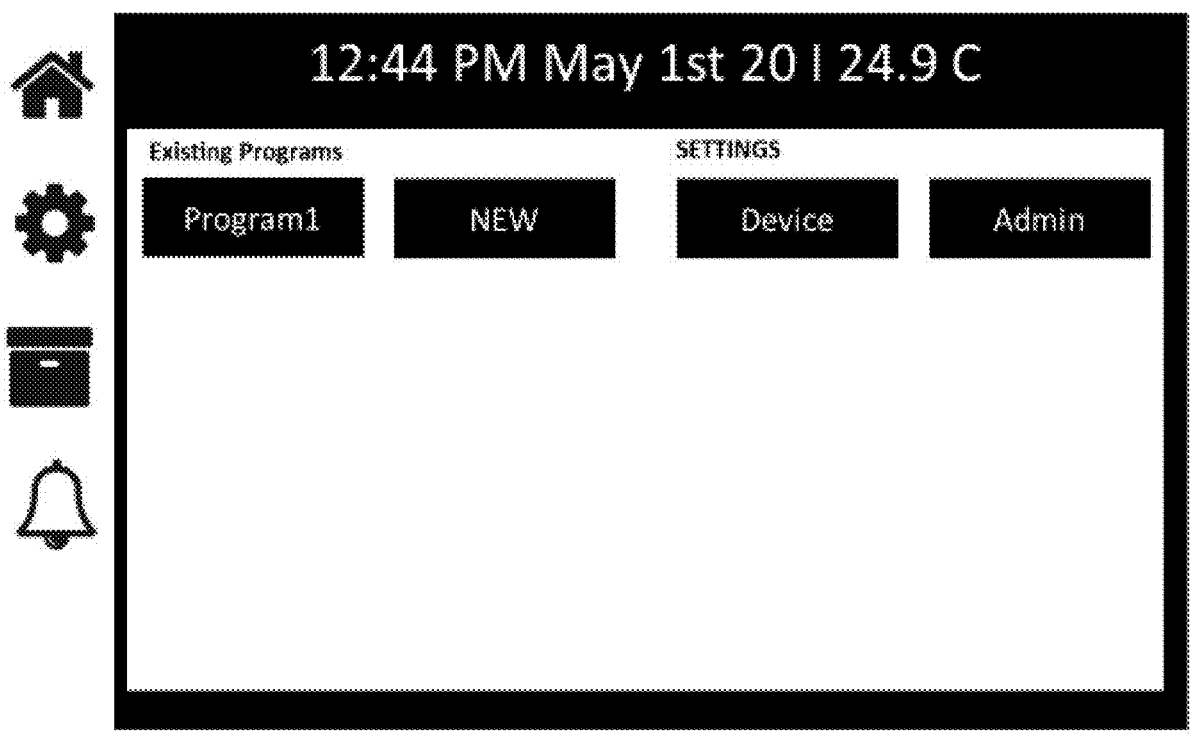
Figure 110:
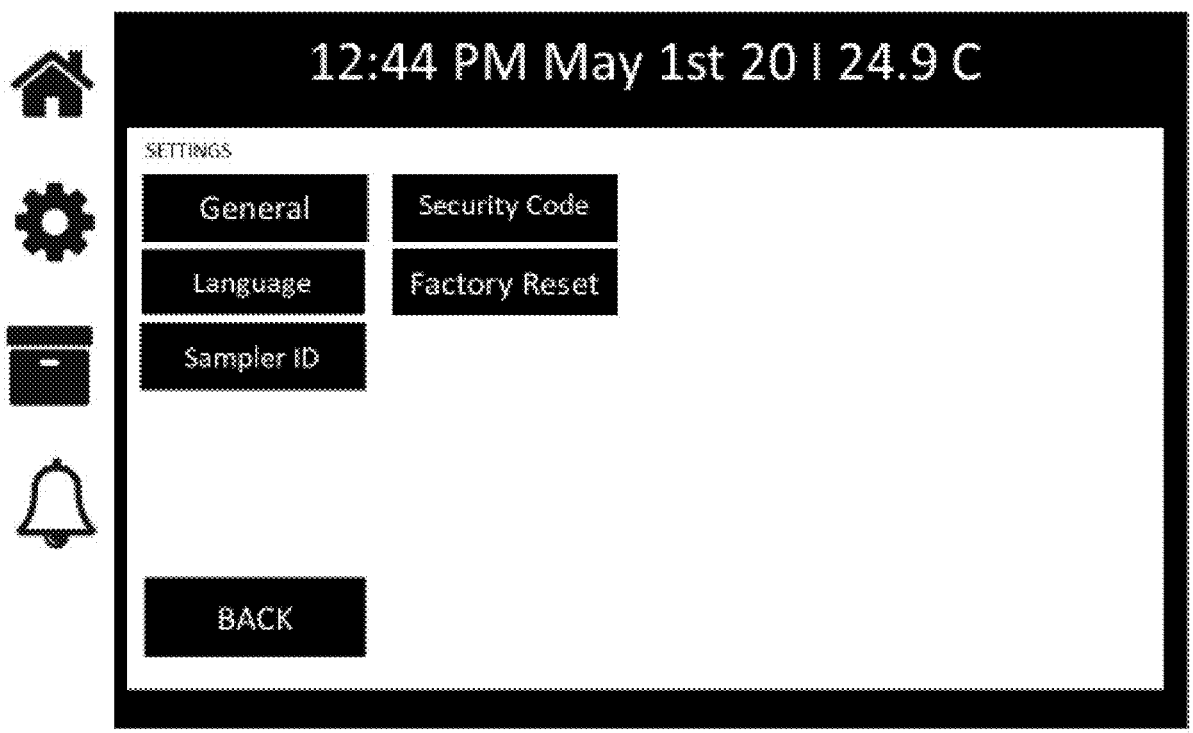
Figure 111:
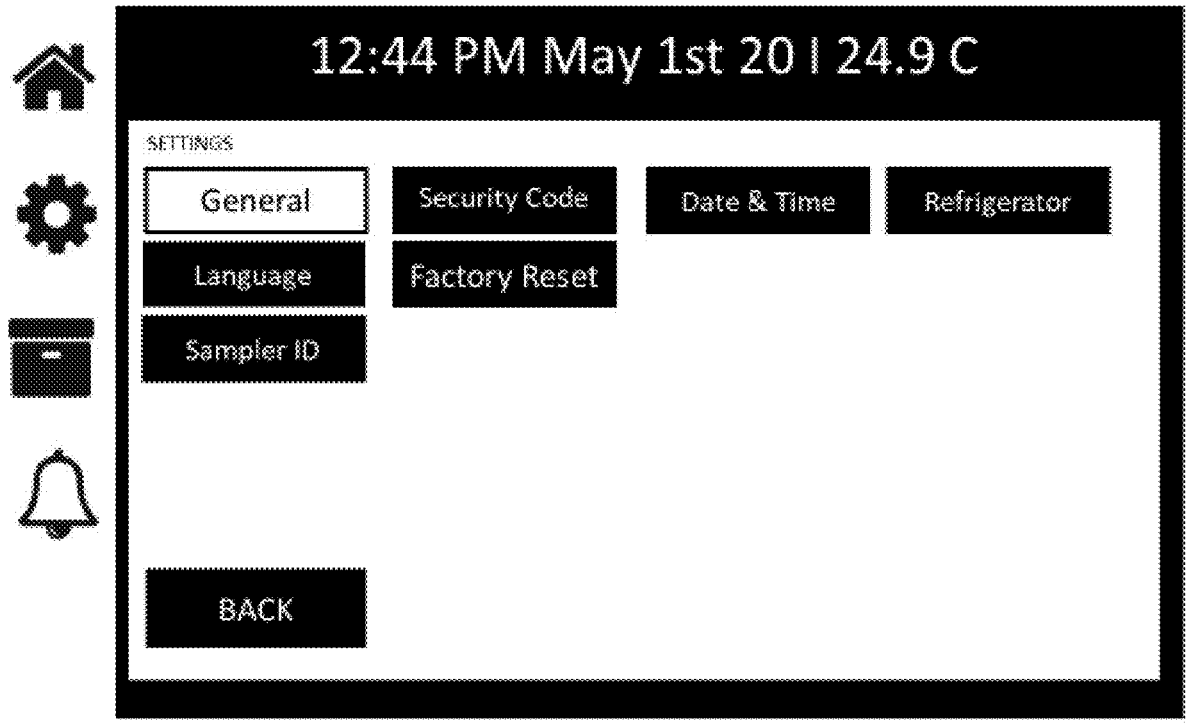
Figure 112:
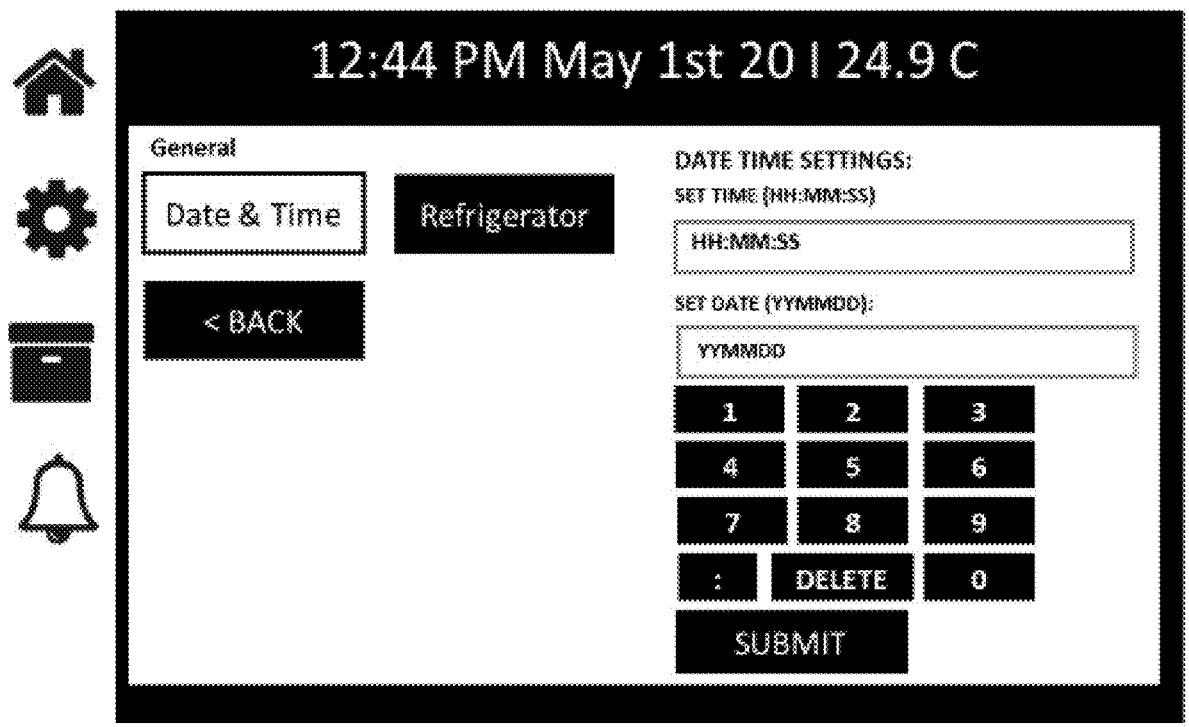
Figure 113:
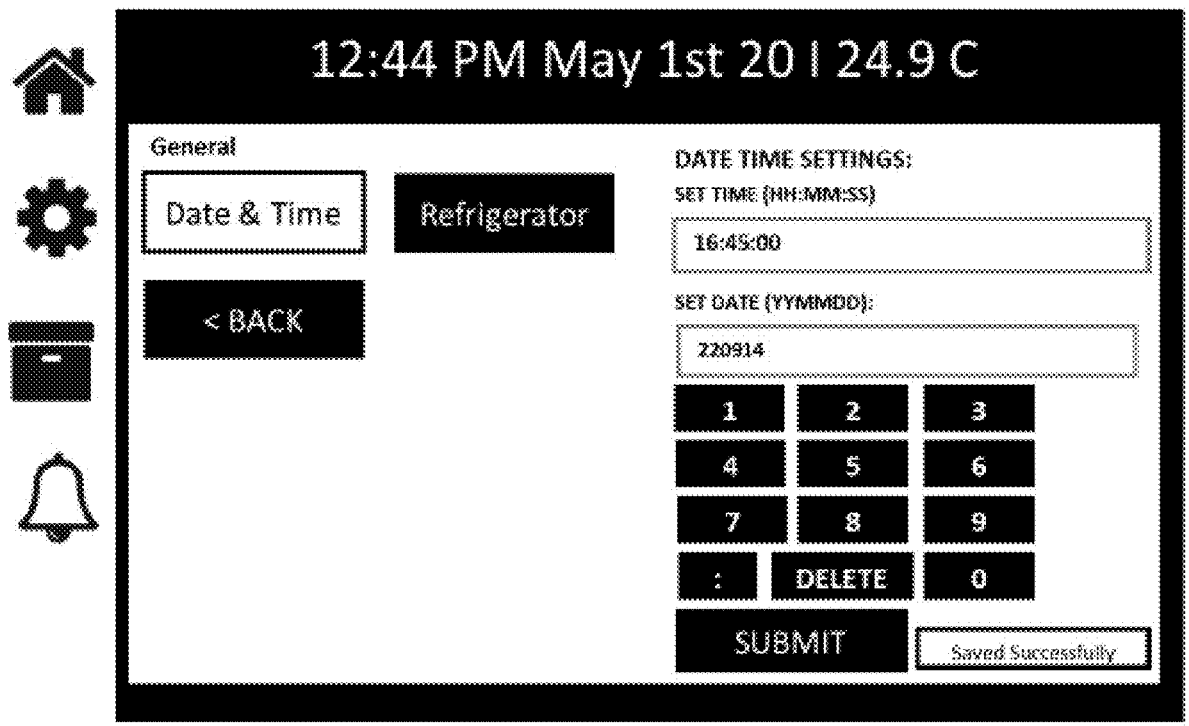

To access the device settings (FIG. 109), press Device (FIG. 110). The General area allows setup of Date & Time and access the Refrigerator temperature adjustment screens (FIG. 111). The General menu can be accessed while the program is running. To update the Date & Time select the Date & Time button (FIG. 112). Once the Date & Time are entered, press Submit, and Saved Successfully will appear in the lower right-hand corner of the screen (FIG. 113). The Date & Time will show up at the top of the screen.

Figure 114:
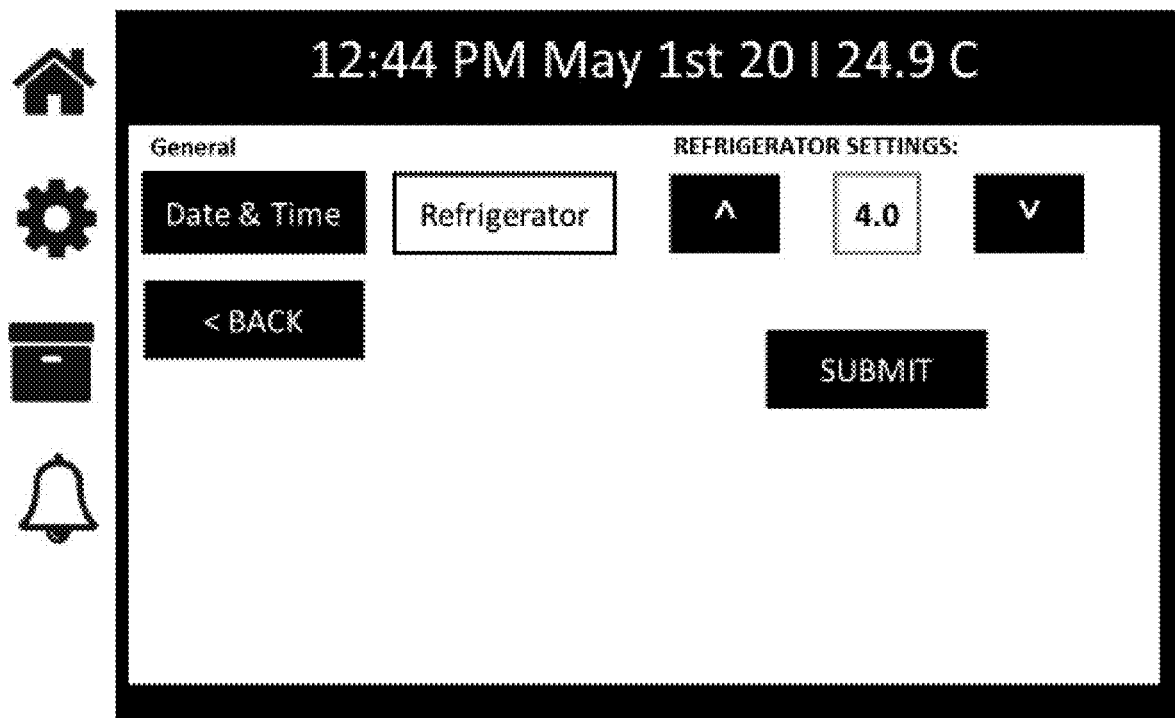
Figure 115:
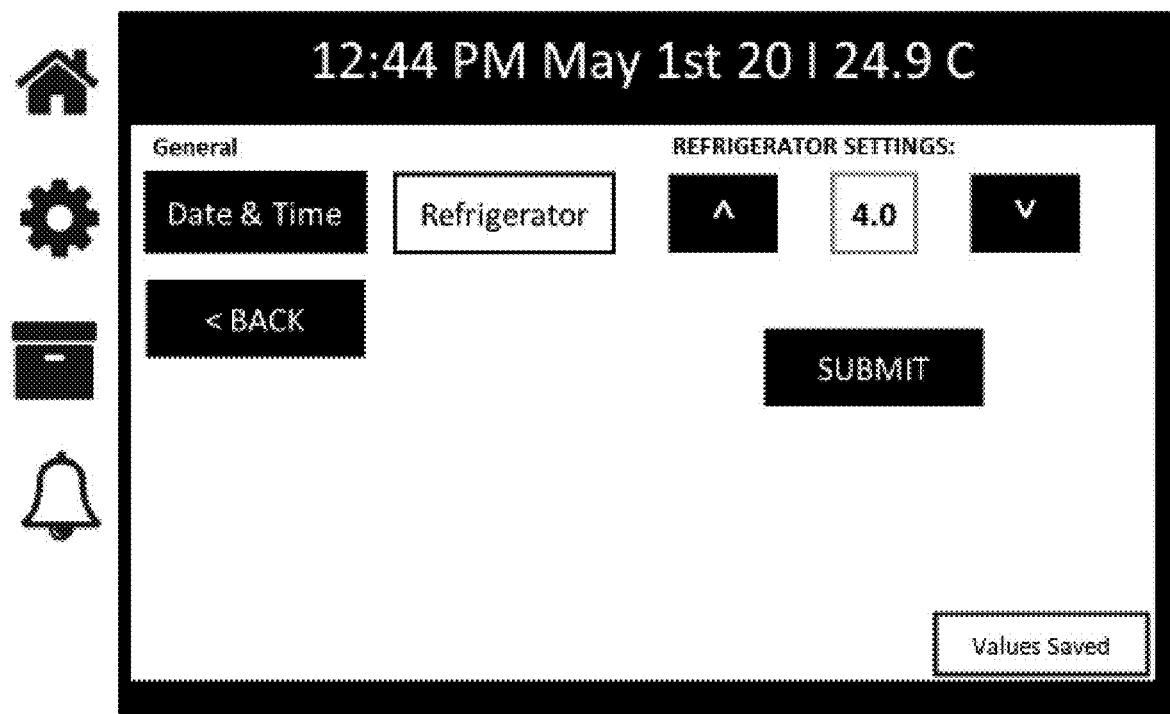

The Refrigerator settings is to adjust the inside temperature of the cabinet (FIG. 114). Pressing A raises the temperature and v lowers the temperature. Adjust the settings and press Submit to save. Values Saved will appear in the bottom Right Hand side (FIG. 115). The number does not represent the cabinet temperature but is a reference number to use to set the temperature. The refrigerator setting can be accessed in the General menu while a program is running.

Figure 116:
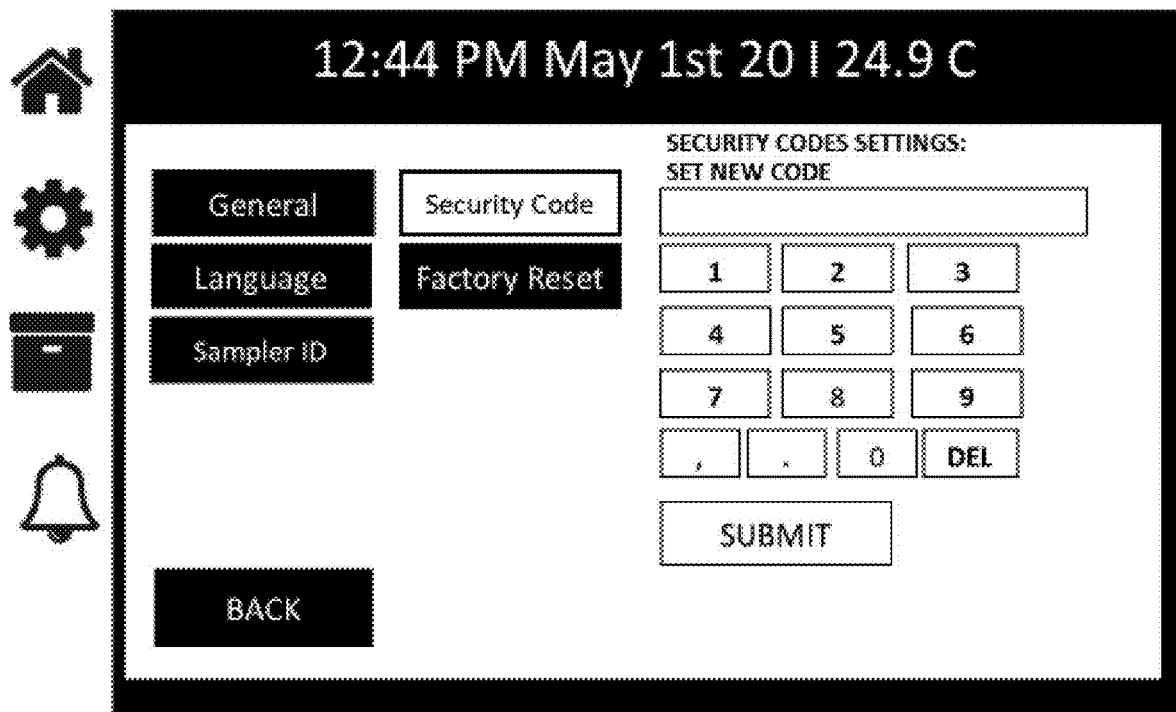
Figure 117:
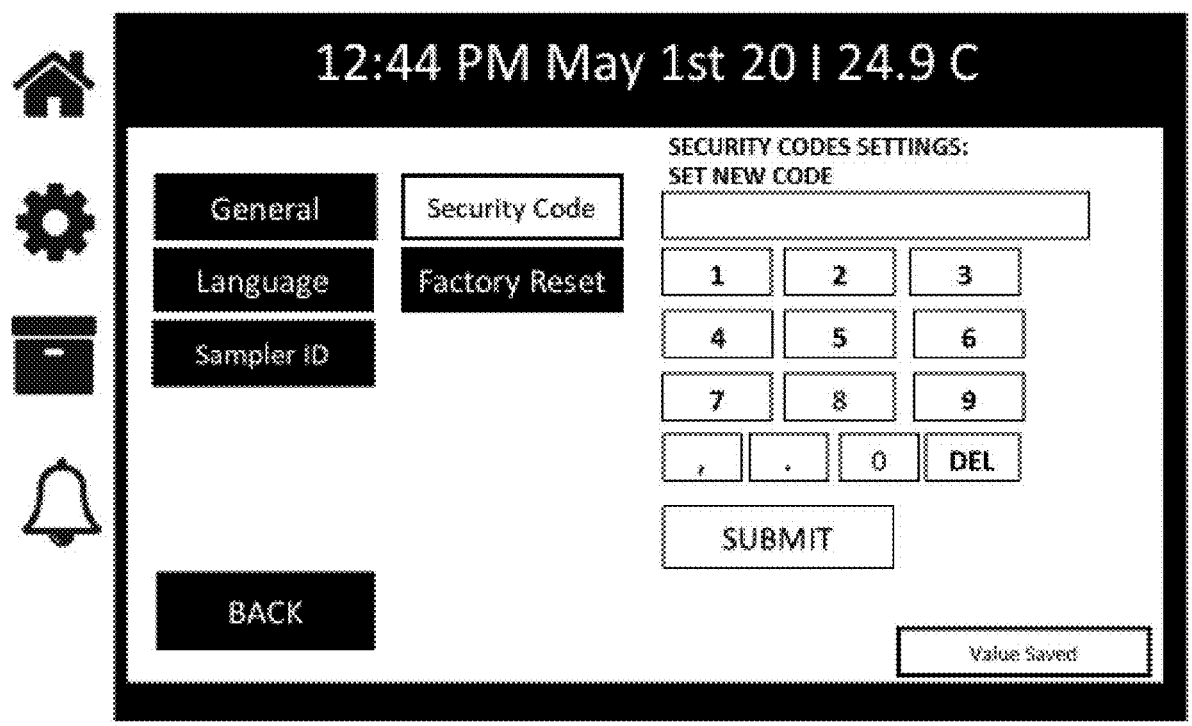
Figure 118:
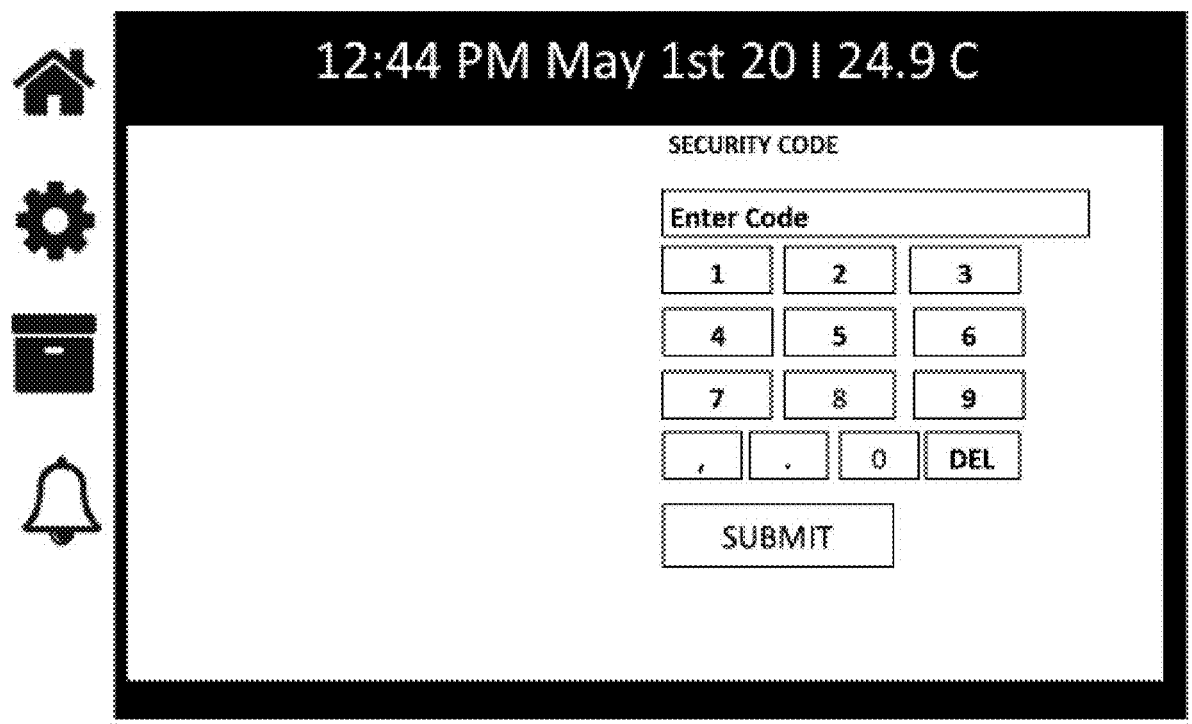

The Security Code setting is used to prevent unauthorized personnel from tampering with the program Settings menu (FIG. 116). If a Security Coder is desired, press Security Code, it will be highlighted, and the numeric entry screen will appear. Enter the desired numeric code and press Submit. Value Saved will appear in the lower right-hand corner (FIG. 117). Once set, this code will be required to be entered to access the Settings (FIG. 118).

Figure 119:
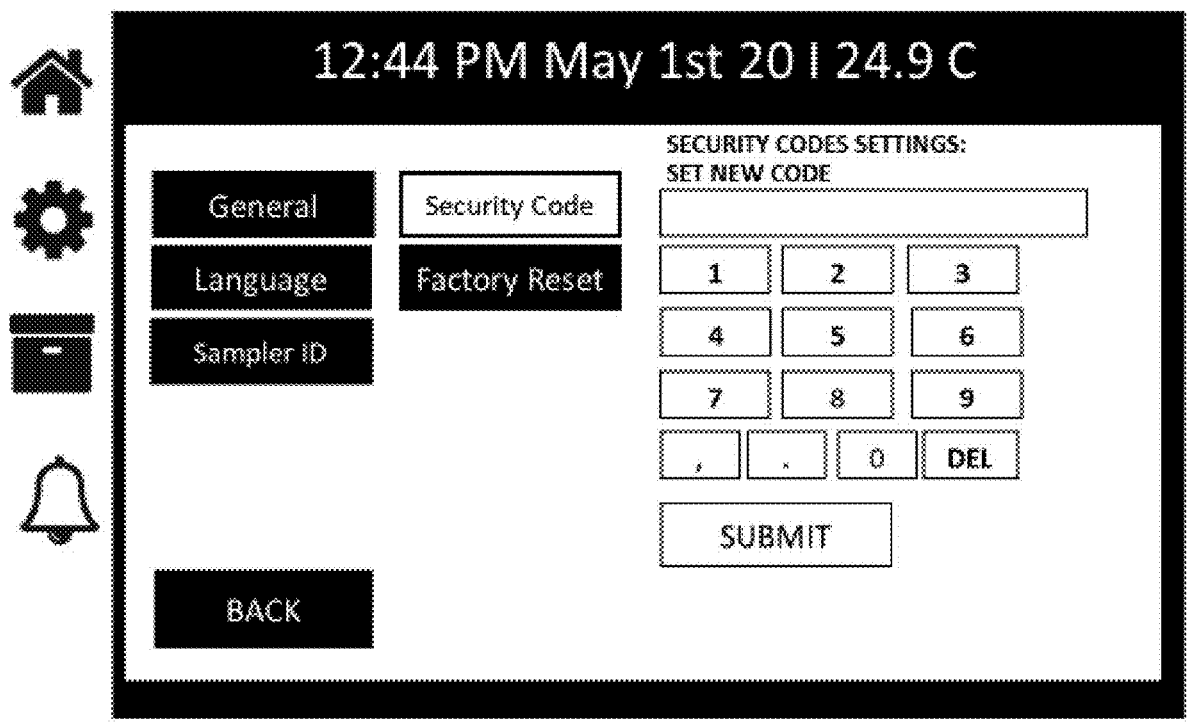

The sample programs will continue to run or shut off according to the program, but Settings cannot be accessed until the security code is entered. If a Security Code is not used leave it blank. When a Security code is activated and have returned to the Home Screen, the security code is activated. Pressing the Configuration Icon will take you to a Security Code screen (FIG. 119). To enter the settings screens, enter the Security Code that was entered previously. If a Security Code was entered, but needs to be removed, enter the Security Code to access settings, press Device and Security Code. Enter 0000, This Code will remove an existing code and disable the Security Code.

Figure 120:
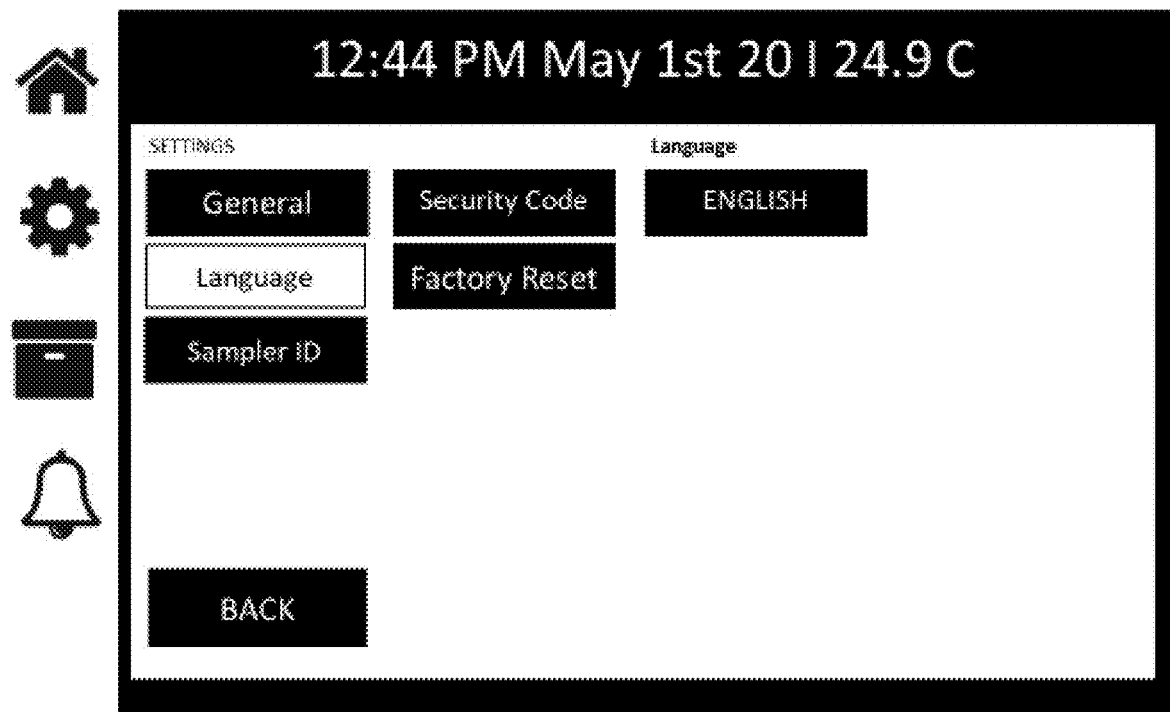

Select Language to set the display language (FIG. 120).

Figure 121:
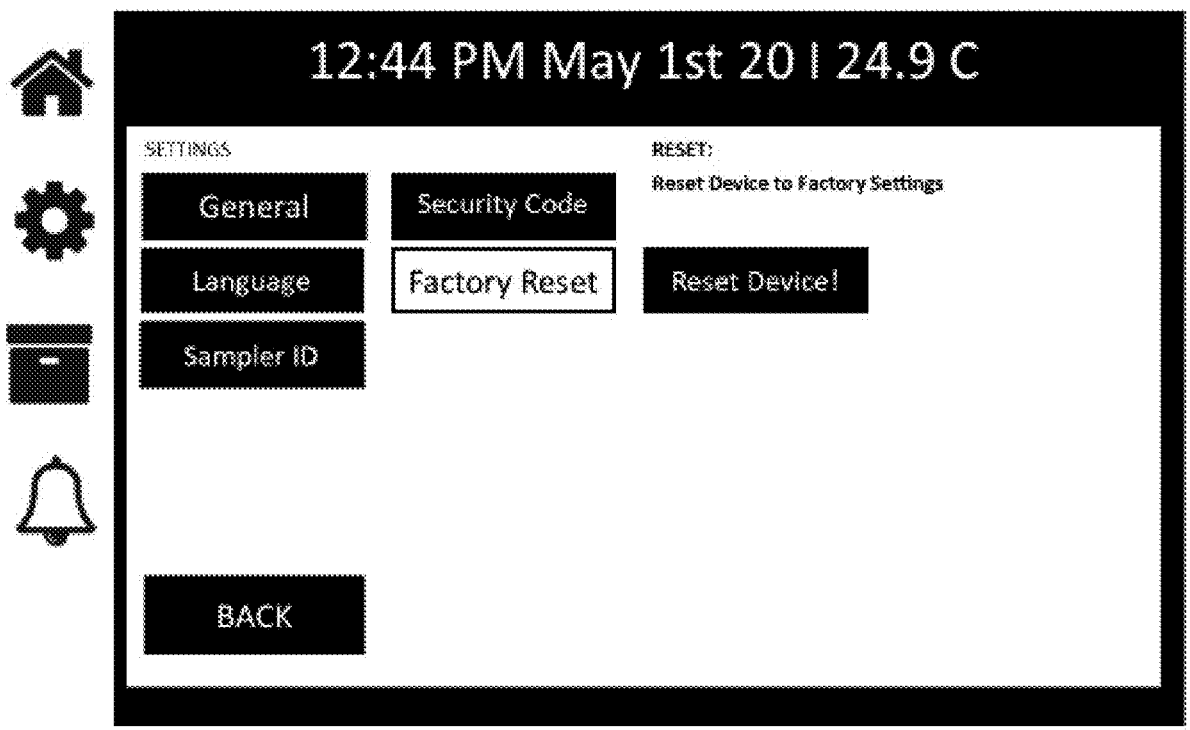
Figure 122:
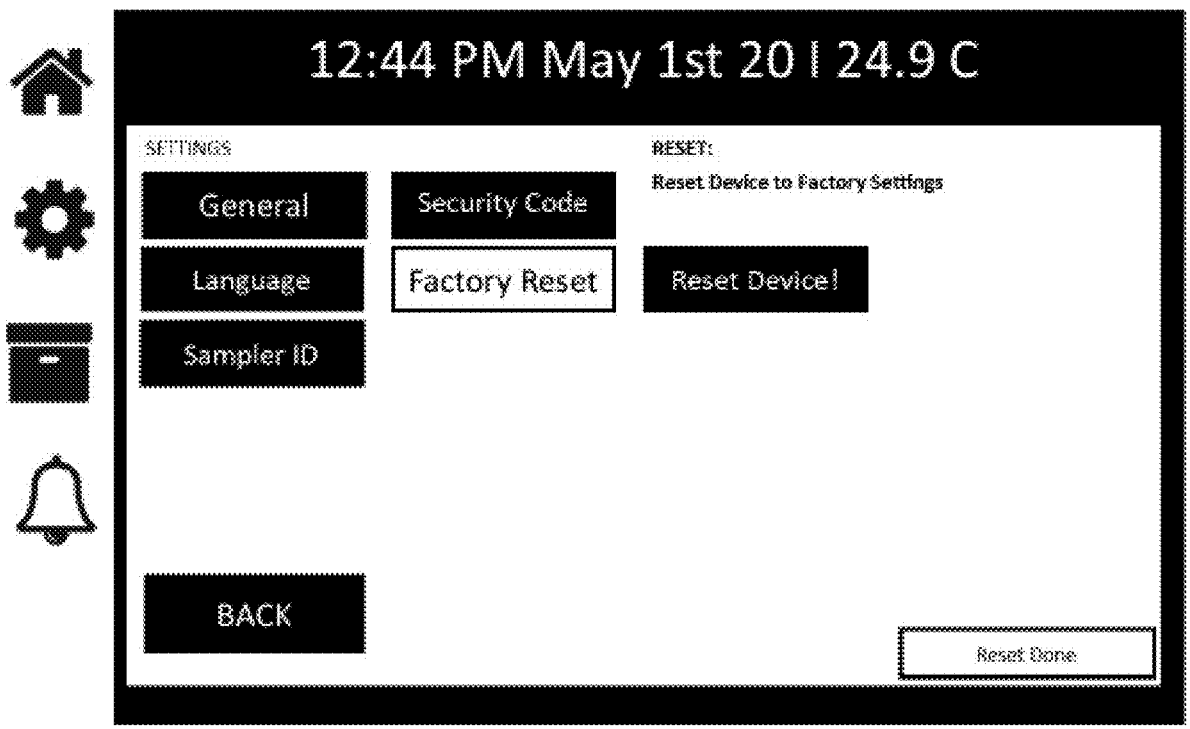
Figure 123:
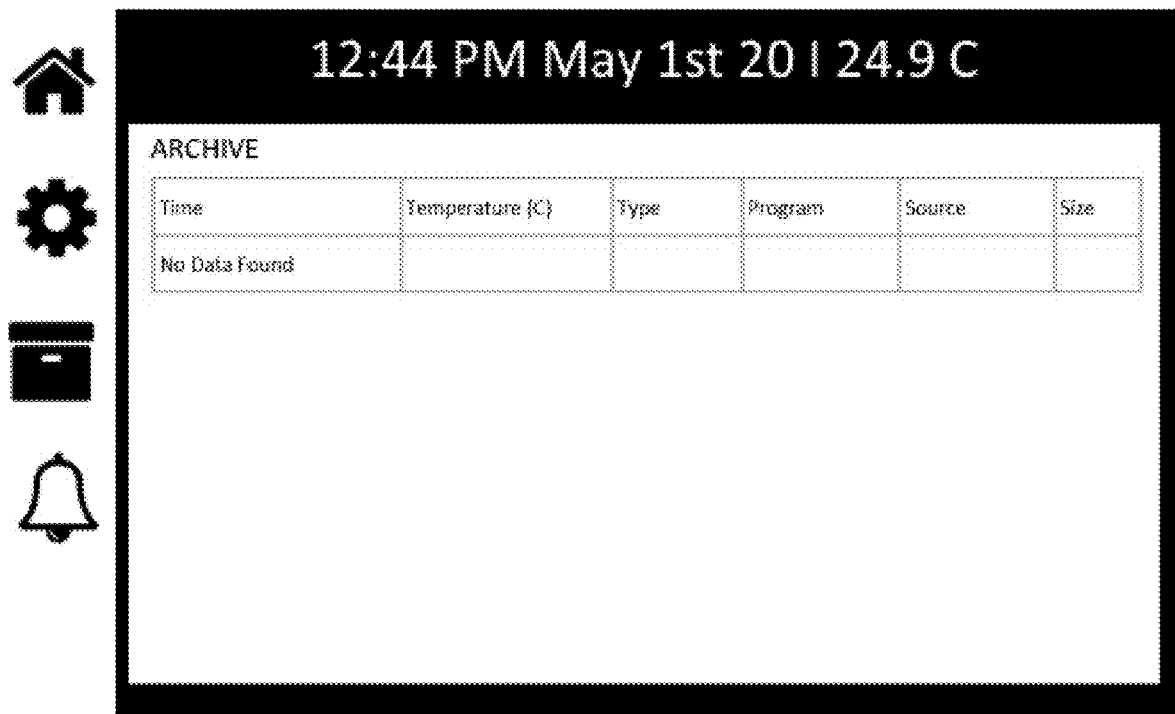

The Factory Reset setting is used to clear all the Log files (FIG. 121). When you press Reset Device!, Reset Done will appear in the lower right-hand corner (FIG. 122). The log files will be permanently removed (FIG. 123).

Figure 124:
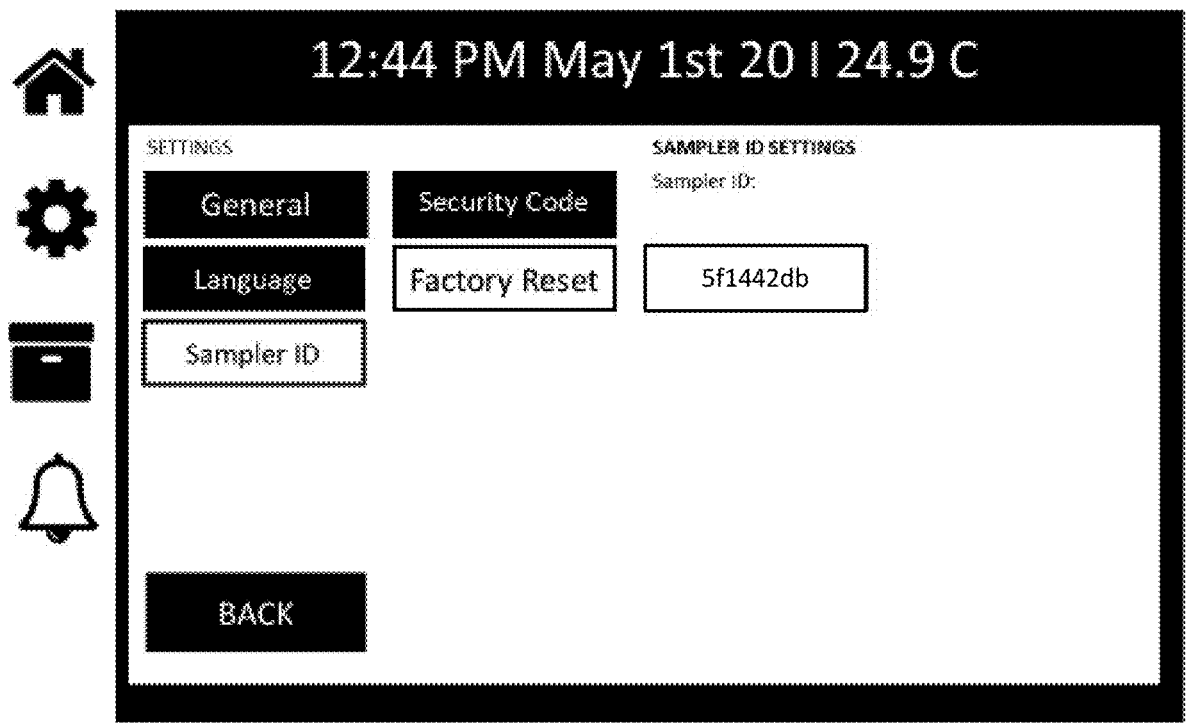

The Sampler ID setting displays a unique number based on the processor inside the apparatus (FIG. 124).

Figure 125:
Figure 126:
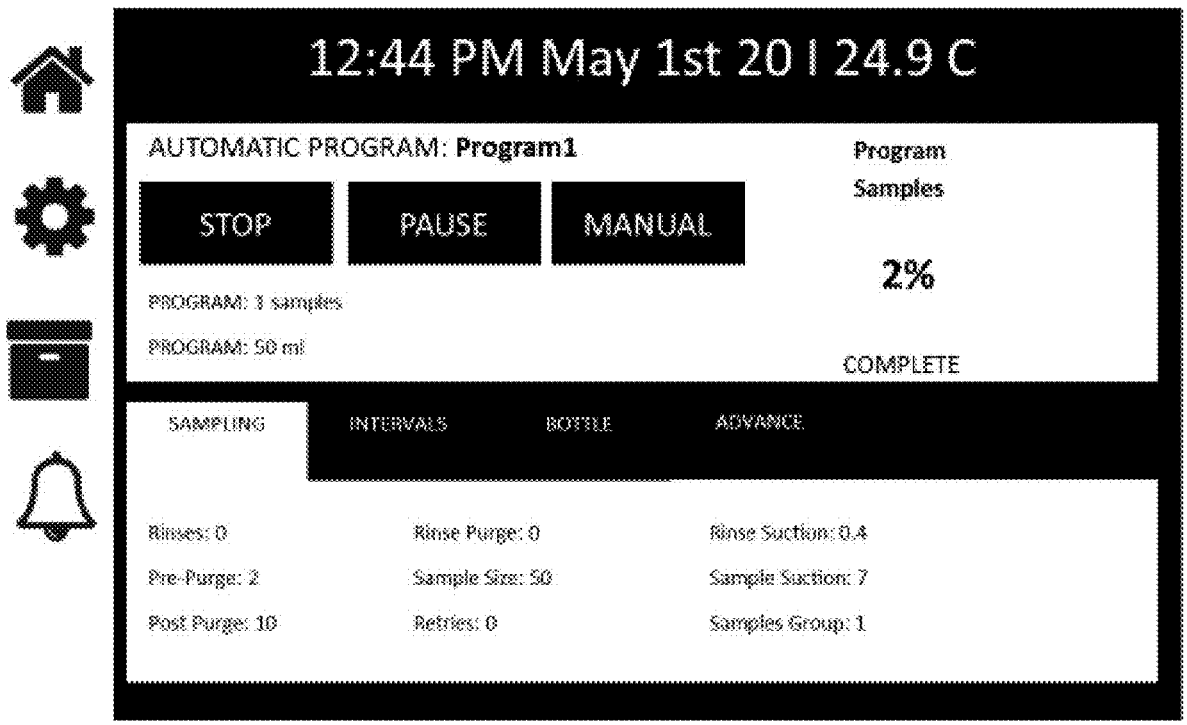

To start a program that is already programmed, press the Run button from the home screen (FIG. 125). Before pressing the Run Button, notice that the Program State is IDLE PROGRAM and that the Current activated Program is Program1. After pressing the Run button, notice that the Program State is AUTOMATIC PROGRAM (FIG. 126). Once the program is running, new buttons will be displayed on the screen; STOP—Program stops running; PAUSE—The current program will pause; MANUAL—Pressing this button will make the sampler pull a manual sample. This Manual Sample will be counted in the overall samples to be pulled in the program.

Figure 127:
Figure 127:
Figure 127:
Figure 127:

While the Home Screen has the Sampling Tab selected, the screen will display in the upper right the Percentage (for example 2%) of samples completed (FIG. 127). Underneath the Stop Button the number of samples that have been pulled and a running total of the ml pulled will be displayed.

Figure 128:
Figure 128:
Figure 128:
Figure 128:
Figure 129:

Pressing the Stop button will cause the program to display a Warning! message and ask for confirmation to Stop the program from running (FIG. 128). This allows to Cancel or proceed by pressing Confirm! Pressing Confirm will stop the current program and show why the program stopped to the right of the RESET button. For example, "STOP CAUSE: user" (FIG. 129).

Figure 130:

When RESET is pressed, the Home screen is displayed (FIG. 130).

Figure 131:
Figure 131:
Figure 131:
Figure 131:

When the sampler is in the process of pulling a Sample, the Stop, Pause and Manual buttons are not displayed, and a Cancel button is displayed (FIG. 131). The Cancel button allows cancellation of the current sample at its current point in the sampling process. Once the sample process has started, in the bottom right-hand side of the screen an indicator displays where the current program is at in its sampling process.

Figure 132:
Figure 132:
Figure 132:
Figure 132:

Pressing the PAUSE button will Pause the current running sampling program (FIG. 132). When the program goes into Pause, the PAUSE button changes to the RESUME button. Pressing the RESUME button will start the program again.

Figure 133:
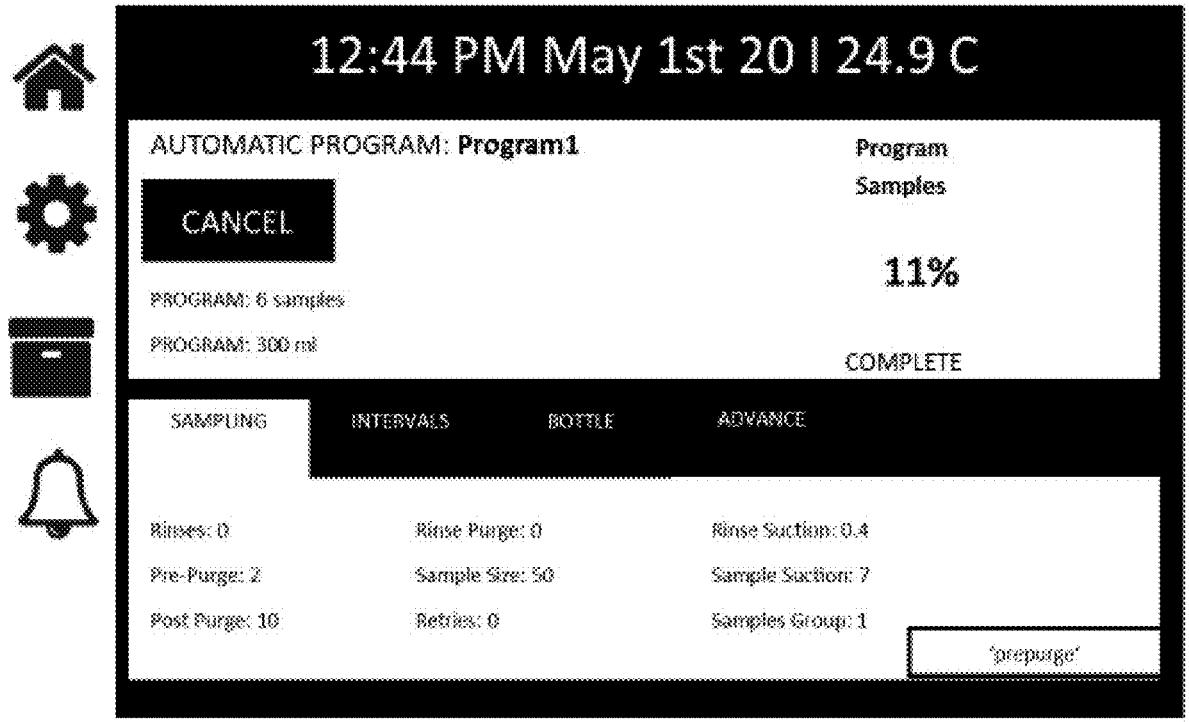
Figure 134:
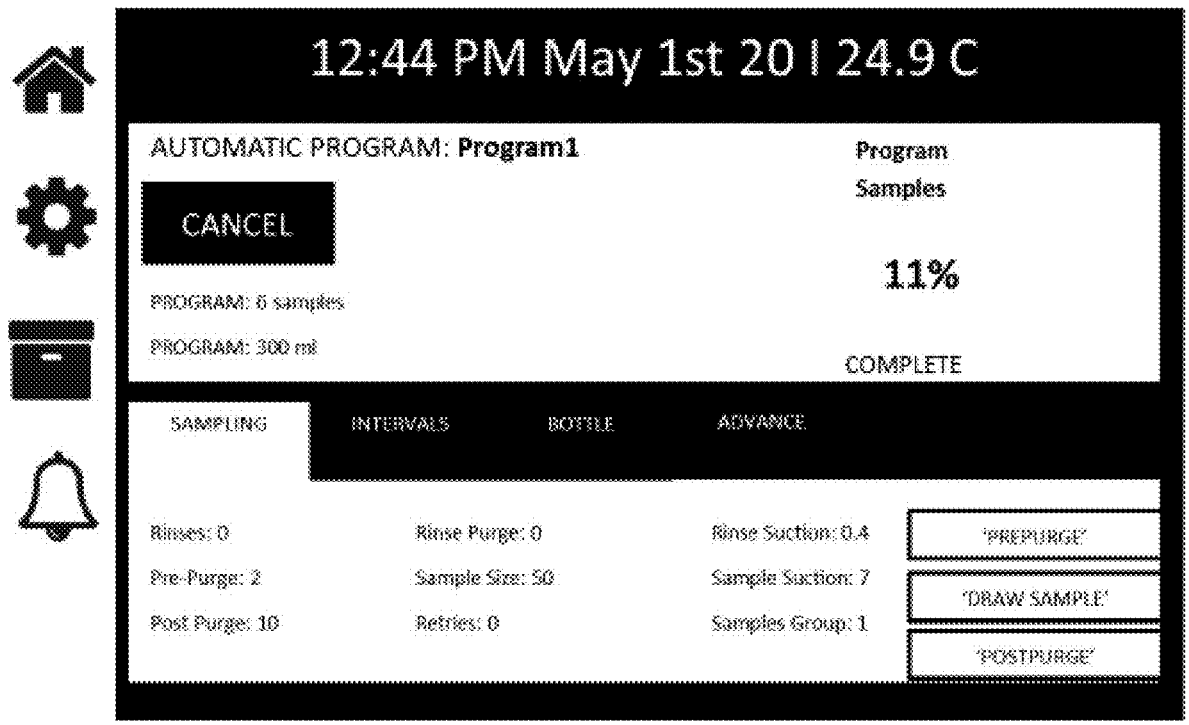
Figure 135:
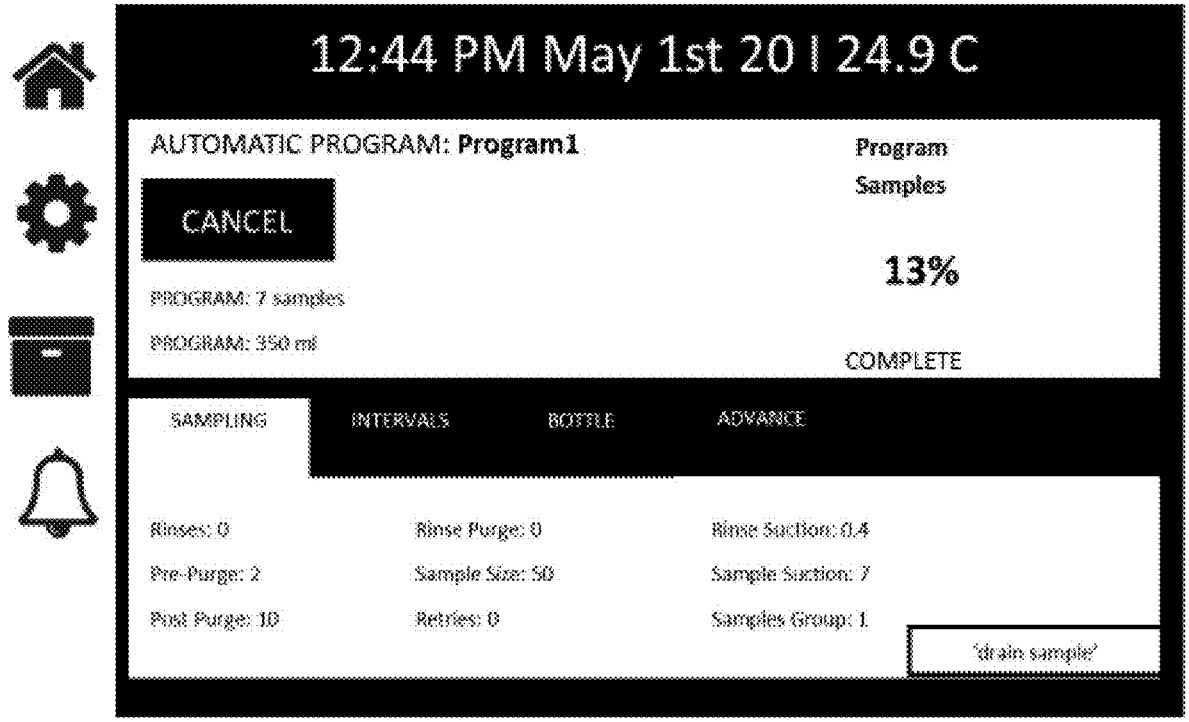
Figure 136:
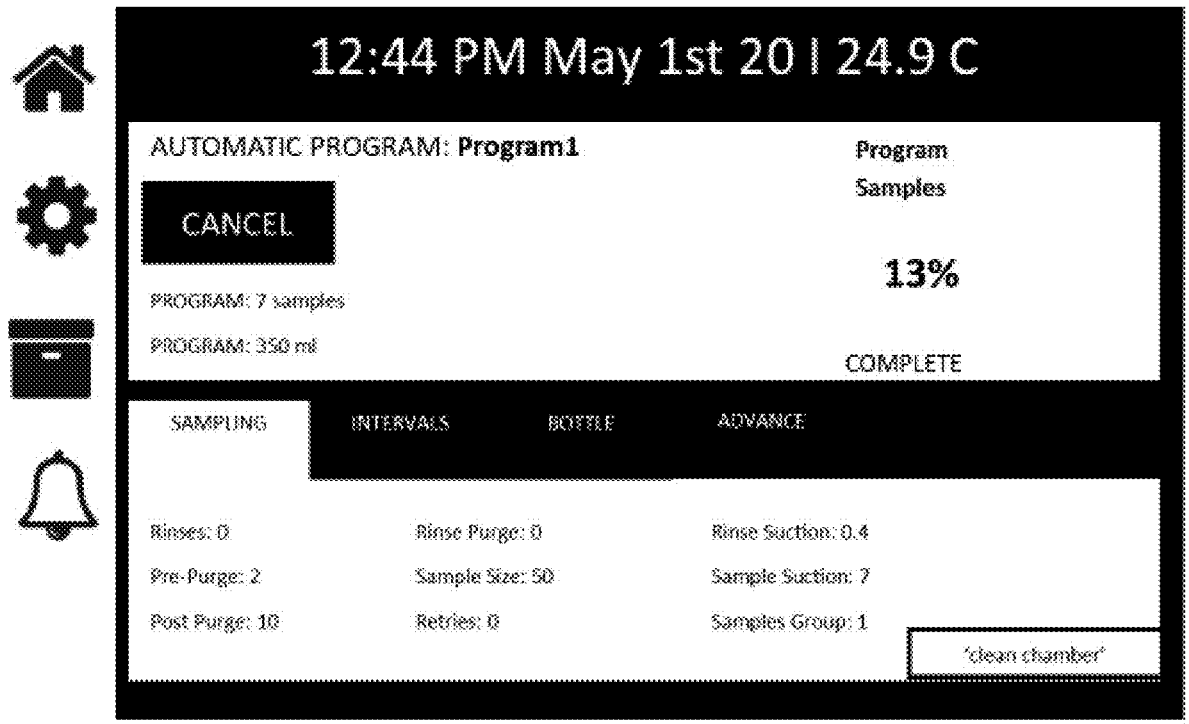
Figure 137:
Figure 138:
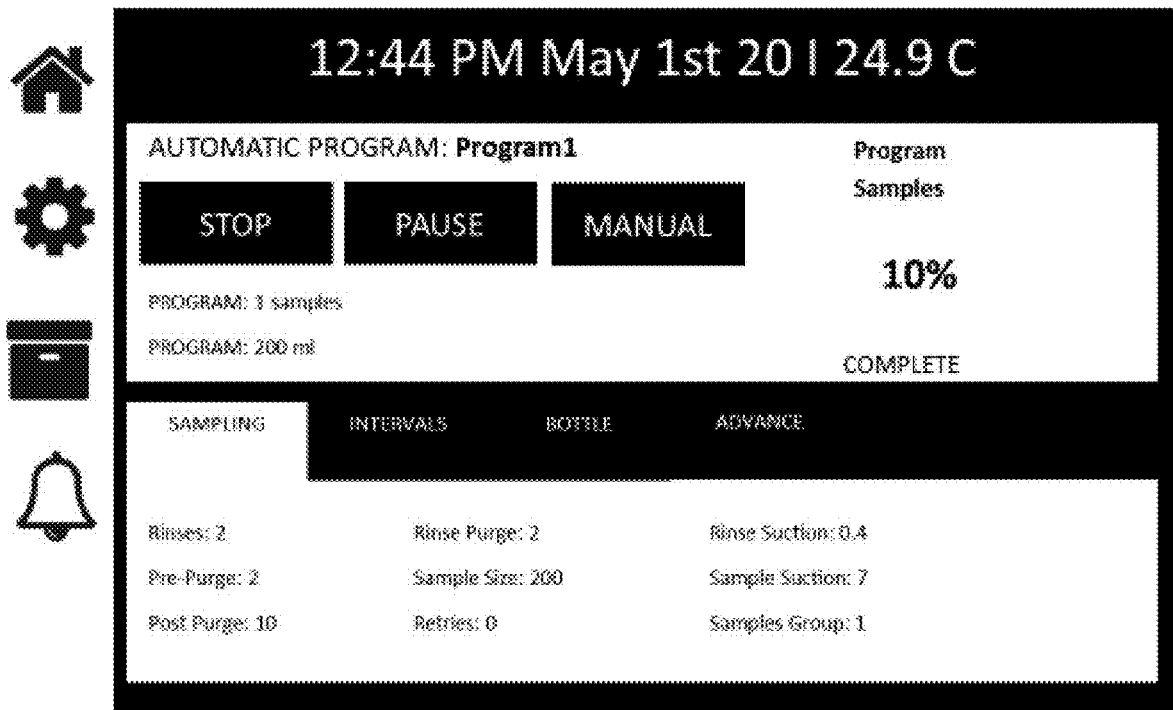
Figure 139:
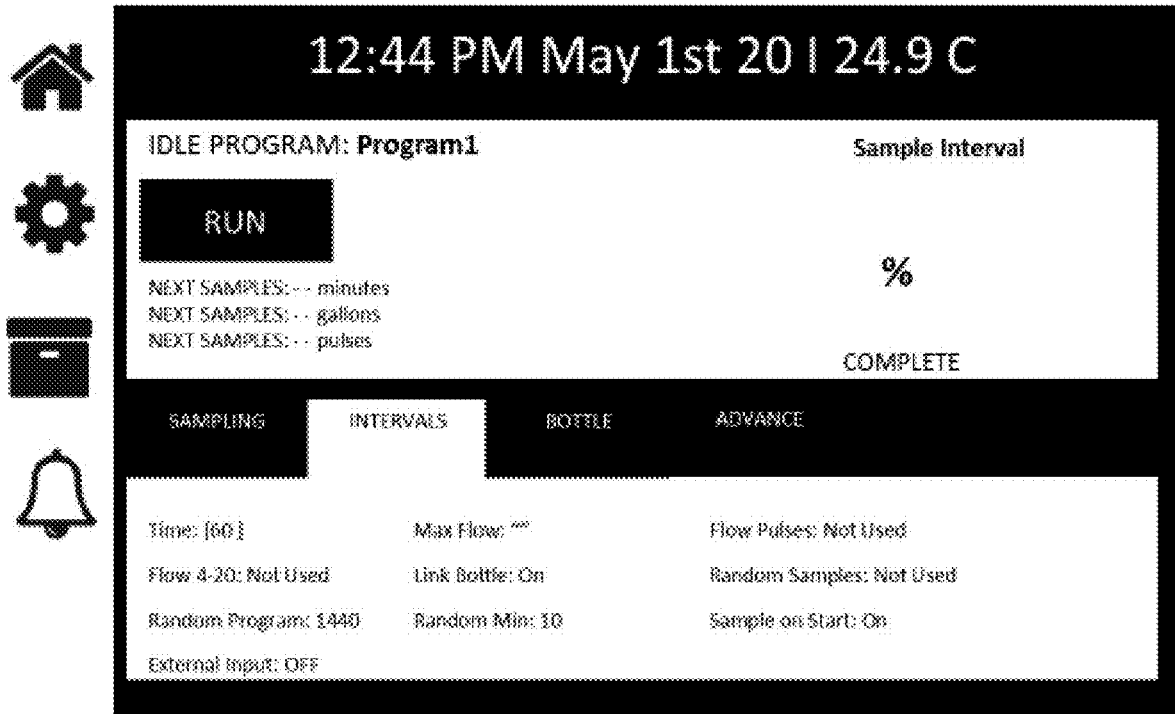
Figure 140:
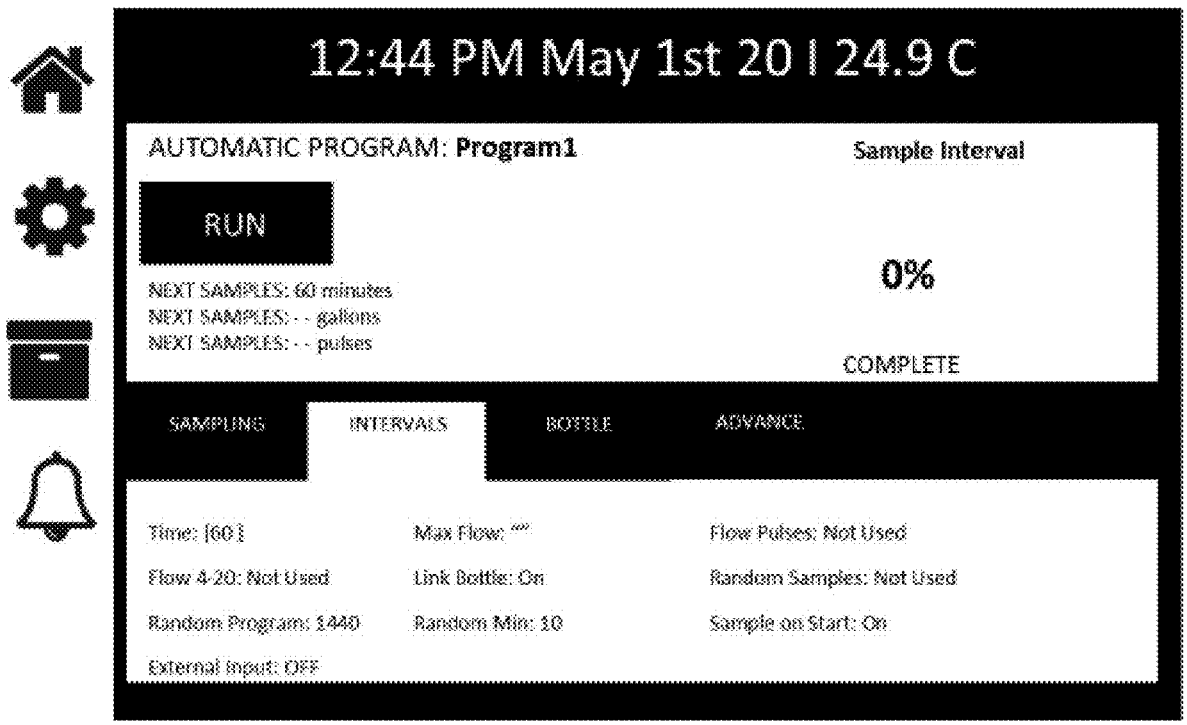
Figure 141:
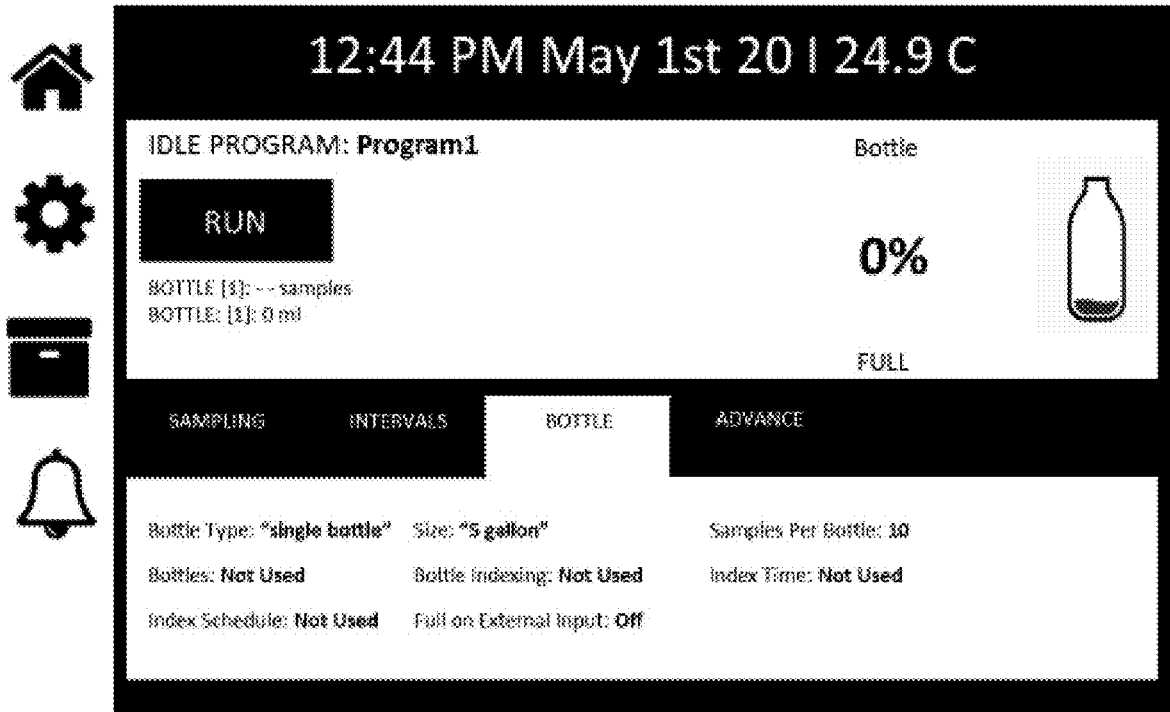
Figure 142:
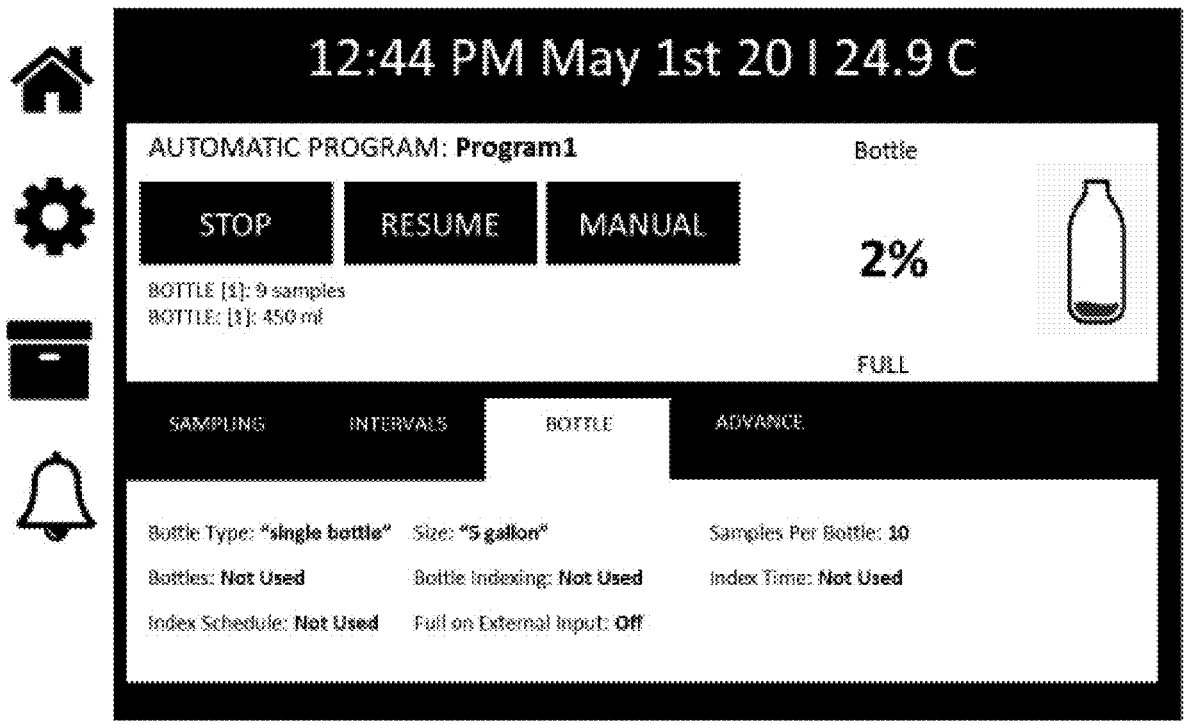
Figure 143:
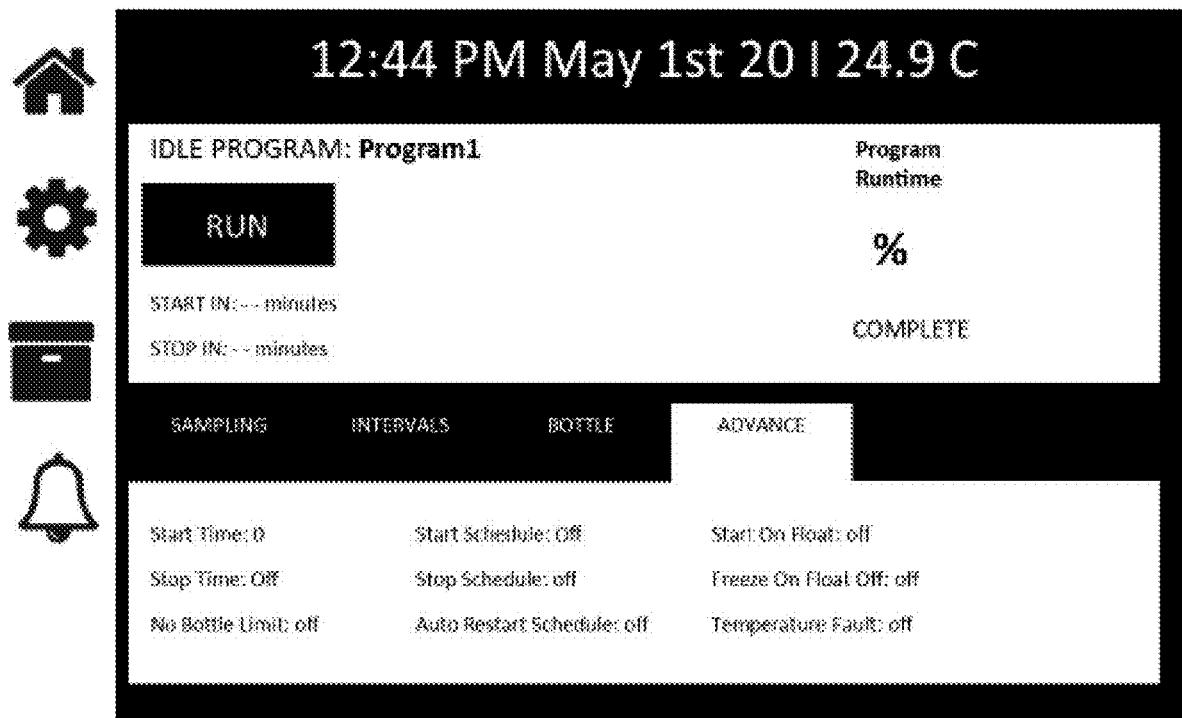
Figure 144:
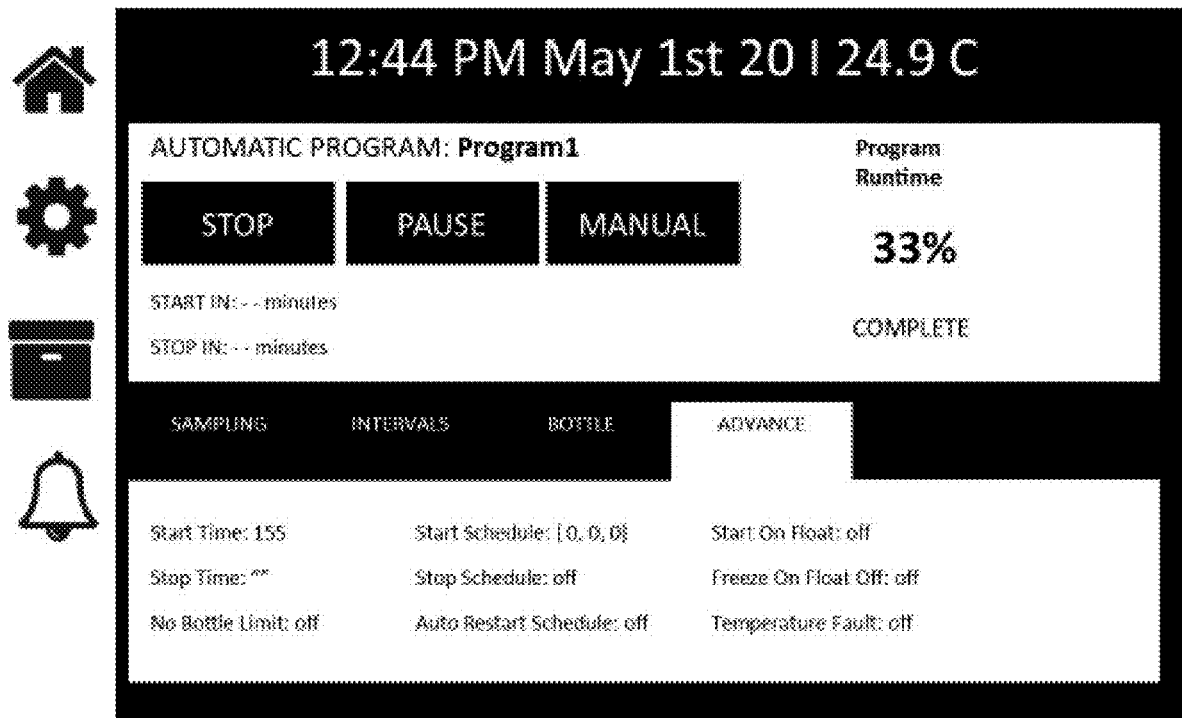

When the sampling process is running, the current process is displayed in the bottom right of the screen (FIGS. 133 and 134). Once the Pre-purge is completed the sampler will Draw Sample then Post-Purge. Once these have been completed, the sampler is draining the sample into the bottle is displayed (FIG. 135) and then clean chamber is displayed (FIG. 136).

The Tabs (Sampling, Intervals, Bottle and Advance) are used for two different purposes. The information above each tab shows the current sampling status while in the Run mode and below the tab is how the sampler is programmed (see FIGS. 137-144).

The Archive files and Alerts can be accessed by touching the file icon or the red bell for alerts on the left side of the screen.

Figure 145:
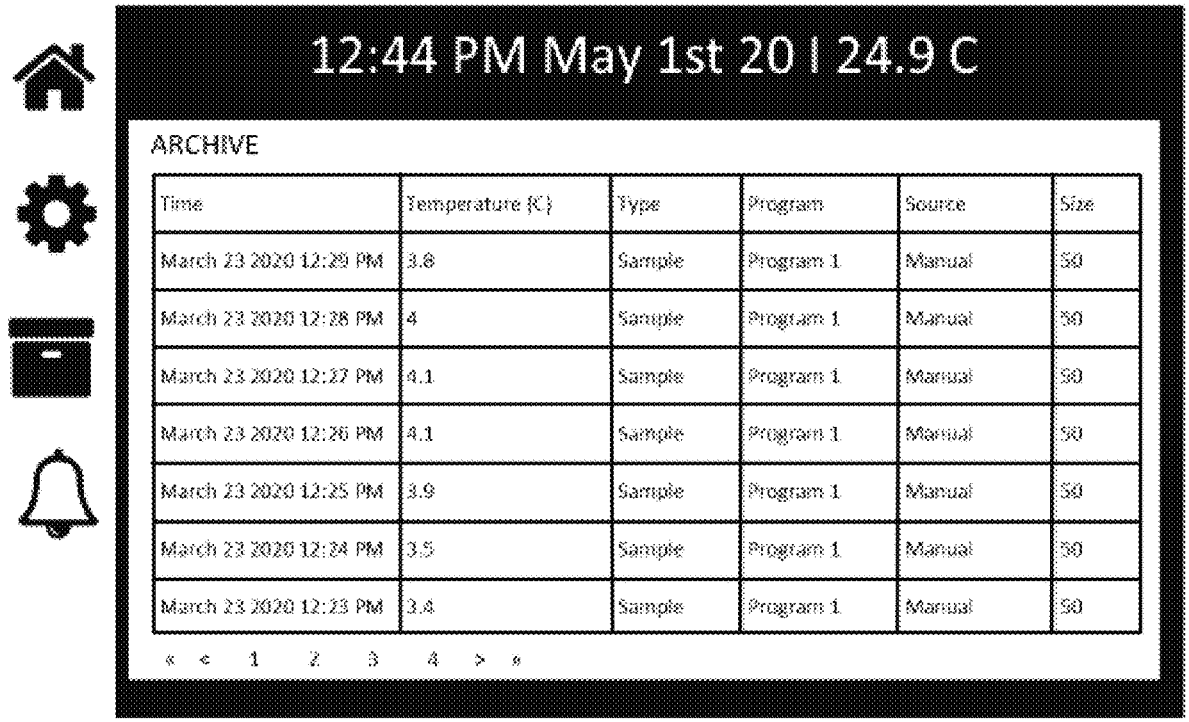

The Archive file collects data for each sample taken (FIG. 145).

Figure 146:
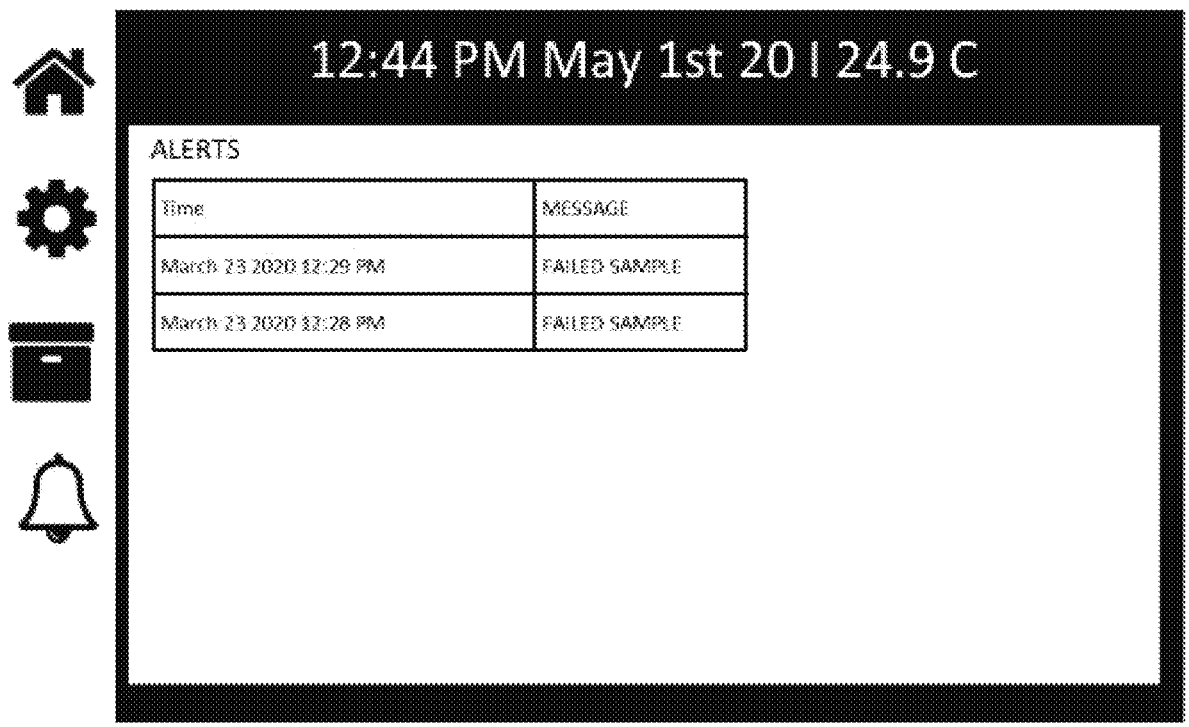

The Alerts file shows data if there is an issue with a current sample event (FIG. 146).

It is to be understood that while certain now preferred forms of this invention have been illustrated and described, it is not limited thereto except insofar as such limitations are included in the following claims. Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned may be completed without departing from the scope of the claims below. Certain features and sub-combinations are of utility and may be employed without reference to

Having thus described the invention, what is claimed as new and desired to be secured by Letters Patent is:

1. A method for wastewater sampling comprising:
   radially positioning, by a controller, a first end of a sample tube within a sample chamber to receive a wastewater sample volume;
   directing, by the controller, a vacuum/pressure pump to initiate a vacuum cycle to pull a vacuum on the sample chamber to draw the wastewater sample into the sample chamber; and
   energizing, by the controller, the vacuum/pressure pump to pressurize the sample chamber upon receiving a predetermined oversample volume of the wastewater sample to force the oversample volume from the sample chamber.

2. The method of claim 1 wherein said sample chamber includes an arcuate outer wall, and wherein the first end of said sampling tube remains equidistant from an inner surface of the arcuate outer wall as the sampling tube rotates within the sample chamber.

3. The method of claim 1 further comprising energizing a pinch valve assembly including a drain line coupled to a drain of the sample chamber, by the controller to selectively drain the sample chamber.

4. The method of claim 1 further comprising selectively energizing a refrigeration unit by the controller coupled to maintain the wastewater sample at a predetermined temperature.

5. The method of claim 1 further comprising energizing the vacuum/pressure pump for a predetermined period of time for a sample tube position for a sample size by the controller.

6. The method of claim 1 further comprising energizing the vacuum/pressure pump for a measured flow rate for a sample size by the controller.

7. The method of claim 1 wherein said system controller energizes said vacuum/pressure pump for a combination flow rate and period of time for a predetermined sample size.

8. The method of claim 1 further comprising a vacuum termination means coupled to said system controller to prevent collection of excess wastewater in the sample chamber during the vacuum cycle.

9. The method of claim 8 wherein the vacuum termination means comprises a sample balance coupled to the sample chamber for measuring the weight of the sample chamber, the controller coupled to the sample balance to receive an output therefrom to terminate the vacuum cycle and initiate the pressure cycle.

\* \* \* \* \*